US006713263B2

(12) United States Patent
Schwartz

(10) Patent No.: US 6,713,263 B2
(45) Date of Patent: Mar. 30, 2004

(54) METHOD FOR MAPPING A NUCLEIC ACID

(75) Inventor: David C Schwartz, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/238,407

(22) Filed: Sep. 9, 2002

(65) Prior Publication Data

US 2003/0027201 A1 Feb. 6, 2003

Related U.S. Application Data

(63) Continuation of application No. 09/713,016, filed on Nov. 16, 2000, now Pat. No. 6,448,012, which is a division of application No. 08/128,996, filed on Sep. 30, 1993, now Pat. No. 6,150,089, and a continuation-in-part of application No. 07/879,551, filed on May 4, 1992, now Pat. No. 5,405,519, and a continuation-in-part of application No. 07/333,531, filed on Apr. 5, 1989, now abandoned, which is a continuation-in-part of application No. 07/244,897, filed on Sep. 15, 1988, now abandoned.

(51) Int. Cl.$^7$ .......................... C12Q 1/68; G01N 33/00

(52) U.S. Cl. .............................. 435/6; 436/94

(58) Field of Search ................ 435/6; 436/94

(56) References Cited

U.S. PATENT DOCUMENTS

| | | | |
|---|---|---|---|
| 4,473,452 A | | 9/1984 | Cantor et al. |
| 4,695,548 A | | 9/1987 | Cantor et al. |
| 4,767,700 A | | 8/1988 | Wallace |
| 4,870,004 A | | 9/1989 | Conroy et al. |
| 4,881,812 A | | 11/1989 | Ohkubo et al. |
| 5,030,566 A | | 7/1991 | Son et al. |
| 5,405,519 A | * | 4/1995 | Schwartz ............... 204/299 R |
| 5,599,664 A | * | 2/1997 | Schwartz ............... 435/6 |
| 6,150,089 A | * | 11/2000 | Schwartz ............... 435/6 |
| 6,221,592 B1 | * | 4/2001 | Schwartz et al. ............. 435/6 |
| 6,355,420 B1 | | 3/2002 | Chan ............... 435/6 |
| 6,448,012 B1 | * | 9/2002 | Schwartz ............... 435/6 |
| 6,509,158 B1 | * | 1/2003 | Schwartz ............... 435/6 |

FOREIGN PATENT DOCUMENTS

| | | |
|---|---|---|
| EP | 0 391 674 | 10/1990 |
| WO | WO 89/01620 | 2/1989 |

OTHER PUBLICATIONS

Bendich et al., "Moving pictures and pulsed–field gel electrophoresis show linear DNA molecules from chloroplasts and mitochondria," *Current Genetics* 17:421–425 (1990).
Cooney, C., "Separation and Size Determination of DNA over a 10–200 kbp Range," *Methods in Molecular Biology* 12:31–37 (1992).
Guo et al., "Sizing of Large DNA Molecules by Hook Formation in a Loose Matrix," *Journal of Biomolecular Structure & Dynamics* 11:001–010 (1993).
Gurrieri et al., "Imaging of Kinked Configurations of DNA Molecules Undergoing Orthogonal Field Alternating Gel Electrophoresis by Fluorescence Microscopy," *Biochemistry* 29:3396–3401 (1990).
Mathew et al., "High–Resolution Separation and Accurate Size Determination in Pulsed–Field Gel Electrophoresis of DNA. 1. DNA Size Standards and the Effect of Agarose and Temperature," *Biochemistry* 27:9204–9210 (1988).
Matsumoto et al., "Light Microscopic Structure of DNA in Solution Studied by the 4',6–Diamidino–2–phenylindole Staining Method," *J. Mol. Biol.* 152:501–516 (1981).
Morikawa et al., "Visualization of Individual DNA Molecules in Solution by Light Microscopy: DAPI Staining Method," *J. Biochem.* 89:693–696 (1981).
Schwartz, et al, "ED:pulsed electrophoresis instrument," *Nature* 342:575–576 (1989).
Shin et al, "Separation and Size Determination of Circular and Linear Single–Stranded DNAs by Alkaline Agarose Gel Electrophoresis," *Analytical Biochemistry* 226:202–206 (1996).
Smith et al., "Electrophoretic Charge Density and Persistence Length of DNA as measured by Fluorescence Microscopy," *Biopolymers* 29:1167–1173 (1990).
Stellwagen, N., "Orientation of DNA Molecules in Agarose Gels by Pulsed Elctric Fields," *Journal of Biomolecular Structure and Dynamics* 3:299–314 (1985).

(List continued on next page.)

Primary Examiner—Kenneth R. Horlick
(74) Attorney, Agent, or Firm—Quarles & Brady LLP

(57) ABSTRACT

A method for observing and determining the size of individual molecules and for determining the weight distribution of a sample containing molecules of varying size, which involves placing a deformable or nondeformable molecule in a medium, subjecting the molecule to an external force, thereby causing conformational and/or positional changes, and then measuring these changes. Preferred ways to measure conformational and positional changes include: (1) determining the rate at which a deformable molecule returns to a relaxed state after termination of the external force, (2) determining the rate at which a molecule becomes oriented in a new direction when the direction of the perturbing force is changed, (3) determining the rate at which a molecule rotates, (4) measuring the length of a molecule, particularly when it is at least partially stretched, or (5) measuring at least one diameter of a spherical or ellipsoidal molecule. Measurements of relaxation, reorientation, and rotation rates, as well as length and diameter can be made using a light microscope connected to an image processor. Molecule relaxation, reorientation and rotation also can be determined using a microscope combined with a spectroscopic device. The invention is particularly useful for measuring polymer molecules, such as nucleic acids, and can be used to determine the size and map location of restriction digests. Breakage of large polymer molecules mounted on a microscope slide is prevented by condensing the molecules before mounting and unfolding the molecules after they have been placed in a matrix.

10 Claims, 16 Drawing Sheets

OTHER PUBLICATIONS

Sturm et al., "Direct Observation of DNA Chain Orientation and Relaxation by Electric Birefringence:Implications for the Mechanism of Separation during Pulsed–Field Gel Electrophoresis," *Physical Review Letters* 62:1484–1487 (1989).

Yanagida, et al., "Dynamic Behaviors of DNA Molecules in Solution Studied by Fluorescence Microscopy," *Cold Spring Harbor Symp. Quant. Biol.* 47:177–187 (1982).

* cited by examiner

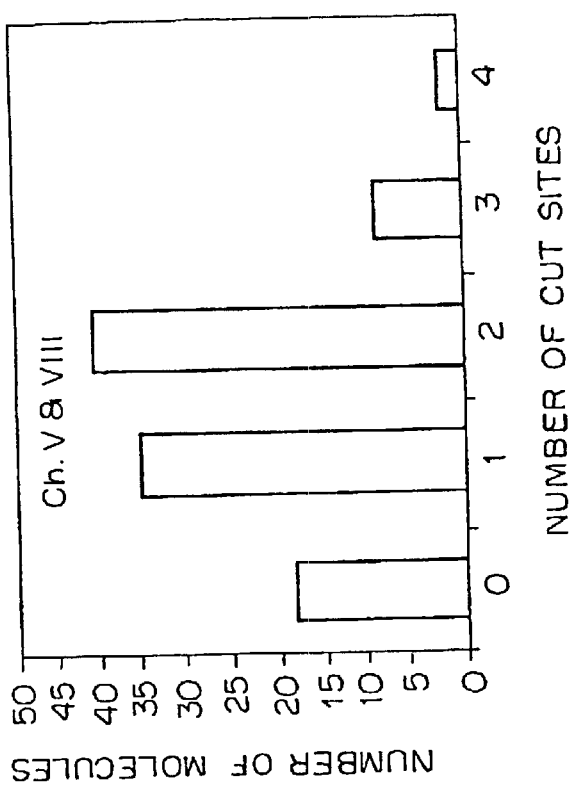
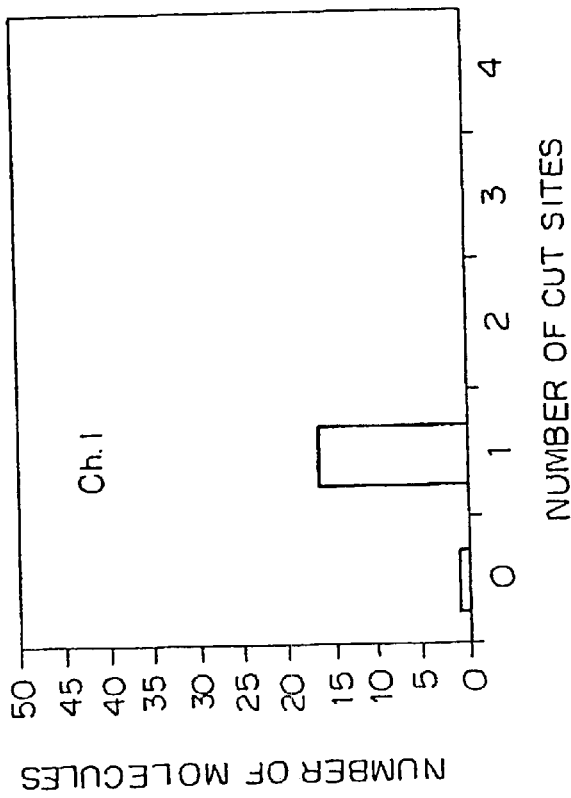

↓ CUT SITE

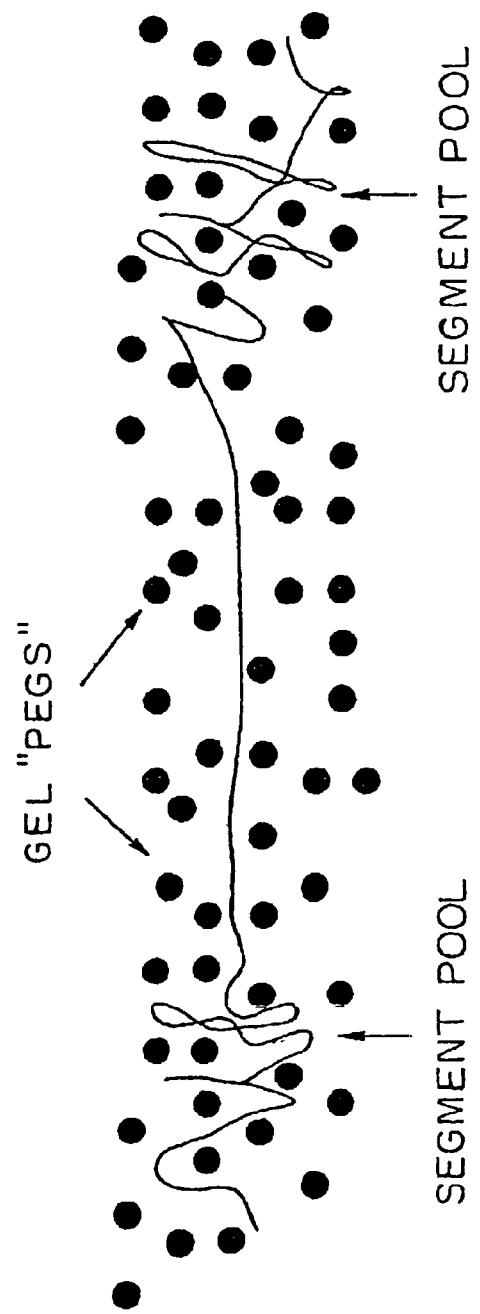

METHOD FOR MAPPING A NUCLEIC ACID

CROSS-REFERENCE TO RELATED APPLICATIONS

This application is a continuation of application Ser. No. 09/713,016 filed Nov. 16, 2000, now U.S. Pat. No. 6,448,012 which was a division of application Ser. No. 08/128,996, filed Sep. 30, 1993, now U.S. Pat. No. 6,150,089, which is a continuation-in-part of each of U.S. application Ser. No. 07/244,897, filed Sep. 15, 1998, Ser. No. 07/333,531, abandoned filed Apr. 5, 1989, and Ser. No. 07/879,551, filed May 4, 1992, now U.S. Pat. No. 5,405,519 the entire contents of each of which applications are hereby incorporated herein by reference. Application Ser. No. 07/879,551 is a continuation-in-part of said application Ser. No. 07/244,897.

GOVERNMENT LICENSE RIGHTS

This invention was made with U.S. Government support under Contract No. GM 37277 awarded by the National Institute of General Medical Sciences of the United States Department of Health and Human Services and the U.S. Government has certain rights in the invention.

FIELD OF THE INVENTION

This invention, in the fields of electrophoresis, microscopy, spectroscopy and molecular biology, relates to methods for characterizing polymer molecules or the like, for example, observing and determining the size of individual particles and determining the weight distribution of a sample containing particles of varying size. More particularly, this invention involves the use of microscopy and/or spectroscopy in combination with spectroscopic methods to characterize particles, e.g., nucleic acids, such as by measuring their positional and conformational changes when they are subjected to an external force, such as a restriction enzyme digest and by measuring their length and diameter or radius.

BACKGROUND OF THE INVENTION

Traditionally, the molecular weight distribution of a sample of particles has been determined by measuring the rate at which particles which are subjected to a perturbing force move through an appropriate medium, e.g., a medium which causes the particles to separate according to size. A mathematical relationship is calculated which relates the size of particles and their migration rate through a medium when a specified force is applied.

Sedimentation is a well-known technique for measuring particle size, but, when applied to polymers, this method is limited to molecules with a maximum size of about 50–100 kilobases (kb). Attempting to measure larger molecules by this technique would probably result in underestimation of molecular size, mainly because the sedimentation coefficient is sensitive to centrifuge speed. See Kavenoff et al., *Cold Spring Harbor Symp. Quantit. Biol.*, 381 (1974)).

Another popular method of separating polymer particles by size is by gel electrophoresis (see, e.g., Freifelder, *Physical Biochemistry*, W. H. Freeman (1976), which is particularly useful for separating restriction digests. In brief, application of an electric field to an agarose or polyacrylamide gel in which polymer particles are dissolved causes the smaller particles to migrate through the gel at a faster rate than the larger particles. The molecular weight of the polymer in each band is calibrated by a comparison of the migration rate of an unknown substance with the mobility of polymer fragments of known length. The amount of polymer in each band can be estimated based upon the width and/or color intensity (optical density) of the stained band. However, this type of estimate is usually not very accurate.

Pulsed field electrophoresis, developed by the present inventor and described in U.S. Pat. No. 4,473,452, which is hereby entirely incorporated herein by reference, is an electrophoretic technique in which the separation of large DNA molecules in a gel is improved relative to separation using conventional electrophoresis. According to this technique, deliberately alternated electric fields are used to separate particles, rather than the continuous fields used in previously known electrophoretic methods. More particularly, particles are separated using electric fields of equal strength which are transverse to each other, which alternate between high and low intensities out of phase with each other at a frequency related to the mass of the particles. The forces move the particles in an overall direction transverse to the respective directions of the fields. It should be noted here that the term "transverse" as used herein is not limited to an angle of, or close to, 90°, but includes other substantial angles of intersection.

One of the most significant problems with determining the weight of molecules by indirect measurement techniques, such as those described above, is that the parameters which are directly measured, e.g., migration rate, are relatively insensitive to small differences in molecular size. Thus, a precise determination of particle size distribution is difficult to obtain. The lack of precision may particularly be a problem when biological polymer samples, which tend to be unstable and contain single molecules inches in length, are involved.

While some of the known methods of determining particle size distribution in a polydisperse sample provide better resolution than others, few, if any, of the previously known techniques provide resolution as high as is needed to distinguish between particles of nearly identical size. Gel permeation chromatography and sedimentation provide resolution of only about $M^{1/2}$ (M=molecular weight). Standard agarose gel electrophoresis and polyacrylamide gel electrophoresis provide resolution varying as –log M. Pulsed electrophoretic techniques are effective for separating extraordinarily large molecules, but do not provide much better resolution than standard electrophoresis. Thus, the ability to distinguish between particles of similar size, for example, particles differing in length by a fraction of percent, is inaccurate and problematic using the above-described measurement techniques.

Particles of higher mass (i.e., up to approximately 600 kb) can be resolved using conventional gel electrophoresis by reducing the gel (e.g., polyarylamide) concentration to as low as 0.035% and reducing field strength. However, there are also problems with this method. Most notably, the dramatic reduction in gel concentration results in a gel which is mechanically unstable, and less sample can be loaded. An electrophoretic run to resolve very large DNA molecules using a reduced gel concentration and field strength may take a week or more to complete. Furthermore, a reduced gel concentration is not useful to separate molecules in a sample having a wide range of particle sizes, because separation of small molecules is not achieved. Thus, if a sample containing molecules having a wide range of sizes is to be separated, several electrophoretic runs may be needed, e.g., first, a separation of the larger molecules and then further separation of the smaller molecules.

Other particle measurement techniques known in the art are useful for sizing certain molecules which are present in a bulk sample, (e.g., the largest molecules in the sample, or the average molecular size) but are impractical for measuring many polymers of varying length in a given sample. The viscoelastic recoil technique, (see Kavenoff et al, "Chromosome-sized DNA molecules from *Drosophila*," *Chromosoma* 411 (1973)) which is well known in the art, involves stretching out coiled molecules in a solvent flow field (e.g., a field which is created when fluid is perturbed between two moving plates) and determining the time required for the largest molecule to return to a relaxed state. Relaxation time is measured by watching the rotation of a concentric rotor which moves during the time of relaxation. While this technique is quite precise in that sample determinations vary as $M^{1.66}$ when applied to large DNA molecules, it is not useful for sizing molecules other than the largest molecule in the sample.

Using light scattering techniques, which are known in the art, (e.g., quasi-elastic light scattering), the size and shape of particles are determined by a Zimm plot, a data analysis method which is known in the art. With these techniques, size dependence varies as $M^1$. Light scattering requires that the solution in which the molecules to be measured are placed is pure, that is, without dust or any other contamination, and it is therefore unsuitable for sizing a DNA sample. Furthermore, it is not useful for sizing molecules as large as many DNA molecules, and is useful only for determining the average weight of particles in a sample, not the weight distribution of a sample with particles of various sizes.

Yet another particle measuring technique which is known in the art for measuring individual molecules provides measurements of particle size having limited accuracy. The average size and shape of individual, relaxed DNA molecules has been determined by observing the molecules under a fluorescence microscope, and measuring the major and minor axes of molecules having a spherical or ellipsoid shape (see Yanagida et al, *Cold Spring Harbor Symp. Quantit. Biol.* 47, 177, (1983)). This technique is performed in a free solution, without perturbation of the molecules.

The movement of small DNA molecules during electrophoresis has been observed (see Smith et al. *Science*. 243203 (1989)). The methods disclosed in this publication are not suitable for observation of very large DNA molecules, and techniques for measuring molecules are not discussed.

Practical weight determinations of particles such as polymer molecules depend not only upon maximizing the size dependencies of the directly measured parameters, but also upon factors such as the amount of sample needed, the time required to complete an analysis, and the accuracy of measurements. Gel permeation chromatography can be time-consuming and requires a large amount of sample. Methods such as conventional gel electrophoresis can be relatively time-consuming, require moderate amounts of sample, and cannot size very large DNA molecules.

Molecular sizing is a fundamental operation that touches virtually every aspect of genomic analysis from DNA sequencing to size measurements of lower eucaryotic chromosomal DNAs. Molecular size, given in kilobases, can be translated into centimorgans for many organisms, and vice-versa; and gel electrophoresis is generally used to determine these sizes. The basics in nucleic acid sizing technology, as practiced by the typical molecular biologist, have not changed very much in the past decade. This is understandable considering the simplicity of gel electrophoresis and its capacity for parallel processing of multiple samples. The data obtained from gels are readily interpretable. Given the size of most genes, gel electrophoresis techniques adapt well to their analysis. From characterization of restriction digests to discernment of one base differences in sequencing ladders, gel electrophoresis is the method of choice for size analysis of DNAs. Even the outcome of PCR (Mullis, *Methods in Enzymol*, 155335–350 (1987)) reactions is frequently monitored by sizing analysis. Pulsed gel electrophoresis extends this coverage even further to include chromosomal DNAs from lower eucaryotes (Schwartz, *Cold Spring Harbor Symp. Quant. Biol.*, 4789 (1983); Schwartz *Cell*, 3767 (1984); Carle, *Nucleic Acids. Res.* 125647 (1984); Chu, *Science* 2341582 (1986); Clark, et al., *Science* 2411203 (1988). Because pulsed electrophoresis can resolve very large DNA molecules, its application has simplified the mapping of large genomes and provided a necessary tool for creating large YACs (yeast artificial chromosomes) (Barlow, et al., *Trends in Genetics* 3167–177 (1987); Campbell, et al. *Proc. Natl. Acad. Sci.* 885744 (1991)). However, pulsed electrophoresis was developed more than 10 years ago (Schwartz, *Cold Spring Harbor Symp. Quant. Biol.* 4789 (1983) and Schwartz *Cell*, 3767 (1984)). The surprising lack of significant sizing advances is contrasted to progress made in understanding the molecular mechanisms of conventional and pulsed electrophoresis (Zimm, *Quart. Rev. Biophys.* 25171 (1992); Deutsch, *Science* 240992 (1988).

Although molecular size determination has not advanced significantly in this decade, another aspect of genomic analysis, DNA detection technology, has progressed to a remarkable extent. These developments have impacted on gel-based methodologies as well as on the field of cytogenetics. A driving force has been the Human Genome Initiative and its goals to characterize the human genome and the genomes of model organisms by extensive mapping and sequencing. The new goals aimed at analyzing entire large mammalian genomes include increasing accuracy and high throughput of DNA mapping and sequencing. The first round of needed advances has come in part from a combination of sophisticated image processing methods (Glazer, *Nature* 359859 (1992); Quesada, *BioTechniques* 10616 (1991); Mathies, *Nature* 359167 (1992)); new DNA detection techniques and new DNA labeling/imaging systems (Glazer, *Proc. Natl. Acad. Sci.* 873851 (1990); Beck, *Nucleic Acids Res.* 175115 (1989)). Automation of gel electrophoresis based technologies demands clear, relatively unambiguous detection systems for operator-free function (Lehrach, *Cold Spring Harbor Press*, Cold Spring Harbor, N.Y. pp39–81 (1989); Larin, *Proc. Natl. Acad. Sci.*, 884123 (1991)). Sophisticated computational methods can extract usable data automatically from difficult conditions. A good example of a fully integrated approach to mapping comes from the Cohen laboratory which has combined all of these technological approaches together with "mega-YACs" (Bellanne-Chantelot, et al., *Cell* 70L1059 (1992)) to maximally boost output to a dramatic extent, although with problems inherent in the fidelity of these YACs (Anderson, *Science* 2591684 (1993)).

Construction of physical maps for eucaryotic chromosomes is laborious and difficult, in part because many of the current methodologies for mapping and sequencing DNA were originally designed to analyze genes rather than genomes, so that at present there is a premium on automating procedures such as PCR and blot hybridizations (Chumakov, *Nature* 359380 (1992)). Two techniques have played a fundamental role in the process of ordering and sizing DNA sequences from eucaryotic chromosomes. Electrophoretic methods have the advantage of good size resolution, even for long chains, but require DNA in bulk amounts. Sources include genomic DNA or YACs (Burke, *Science* 236806 (1987)). Single molecule techniques, such as fluorescence in-situ hybridization or (FISH), utilize only a limited number of chromosomes (Manuelidis, *J. Cell. Biol.* 95L619–625 (1982)) but have not yet attained a sizing capability comparable to that of pulsed electrophoresis. Ideally, one would like to be able to combine the sizing power of electrophoresis with the intrinsic loci ordering capability of FISH in order to construct accurate restriction maps very rapidly.

All considered, the evolution of various physical and genetic techniques has enabled far more to be accomplished than expected toward creation of a complete, physical map of whole chromosomes and the entire human genome (Bellanne-Chantelot, et al., *Cell* 70L1059 (1992); Chumakov, et al., *Science* (1992); Mandel, et al., *Science* 258103 (1992)). Despite this progress the situation can be improved in the following areas.

For fingerprinting YACs, chromosomal DNA is digested with several enzymes and then blotted and sometimes hybridized with several different repetitive sequences (Bellanne-Chantelot, et al., *Cell* 70L1059 (1992); Stallings, et al., *Proc. Natl. Acad. Sci.* 876218 (1990); Ross, et al., Techniques for the Analysis of Complex Genomes, Academic Press, Inc., San Diego, Calif., (1992)). Here, electrophoresis is used to size restriction fragments that are specifically identified by hybridization. The data density available for such an analysis is relatively low. For example, it is difficult to discern more than 100 bands in a given land in a typical agarose gel. Additionally, restriction fragments that are the same size cannot be resolved from each other and can only be discerned by careful, differential hybridization. Therefore, the fingerprint does not report nearly as much information as what would result if an ordered restriction map were to be made with the same enzyme(s) or even an accurate histogram of the size population. Such a histogram can only be obtained from gels by difficult measurements of band fluorescence intensities.

Gels are time-consuming. It takes time and care to pour gels and minutes to days to run, and it can take several days to do Southern analysis, although gels offer the opportunity for parallel sample analysis and, with multiplexing techniques (Church, et al., *Science* 240185 (1988)), this tremendous ability is probably maximized, sizing results are often difficult to digitize and to automatically tabulate.

Electrophoretic size resolution for commonly run agarose gels rarely exceeds mass. Although under limited conditions greater size resolution can be obtained (Calladine, *Journal of Molecular Biology* 221981 (1991)). Greater size resolution would enable simpler fingerprints with a higher information content. Although pulsed electrophoresis techniques can, under certain circumstances, boost size resolution, these results can be hard to interpret except in very narrow size ranges. Ultimately, these measured sizes are dependent on size markers which are limited in range for very large DNA molecules. For pulsed electrophoresis, the determined size is frequently inadequately interpolated between several size markers.

(iv) Usable sensitivity is limited to the subpicogram range except by exotic techniques (Glazer, et al., *Nature* 359859 (1992); Quesada, *BioTechniques* 10616 (1991)). However, now common phosphor imager systems have improved sensitivity some and make quantitation easier. The usable sensitivity range will dictate the type of sample that can be analyzed. For example, single-copy mammalian genomic hybridizations can be challenging to a novice. Mapping of end-labeled partial digestion of genomic DNAs is often not successful because of loss of attending sensitivity (Smith, et al., *Nucleic Acids Res.* 32387 (1976)) so that extensive analysis is difficult to do with genomic DNA samples. This necessitates the reliance on cloned genomic material, despite their limitations including problems with uncloneable regions, rearrangements and deletions. Although YACs enable cloning of such large genomic fragments and have served as the basis for many mapping approaches, they are not perfect mapping reagents and must therefore be used with great caution (Anderson, *Science* 2591684 (1993); Vollrath, et al., *Science* 25852 (1992); Foote, et al., *Science* 25860 (1992)).

Citation of documents herein is not intended as an admission that any of the documents cited herein is pertinent prior art, or an admission that the cited documents are considered material to the patentability of the claims of the present application. All statements as to the date or representations as to the contents of these documents are based on the information available to the applicant and does not constitute any admission as to the correctness of the dates or contents of these documents.

SUMMARY OF THE INVENTION

The present invention provides methods for physically characterizing large or small molecules, including polymers and particles, for determining molecule size, molecular weight, size distribution, weight distribution and/or enzyme cleavage maps of a homogenous, heterogenous, or polydisperse or varying sample of molecules.

This invention can determine at least one of molecule size, weight and cleavage or restriction maps using faster and more efficient methods, which also can provide better resolution, than methods known in the related art.

This invention also can size one or more particles or molecules using an extremely sensitive method, e.g., one which can use an amount of sample, e.g., as small as a few molecules or a single molecule.

Accurate size information for a polydisperse sample containing molecules having a wide range of sizes, is also provided, as well as providing this information more quickly than by using previously known techniques.

Methods of the present invention involve characterizing individual molecules, including deformable and non-deformable molecules, in a polydisperse sample by placing the molecules in a medium, applying an external force to the molecules, thereby causing physical changes (particularly conformational and/or positional changes), and then observing and measuring these changes. This method is useful for characterizing molecules of a variety of sizes, including the smallest molecules which are detected by a suitable microscope (the microscope optionally may be attached to a spectroscopic apparatus and thus molecules too small to be visualized may still be detected), and large polymers, which may be up to several or many inches in length when stretched to a linear conformation. Shear sensitive molecules (e.g., large molecules), which cannot be placed on a microscope slide without breaking when conventional techniques are used, are measured according to this invention by collapsing (condensing) the molecules before they are placed in the medium and then uncollapsing them after placement in the medium. This invention is useful for characterizing many types of particles which can be visualized or detected under a light microscope. Several non-limiting examples include polysaccharides, polypeptides, proteins, and nucleic acids (e.g., DNA or RNA).

Deformable molecules are particles or molecules which have a tendency to change conformation (shape), as well as position, when they are subjected to an external force. Non-deformable particles or molecules tend to have a substantially stable conformation even when subjected to an external force, but may undergo changes in position. Deformable molecules are usually reversibly deformable, e.g., they change conformation when an external force is applied, and then return to a configuration comparable to their original shape when application of the force is terminated.

This invention is particularly useful for measuring polymer molecules which are folded, coiled and/or supercoiled and are subject to conformational changes such as stretching, bending, twisting, contracting, and the like, as well as positional changes such as rotating, translating and the like. This invention is particularly useful when an external force is applied to molecules which are in some type of medium. However, if a free solution is used, application of an external force may not be needed to cause the molecules to change conformation or position.

Molecules which are large enough to be seen using a microscope are measured by visualization, e.g., by direct observation of a microscopic image. Particles may, alternatively, be measured using microscopy combined with any suitable spectroscopic technique, particularly if the particles are too small to be imaged (viewed with acceptable resolution).

Several non-limiting examples of useful spectroscopic methods include using polarized radiation as generated by a laser combined with measurement of refractive index or fluorescence dichroism, or using sensitive video cameras such as cooled charged coupled devices, silicon intensified target devices, and micro-channel plate detectors.

Samples containing a mixture of both small and large molecules, for example, small and large DNA molecules including chromosomes, are sized rapidly, with each molecule in the sample being measured simultaneously. The method of this invention involves measuring conformational and positional changes of individual, discrete molecules (or other particles), as contrasted to methods known in the art, which characterize a sample in bulk. The method of this invention may be applied to measure any number of molecules, ranging from a single molecule to a large number of molecules. If a sample containing a large number of molecules is measured, the number of molecules which are observed at one time will depend in part upon the field of view of the microscope and the extent to which the molecules are separated from each other. Viewing discrete, individual molecules, or measuring their role of relaxation after applying an external force permits complete deconvolution or separation of measured parameters.

The medium used in this invention is any suitable material. Preferably the medium will hold relaxed molecules in a relatively stationary position and yet permit movement of molecules which are subjected to an external force. However, a free solution also may be used. For measurements of molecular movement, a suitable medium is any medium which will permit different molecules to change conformation and position at different rates, depending upon their size, and perhaps upon their chemical composition.

For many uses of this invention, the preferred medium is a gel or a liquid. Preferably, the medium is anticonvective, but this is not absolutely necessary. The medium may or may not be inert. The choice of an appropriate medium will depend in part upon the size of the molecules which are measured, the tendency for the molecules to change position and shape, and the desired precision of the measurements. For example, when large molecules (or other molecules of similar size) are measured, a gel with a large pore size is preferably used.

The external force applied to the molecules is any force which causes the nondeformable or deformable molecules to undergo changes in conformation or position. For example, the force may be an electric field, solvent flow field, or a magnetic field, but is not limited to these types. The force may vary in direction, duration and intensity. A particularly useful way to perturb the molecules is by using electrophoresis, or by site specific enzyme digest, e.g., restriction enzyme digest of a DNA molecule.

The types of changes which are measured in this invention primarily include changes in conformation or shape, including stretching and relaxation rates, as well as length and diameter (or radius) measurements, and changes in position, including changes in orientation and rotation as well as translation within the medium. Molecules may undergo changes in conformation or position, or both. Different types of changes are measured according to various embodiments of the invention.

The techniques for measuring conformational and positional changes include, but are not necessarily limited to, microscopy (alone), and microscopy combined with spectroscopy. Several non-limiting examples of useful spectroscopic techniques include birefringence, linear or circular dichroism, and detection of fluorescence intensity.

Molecules which are large enough to be seen under a microscope can be measured by visualizing (imaging) the molecules. As non-limiting examples, a light microscope or a scanning/tunneling microscope may be used. While molecules may be viewed directly, it is useful to link the microscope to a low light sensitive video camera, connected to a computerized image processor (e.g., as described herein or as would be suggested to one skilled in the relevant arts) which records a series of photographs, even a motion picture, by digitizing or recording the images which are received. The image processor may itself comprise a computer, or may be linked to a computer which processes data based upon the images. Use of a computerized apparatus enables the movement of each individual molecule to be measured simultaneously. Furthermore, the relationship of molecules to one another may be detected, and several different parameters of a single molecule can be measured simultaneously.

Optionally, the microscope and image processor are connected to a spectroscopic apparatus. This technique is particularly useful for molecules which are too small to be visualized, but is also useful for sizing larger molecules as well.

In order to transform measurements of change in conformation and position into size measurements, it is generally necessary to generate (or otherwise obtain) data relating to physical changes of molecules of known size when the molecules are subject to external forces. "Markers" are developed by measuring the parameters of molecules with known values of molecular weight. This information may be input into a computer or data processor in order to establish a relation between molecular weight and particular conformational and positional changes which are measured. Preferably, the markers are molecules of similar chemical structure to the molecules of unknown size (e.g., both molecules contain the similar chemical components), because rates of relaxation, reorientation and rotation may be dependent upon molecule composition. However, this may depend upon one or more other variables, e.g., polymer size, composition, molecular weight, pKa, amino acid or nucleic acid sequence, etc., and thus it may not always be necessary for the "markers" to have a composition similar to that of the molecules of unknown size.

Shear sensitive molecules are molecules which are subject to breaking when they are placed on a microscope slide using conventional methods. According to another aspect of this invention, such molecules may be collapsed into a higher density conformation before they are placed in a medium, in order to prevent breakage when the molecules are mounted on a microscope slide. Once they have been placed in the medium, they can be uncollapsed and measured by the same methods as the smaller molecules.

In one embodiment of the present invention, fluorescently stained, deformable molecules which are coiled, folded or otherwise configured in a native relaxed, folded or complexed conformation are placed in a medium and are temporarily deformed, related, unfolded, separated, cleaved or stretched by applying an external force. When application of the force is stopped, the relaxation or reversion time of the molecules (e.g., the time required for the molecules to return to their original, native state) is determined by direct microscopic observation of molecular movement or change, or by at least one of microscopy and spectroscopy. Alternatively, the kinetics of stretching are measured by following the stretching of the molecule after initiation of the external force. Rate measurements are calculated in various ways, for example, by determining an amount of change per unit time. Rates of change for molecules of unknown size are determined based upon rates of molecules of known size, such as by interpolation or extrapolation.

As, e.g., with the viscoelastic measurement technique known in the art, the relaxation time of molecules in a liquid according to this embodiment varies as about $M^{1.66}$. In a gel, it is believed that resolution may be as high as $M^{2-4}$. This is based upon known theoretical principles which show that molecules reptate in gels or confining matrices, and their relaxation time is much greater in a gel than in a solution (see, e.g., DeGennes, P. E., Scaling Concepts in Polymer Physics, Cornell University Press, N.Y. (1979)).

In a second embodiment, the reorientation time of a deformable or non-deformable molecule is measured. When molecules are first subjected to a perturbing force in one direction, and the direction of the perturbing force is then changed, for example, by 90° or other transverse angle, such as 10–90°, 20–90°, 30–90°, 40–90°, 50–90° or any range or value therein, small molecules quickly reorient themselves and start a new migration along the new path. Larger molecules, on the other hand, remain substantially immobile until they are reoriented in the direction of the electric field. Then, they too begin to move in the new direction. By that time, the smaller molecules will have moved ahead. Measurements of the rate at which the position of a molecule changes with respect to an external force may be measured, for example, by measuring changes in position (e.g., lateral and/or rotational movement) per unit time.

In a third embodiment, the rate at which a molecule rotates is determined when a series of external forces are applied. This method is particularly applicable to rod-shaped molecules, such as small DNA molecules, and elongated molecules which are maintained in a relatively uniform conformation. "Rotation time" according to this invention is the amount of time required for a molecule to undergo a positional rotation of a particular angular increment, for example, 360°, when a particular set of external forces are applied.

By periodically switching pulse direction, intensity and length, molecules are caused to move slightly back and forth as they are rotated. This facilitates rotation, and is analogous to the way in which an automobile is manipulated into or out of a parallel parking space by alternating backward and forward motion. However, unlike an automobile, a rod-shaped or coil molecule may bend somewhat as it rotates. A pulsing routine may also function to keep a deformable molecule in a generally consistent conformation, in order to provide useful measurements, e.g., measurements which relate rotation time to molecular size.

Data for reorientation and/or rotation rates for molecules of known size may be used to develop a relationship between reorientation and/or rotation rate and molecular size, which then may be used to determine the size of various polymer molecules of similar composition and unknown size, such as those which are present in a polydisperse sample. Reorientation and rotation rate may be determined using microscopy (preferably combined with image processing) to directly observe positional changes, or by combining microscopy with spectroscopic measurements. Thus, these embodiments are useful not only for mid-sized and large molecules, but also for molecules that are too small to be imaged with acceptable resolution.

In yet another embodiment of this invention, the length of a molecule which has been placed in a medium is directly measured using microscopy. This technique provides direct measurement of the molecular size of any number of molecules. This method generally involves observing the curvilinear length of deformed molecules which are in a stretched state, e.g., during the application of an external force, or soon after termination of a force which has stretched a molecule. However, this method also may be applied to non-deformable molecules having an elongated shape, and measurement of such molecules does not require application of an external force before measurements are made. Preferably, this embodiment uses the same microscopy and imaging equipment as is described above.

In a fifth embodiment, the diameter (or radius) of molecules or other molecules suspended in a medium is measured. Application of a perturbing force is optional, because the diameter of a deformable molecule is preferably measured when the molecule is in a relaxed state, and the molecule is spherical, ellipsoidal or globular in shape. This embodiment may be used to measure molecules which are deformable or non-deformable, and involves the use of a light microscope attached to a computerized imaging device.

These five embodiments may be combined such that some or all of the above-mentioned parameters are measured simultaneously for one or more molecules.

A sixth embodiment of the invention is directed particularly to sizing very large molecules which tend to break if they are mounted on a microscope slide using conventional methods. In brief, this new technique involves collapsing the molecules before they are placed in the medium, using an agent which causes them to condense, and then uncollapsing the molecules after they have been placed in the medium. The molecules are then sized according to the method of embodiments one to five. The method for chemically collapsing molecules also may be used when it is desirable to place a large number of molecules in a small area, such as in microinjection, even if the molecules are not large or shear sensitive.

This invention provides a novel technique for mapping nucleic acid molecules. For example, when a nucleic acid is placed in a matrix and digested, the fragments are ordered by the computerized apparatus, and are sized by the methods described above. Thus, the order of the digests is quickly and accurately determined.

A further aspect of this invention provides for sequencing nucleic acid molecules by hybridizing probes to portions of a molecule. A nucleic acid is placed in a medium, to which suitable, desired probes are added. At least one recombinational enzyme may also be added. Reaction is initiated by an appropriate means, for example, the addition of ATP (adenosine triphosphate) and/or magnesium ions. After the probes have hybridized they are detected by the methods described above, namely, microscopy (alone) or microscopy in combination with spectroscopy.

Thus, the present invention provides an accurate method of determining the size of individual molecules and the weight distribution of a polydisperse sample of molecules. Another important advantage of this invention over the techniques of the prior art is that the measurable parameters for each molecule in a polydisperse sample, not just the largest molecule, are determined. Additional advantages are that (1) only one molecule is needed, and the sample may be very small, e.g., may consist of only one, or only a few molecules (2) measurements may be based on one representative molecule for each size in the sample, (3) the technique can be used for very large molecules (molecules too large to be measured by prior known methods), (4) data can be processed efficiently by computer, (5) measurements can be made more rapidly than methods known in the prior art (e.g. particularly as compared to slow electrophoresis processes, which may take several weeks), and (6) measurements are extremely accurate.

The present invention also can provide analysis of chromosomally sized DNA molecules and associated complexes utilizing new, ultra-rapid methodologies for determining the organization and structure of a eukaryote, such as an animal or human genome. Methodologies are provide which permit high resolution mapping for multiple individuals in a population of animals such as humans.

Such methods may involve optical mapping, which is a nonelectrophoretic approach, to rapidly create high-resolution ordered maps from chromosomally sized DNA molecules. Optical mapping produces ordered maps by fluorescently imaging single DNA molecules during restriction enzyme digestion. The resulting fragments are then sized by a number of single molecule methodologies according to the present invention. To facilitate mapping of mammalian genomes, optical mapping can be used to extend the size resolution to map fragments consisting of a few hundred base pairs, in addition to increase precision and throughput. To accomplish this, advanced intensity measurement techniques and sizing methodologies based on molecular relaxation can be used according to the present invention, as well as modified chamber designs and fixation techniques.

Detection Methods for Localization of Sequence Specific Sequences Including Hybridization to Single DNA Molecules. RecA protein-mediated hybridization approaches are also provided by the present invention, to precisely map sequences of large DNA by methods which may include optical mapping. Large target molecules can be imaged, localized and quantitated at specific sites via the visible gaps produced in the molecules at the hybridization site. Such sequence localization techniques can be combined in the present invention with sizing methodologies and sample handling techniques to improve throughput and versatility. Another method of the present invention is direct imaging of hybridization sites; this is based on conjugating RecA oligonucleotide filaments to different types of optically detectable tags allowing direct visualization of hybridization sites. Energy transfer techniques can also be used to enhance the specificity and effectiveness of tagged RecA-mediated hybridization as detected by imaging.

Increasing Throughput in mapping using Genomic DNA or YACs A number of single molecule methodologies can be combined in the present invention to dramatically increase the production of maps from YACs or genomic DNA. High throughput, flow-based optical mapping systems provided by this invention e.g., by producing high resolution, ordered restriction maps. RecA-assisted restriction endonuclease cleavage (RARE), according to this invention can selectively dissect genomes into large fragments. RARE and related techniques provide optical mapping approaches to rapidly map large genomic regions, without the need for cloning or sequencing.

Such optical mapping methodologies provide analysis methods for complex mammalian genomes, e.g., by applying sizing methodologies to raise the level of molecular size discrimination. These applications are facilitated by the discovery that relaxation phenomena of polymer molecules, e.g. DNA, demonstrate a remarkably high degree of size dependency. High throughput interfaces of methodologies of the present invention are also provided. The combination of high resolution and high throughput are preferably used with methods of this invention to provide high resolution maps of entire populations of a given species or animal subgroup. The value of cataloging high resolution maps of individuals for global genome comparisons is enormous, e.g., genetic analysis, and use in clinical settings for detecting complex heritable disorders, resulting from multi-genic determinants.

These and other advantages will become readily apparent from the detailed description which follows.

BRIEF DESCRIPTION OF THE DRAWINGS

FIGS. 7A–D shows histograms of optical mapping, with Not I cut frequencies showing variation with molecule size and number of cut sites. Cutting frequencies were scored by counting cuts in molecules present in microscope fields (containing typically 3–5 molecules). Because about half the fields showed no cutting and were not scored, this underestimates the number of uncut molecules. The expected number of cut sites and chromosome sizes, from (14) 7(A) Ch. I, 1(240 kb), 7(B) Ch. V and VIII, 3 and 2 (595 kb), 7(C) Ch. XI, 2 (675 kb), and 7(D) Ch. XIII and XVI, 1 (950 and 975 kb). Chromosome pairs V and VIII, and XIII and XVI coexist in the same mount.

FIG. 9 shows as graphic represent depicting possible relaxation events to form pools of segments or "balls" at coil ends. Agarose gel is illustrated as a series of pegs with free spaces available for molecules. Gel pegs might intersect the embedded DNA molecule during gelation and possibly entrap it. The coil segments positioned in the pool region comprise a relaxed sub-coil region and have higher entropy than the coil stretched out between them. These pools may act as molecular rivets in some circumstances, particularly if the segment pool mass approaches that of the intervening coil.

DETAILED DESCRIPTION OF THE INVENTION

Figure 1:
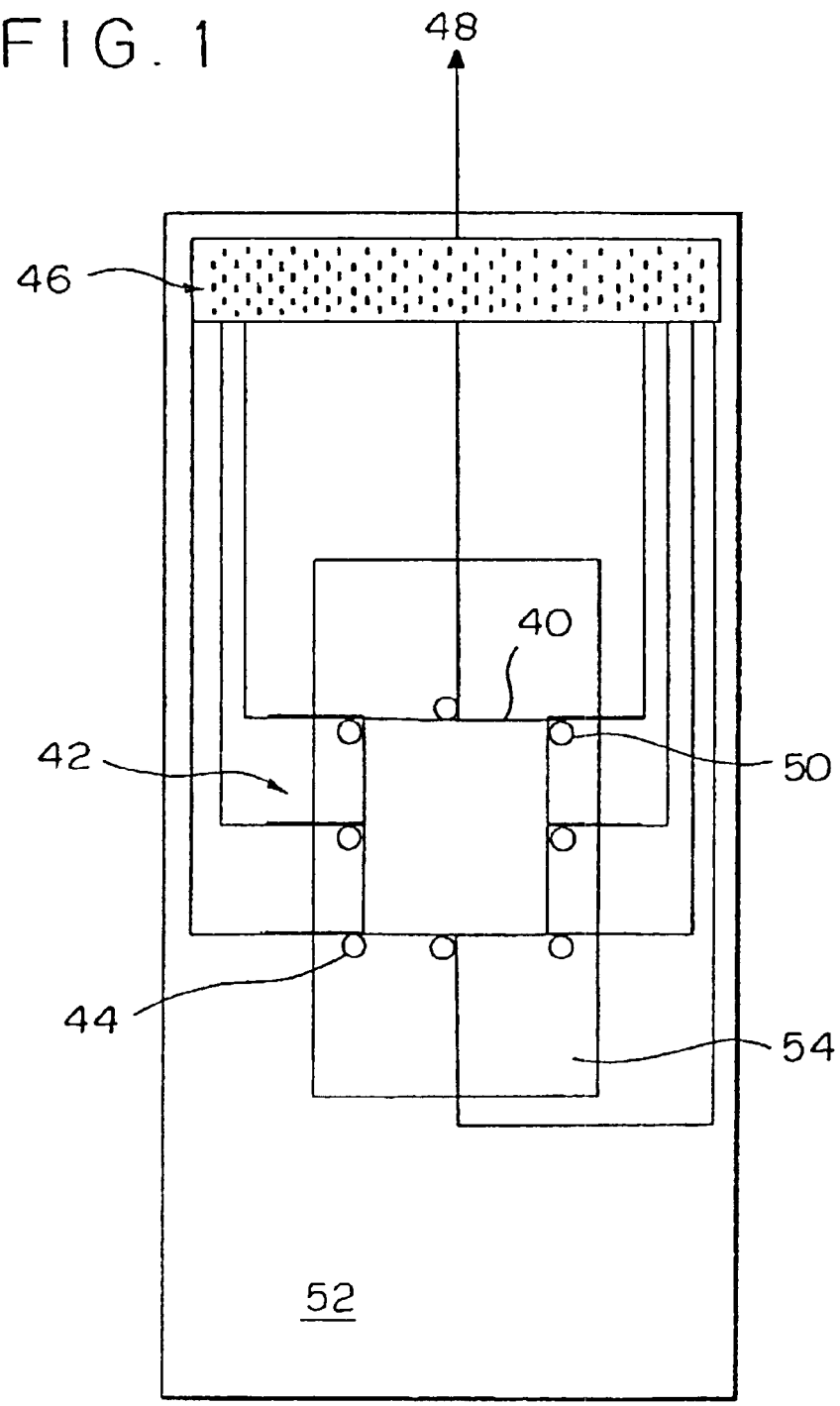
FIG. 1 is a schematic drawing of an electrophoretic microscopy chamber which is specifically adapted to fluorescence microscopy studies.

The present invention provides methods for characterizing physical and/or chemical properties of labeled and non-labeled molecules in a medium. Such properties may include but are not limited to, at least one of length, size, restriction maps, weight, mass, sequence, conformational or structural change, pKa change, distribution, viscosity, rates of relaxation, reorientation and rotation or other property of molecules subject to an external force, during or after the molecules are subjected to an external force.

Among other applications, these measurements may be used to determine molecule size. The invention is suited to size polymer molecules in a polydisperse sample (e.g., a sample containing molecules of varying size), when the molecules have been placed in some type of medium, and is useful to measure very large molecules, such as large nucleic acid molecules, which are subject to breakage when placed on a microscope slide using conventional methods. In several embodiments, molecules are measured either during or after they are deformed or repositioned by an external force. The method of this invention is particularly suitable for examination of nucleic acids and other polymers which are coiled, or possibly even supercoiled, when they are in a relaxed (unperturbed) conformation.

Methods for determining the molecular weight distribution of a polydisperse sample of molecules are useful in a variety of different fields. For example, in polymer chemistry, the properties of an oligomer are often dependent upon its molecular weight distribution. When a particular substance is found to exhibit favorable properties and the exact composition of the oligomer is not known, an analysis of the molecular weight distribution of the polymer is used for purposes of identification. In molecular biology, the molecular weight distribution of a polydisperse sample, such as a sample of DNA restriction enzyme digests, provides valuable information about the organization of the DNA. This information may be used to produce chromosome maps and extensive molecular genetics characterizations.

Molecules are placed in a medium, such as a solvent, powder, glass or gel. Other suitable mediums also may be used. The medium containing the molecules may be placed on a microscopic slide, or may be positioned in some other manner so as to permit the molecules to be viewed under the microscope. The suitability of a particular medium may depend in part upon the measurement technique to be used. Measurement techniques requiring perturbation necessitate the use of a medium in which deformable molecules are capable of changing conformation or position. When direct observations are made under a light microscope, a suitable medium also allows the molecules to be viewed clearly. When microscopy is combined with birefringence measurements, a preferred medium prevents convection and enhance the size dependency of the observed signal. Additionally, the medium itself preferably is relatively free of significant birefringence during experimental conditions.

Characterization of molecules based upon measurements of fluorescence intensity may be greatly enhanced using a matrix (e.g., a medium which partially confines molecule movement) as the medium. For the method of this invention, the medium is preferably a solution or gel. Agarose and polyacrylamide gels are particularly well suited for use in this invention. Examples of suitable solvents include glycerol/water, polydextran/water, and organic solvents. However, these examples are not to be construed as limiting the scope of the invention.

In a preferred embodiment, agarose, a polysaccharide derived from agar having an average molecular weight of approximately 100,000 daltons, is dissolved in an aqueous buffer (typically a 1% solution) and allowed to cool, forming a rigid gel, similar to gelatin (as found in Jello). The gel matrix consists of a three-dimensional network of agarose polymer chains annealed to each other through hydrogen bonding. Heating the agarose gel will send it back into a fluid state, so that the gel is said to be reversible, just like gelatin. The important feature of an agarose gel is its extraordinarily large average pore size. Although the pore voids in agarose gel are presently not completely characterized, they are thought to be approximately 0.3 microns wide, and also contain smaller voids. Due to its large pore size and inertness, agarose is used in DNA gel electrophoresis, because it allows DNA molecules to stretch and move in a gel.

If a fluorescence microscope is to be used (or if fluorescence intensity is to be measured by other means), the molecules generally are stained. Staining procedures are well known in the art. Useful stains or chromophore in this invention include, but are not limited to, ethidium bromide and 4',6-diamidino-2-phenyl-indole, dihydrochloride (DAPI). Most types of molecules are stained at some time before they are imaged, and may be stained before or after they are placed in a medium.

When a deformable molecule is placed in a medium and mounted on a slide, there are several possible ways to perturb the molecule. Several non-limiting methods are as follows. (1) A molecule is perturbed by the application of an electrical field, which moves a charged molecule such as DNA through a matrix, distorting the coil conformation much as cookie dough distorts as it moves through a forming machine. This is the phenomenon involved in gel electrophoresis. (2) A flow field is created in the liquid agarose/DNA (or polymer of choice) and the molecule-containing liquid is then gelled quickly with low temperature quenching, fast enough to prevent any significant coil relaxation. This method is useful whether or not the molecule is charged. (3) Using the dielectrophoresis effect, uncharged molecules with field gradients (electric fields which change strength with position) are moved by distorting molecular electron clouds, thus inducing attractable dipoles. It is believed that dielectrophoresis could be used in a matrix such as agarose.

One of the advantages in using electrophoresis is that DNA molecules are distinguished from other molecules which may be present in the DNA-containing medium because uncharged molecules do not move in response to application of an electric field. Another possible way to distinguish DNA molecules from others is to multiply the DNA.

The extent to which a molecule is to be perturbed, e.g., subjected to changes in conformation and/or position, before measurement, may vary. For example, useful data on molecular relaxation is obtained even when a coiled molecule is perturbed such that it is only partially uncoiled.

As mentioned above, one of the preferred methods for perturbing molecules according to this invention involves electrophoresis. Any electrophoresis method suitable for use with a microscope may be used according to the present invention to perturb the molecules. Electrophoresis may optionally serve another function in this invention. When a sample size is too large or complex to be viewed under a microscope all at once, molecules may be separated into sub-samples which then are imaged separately.

Electrophoresis of molecules for viewing and measuring purposes may optionally use a chamber which is suitable for use in pulsed field electrophoresis, as described in U.S. Pat. No. 4,695,548, or for pulsed oriented electrophoresis, which is described below. These techniques are particularly useful in the event it is desirable to measure reorientation and/or rotation times, because of the ability to control field angles.

Pulsed Oriented Electrophoresis (POE), which was developed by the present inventor and is the subject of co-pending application Ser. No. 07/244,897, improves separation of polydisperse polymer molecules in a sample by using short electric pulses to create and vary field angles, with the effective field angle being defined by the vector sum of a series of pulses which may vary in duration, intensity and direction. Pulse times and pulse intensities are modulated to effect separation. POE is also useful for creating effective field angles during imaging. The needed instrumentation is readily adapted to the microscope.

Figure 2:
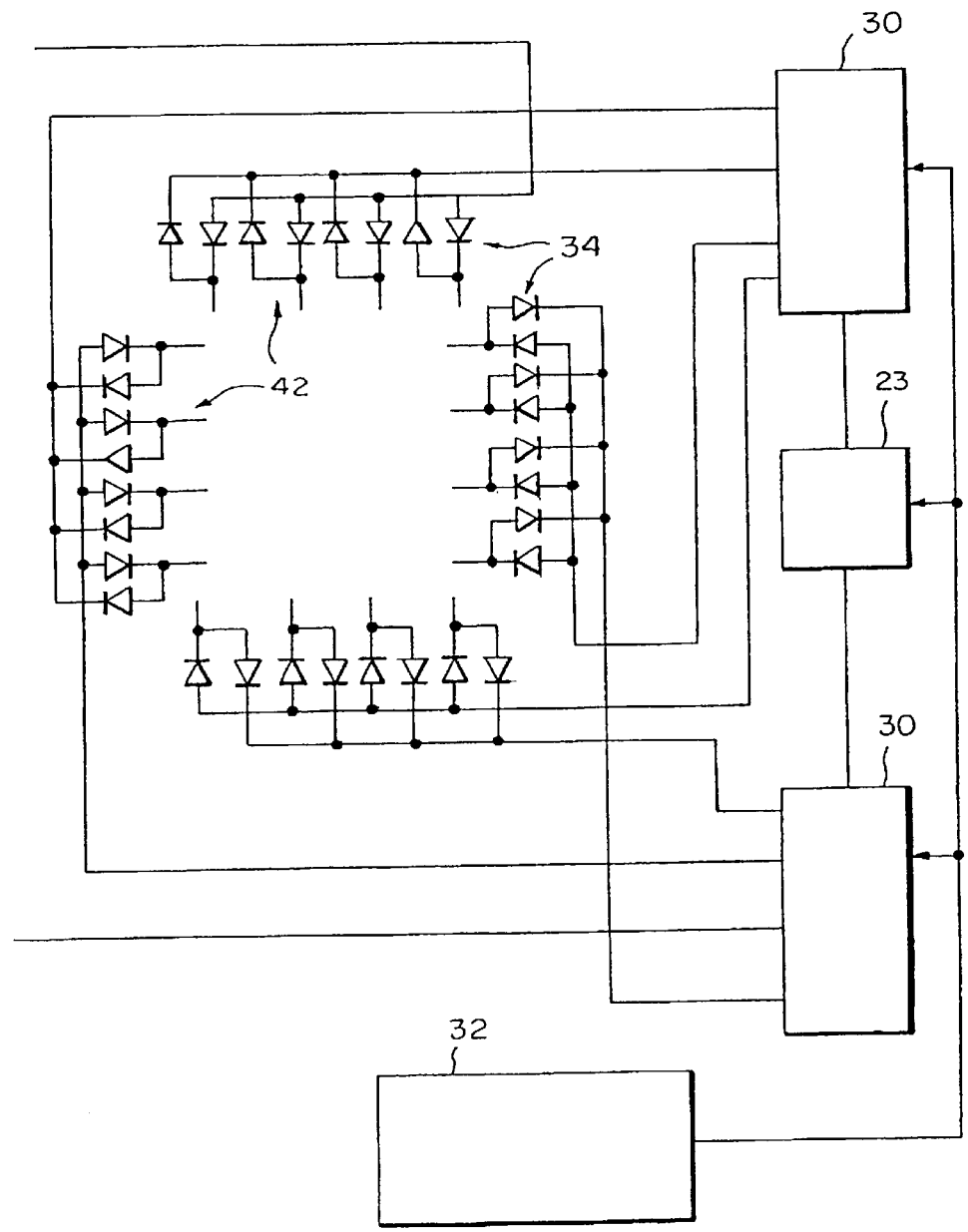
FIG. 2 is a partly schematic and partly block diagram showing an interconnection of exemplary chamber electrodes in an electrophoresis chamber which may be used in the present invention.

An exemplary laboratory instrument for POE is illustrated in FIG. 1 and a schematic view is shown in FIG. 2.

The instrument exemplified in FIG. 1 is similar to a miniature version of that described in U.S. Pat. No. 4,473,452, but differs in that the POE instrument has two sets of diodes 34 which enable bipolar operation of the discrete electrode array. The diodes 34 can be replaced by a multi-ganged relay (not shown) to provide similar electrical isolation. However, it is best to use the diodes 34 when very fast (less than 1 second) pulsing is needed.

As depicted in FIGS. 1 and 2, the miniature electrophoresis chamber 50 used in this invention measures about the size of a standard coverslip. It has electrodes 42', which are connected to diodes 34 (FIG. 2). In order to generate the desired electric fields, platinum electrodes 42' are interconnected as shown in FIG. 2. In particular, d-c power supply 28 supplies d-c power to relays 30, which are controlled by a computer 32 to connect selected outputs to the d-c power from power supply 28. Computer 32 also controls d-c power supply 28 so that the potential of the power supply can be varied. Outputs to relays 30 are connected to electrodes 42' through respective diodes 34 for each electrode.

As shown in FIG. 1, the miniature POE apparatus has a holder 52, which fits on a microscope stage. A slide 54, which holds an agarose gel, is placed into the holder and the electrodes 42 make electrical contact with the slide/gel/ cover-slip sandwich placing drops of 30% glycerol-agarose at the agarose electrical connecting wicks 44. The glycerol prevents drying out of the gel. The electrical connector 46, which is part of the holder 52, provides a link to the bipolar diodes 34 and pulsing instrumentation shown in FIG. 2.

As in the case of the instrument described in U.S. Pat. No. 4,473,452, the presently exemplified instrument generates electrical fields which are orthogonal to each other, which alternate between high and low intensities out of phase with each other according to the chosen pulsing routine as described below and which translate the molecules undergoing separation incrementally through the gel matrix in an overall direction transverse to the respective directions of the generated electrical fields. Due to the novel bipolar nature of the electrode design, it is possible to change polarities, simultaneously if desired, in addition to alternating high and low intensities without any significant electrode induced field distortions.

The determination of effective field angle by a pulsing routine rather than by placement of an electrode array permits molecular orientations (and separations) that would otherwise be difficult. As described in Example 4 below, POE has been used in DNA imaging experiments. The electrophoresis apparatus pictured in FIGS. 1 and 2 and used in Example 4 may be preferred over that of U.S. Pat. No. 4,695,548 because varying the field angle by moving electrodes as taught by conventional pulsed field electrophoresis is not practical due to microscope stage physical constraints. However, use of a POE device is not necessary to practice this invention when the molecules can be sufficiently perturbed by other means. Conventional electrophoresis using an apparatus which is about the size of a microscope slide is another preferred method for perturbing charged molecules.

Figure 3A:
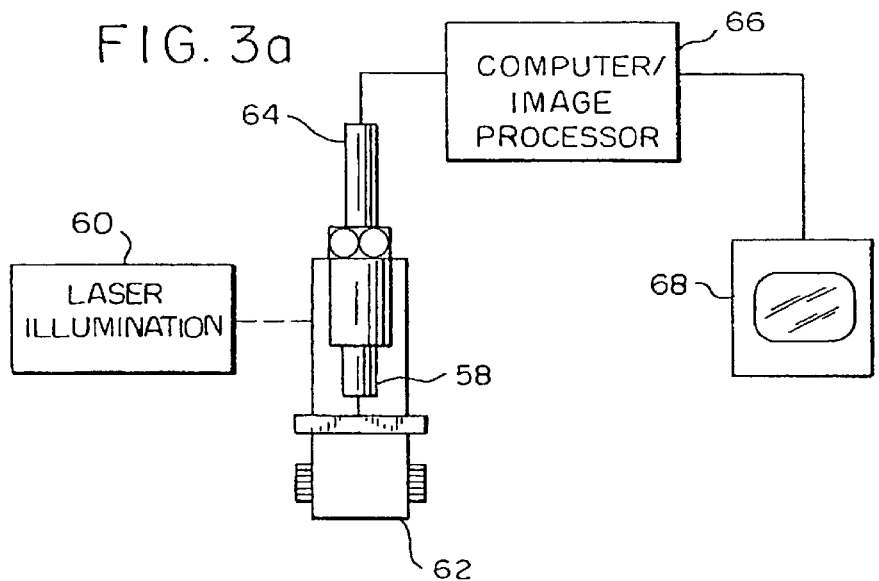
FIGS. 3A–B is a schematic illustration of the instrumentation used in the microscopic study of DNA molecules in a medium according to this invention, and a more detailed diagram showing the instrumentation for measuring birefringence.

In a preferred embodiment of this invention, a small electrophoresis chamber containing polymer molecules is placed upon a microscope slide and the polymer molecules are viewed under a light microscope. As depicted in FIG. 3(a), imaging of single molecules is accomplished with an epifluorescence microscope 62 (excitation light comes from above the sample as from laser 60) coupled to a low light level sensitive video camera 64 which is connected to an image processor 66, which in turn is connected to a video monitor 68. The use of epifluorescence microscopy here in this invention is an extension of the methodology first developed by Yanigida et al, in Application of Fluorescence in the Biomedical Sciences, (eds. Taylor, D. L. et al), 321–345 (Alan R. Liss, Inc., New York, 1986). A high powered oil immersion objective 58 is preferably used in the microscope. The key requirement is to use objectives with a high numerical aperture which gathers light effectively. A silicon intensified target (SIT) camera or a micro-channel plate detector is used to boost the light sensitivity to the point of counting photons. The image processor is a computer dedicated to digitizing, processing and storing images from the video camera. This type of image processor is known in the art. Images can be radically enhanced to bring up contrast, provide pseudocolor representation of gray levels (colors can be assigned to enhance images on an arbitrary basis, not unlike what is done with "colorizing" old black and white movies), and provide feature analysis which might include counting objects in the field of view. It is possible to view single DNA molecules stained with an appropriate chromophore, such as 4',6-diamidino-2-phenylindole dihydrochloride (DAPI), using epifluorescence microcopy.

The smallest size determination of this visualization technique is limited by microscope resolution, which, at this time, is approximately 0.1 microns or approximately 300 nucleotide bases in a DNA molecule. This length corresponds to the length of a small bacterial gene, however some DNA molecules are up to several inches in length, as is a human chromosome. Since it is possible to view several molecules in a sample simultaneously, it is also possible to measure sizes of many discrete molecules simultaneously.

An alternate way to size molecules according to his invention involves measuring molecules spectroscopically. This technique, when combined with microscopy, is particularly useful to size molecules which are too small to be imaged with satisfactory resolution and is described in detail in example 6. It also may be used for molecules of medium or large sizes. Resolution using these techniques is simply limited by signal/noise as determined by photon counting.

The size parameters which are measured according to the preferred embodiments of this invention include relaxation or stretching rates of a perturbed molecule, reorientation rate and/or rotation rate of a particle subject to perturbing forces in different direction, the curvilinear length of a perturbed molecule, and the diameter of a spherical, ellipsoidal or globular molecule. Each embodiment is based upon a mathematical relationship between the parameter which is measured and molecular size.

A first preferred embodiment involves measurement of the time required for a perturbed application of an external force is terminated. The measurement of relaxation kinetics is described in Examples 1–4. This embodiment is based in part upon principles which mathematically relate relaxation time and molecular size.

An important advantage of measuring fragment sizes using relaxation rather than by other methods, such as measuring curvilinear length, is that the DNA molecules does not need to be totally stretched out in order to obtain an accurate measurement. The measured relaxation time is independent of the degree of coil extension. This has been clearly shown for measuring DNA relaxation times using the viscoelastic technique (Massa, D. J., Biopolymers 121071–1081 (1973).

Figure 4A:
FIGS. 4A–I shows the DNA molecular conformational and positional changes when G bacteriophage molecules are subject to two sequential electric fields in different directions.
Figure 4B:
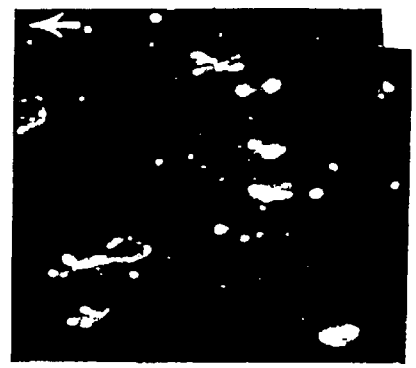
Figure 4C:
Figure 4D:
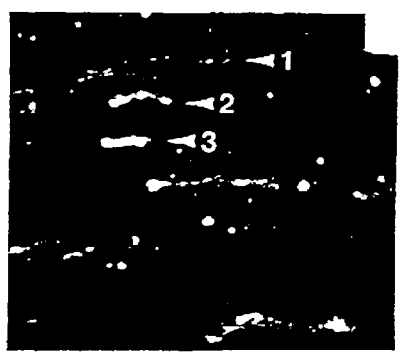
Figure 4E:
Figure 4F:
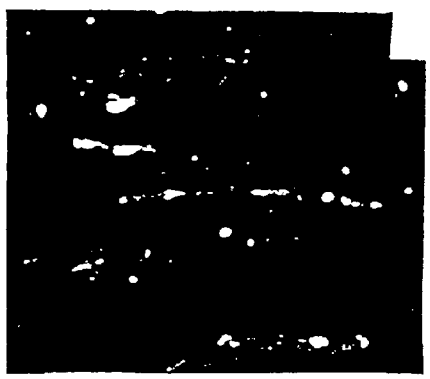
Figure 4G:
Figure 4H:
Figure 4I:
Figure 5A:
FIGS. 5A–J shows the DNA molecular conformational and positional changes during relaxation of G bacteriophage DNA molecules after electrophoresis for 600 seconds, as revealed by the fluorescence microscopy experiments described in Example 4.
Figure 5B:
Figure 5C:
Figure 5D:
Figure 5E:
Figure 5F:
Figure 5G:
Figure 5H:
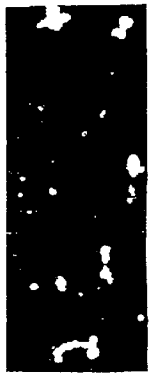
Figure 5I:
Figure 5J:

A second preferred embodiment involves measurement of the reorientation time of a molecule subject to at least one external force, for example, sequential electric fields in different directions. This is described below in Example 6 and is shown in FIGS. 4A and 5J. The principles upon which reorientation rate is based have been studied by the inventor using fluorescence microscopy/image processing. Using the process as described below in the Examples, it has been determined that during pulsed field electrophoresis, the blob train of a DNA molecule orients with the applied electric field in a very complicated manner and during this process, electrophoretic mobility is retarded until alignment is complete, e.g., until the molecule is aligned with the applied field. Upon field direction change, the blob train moves in several new directions simultaneously (i.e., the blobs appear to be moving somewhat independently). Eventually, some part of the blob train dominates in reorienting with the applied field and pulls the rest of the blobs along its created path through the gel. The time necessary for complete blob train alignment varies directly with size; i.e., a 10 mb (1 mb=1,000 kb) molecule requires one hour to reorient, while a 10 kb molecule requires only ten seconds, using similar field strengths. The phenomenon is illustrated in FIG. 4. Reorientation is measured in various ways, including by light microscopy and by microscopy combined with spectroscopic methods.

A third preferred embodiment of this invention involves measurement of the rotation time of a molecule subject to sequential electric fields in different directions. In one sense, rotation of a molecules requires a series of incremental reorientation steps, each of which causes the molecule to rotate further in the same direction, until the molecule has undergone a rotation of a specified angular increment, for example, 360°. This embodiment is particularly well suited to characterize stiff, rod-like molecules, such as small DNA molecules, which do not significantly change conformation upon application of an external force. However, large molecules also may be sized by this method if the conformation of the molecules is kept fairly constant, preferably in a rod-like or elongated conformation. This is accomplished by applying a pulsing routine which is appropriate to the size, shape and perhaps also the composition of the molecule. As a non-limiting example, molecules are rotated in the presence of sinusoidally varying electrical fields applied at 90° to each other. Stiff, rod-shaped molecules or stretched molecules are rotated about the long or short axis. Rotation about the long axis has the greatest molecular weight dependence, with rotation diffusion varying as about M3. Rotational motion of a rod-shaped molecule immersed in a gel or any other confining may be difficult if an attempt is made to simply rotate the molecule as a boat propeller rotates in water. When a gel is used, the matrix affects rotation of the molecule much as seaweed affects the rotation of a boat propeller. Thus, a pulsing routine is applied which also provides back and forth motion of the molecule, thereby facilitating rotation.

The pulsing routine may be defined by an algorithm. Generally speaking, the algorithm may depend on variables such as angle increment, time, electric field intensity, etc., and these may in turn be a function of different variables. Thus, the types of usable algorithms are numerous.

A preferred pulsing routine for this invention may be defined as follows $$\overline{E}_1(t) = E(t,\theta_i)(\hat{i} \cos \theta_i + \hat{j} \sin \theta_i)(\Delta t)$$

$$\overline{E}_2(t) = E(t,\theta_i)(\hat{i} \cos(\theta_i+\Pi) + \hat{j} \sin(\theta_i+\Pi))(\Delta t)$$

$$P_i = K_1 * \overline{E}_1(t), K_2 * \overline{E}_2(t), K_1 * \overline{E}_1,(t)$$

wherein $\overline{E}_{1(t)}$ and $\overline{E}_{2(t)}$ are electric field vectors multiplied by time (volt.sec/cm);

$E(t,\theta_i)$ is the electric field intensity in volt/cm;

$\hat{i}$ and $\hat{j}$ are unit vectors;

$\theta_i$ is the field angle, in radians or degrees, with i=1-n, where $n/\epsilon * \theta_i/i=1=2\Pi$ or 360° for a complete rotation;

$\Delta t$ is pulse length, in seconds;

t is time in seconds;

$k_1$ and $k_2$ are the number of successive identical pulses; and

P is a pulsing routine, which may be repeated.

Using the above routine, a molecule to which appropriate pulses are applied rotates about $(\theta_{i+1}-\theta_i)$ radians or degrees when each set of pulses P are initiated. Also, the molecule is translated (moves laterally) in the directions of $\overline{E}(t)$ and $-\overline{E}(t)$, thereby facilitating rotation.

In the above equation, $\Delta t$ is a constant, however, this need not be the case. $\overline{E}$ may be a function of any variable or set of variables. For example, E may be a function of total elapsed time and/or angle increment. Also, the sum of all the angular increments need not be 360°, and may be any number of partial or total rotations which provide measurements of sufficient accuracy.

A specific set of conditions for measuring the rotation rate of molecules are set forth in Example 7.

According to a fourth preferred embodiment of this present invention, a useful way to measure the size of molecules such as polymer molecules is to visualize them and measure their curvilinear length (equivalent to measuring the length of a rope) directly using a light microscope. It is shown in Example 4 below, and in FIGS. 4 and 5, that fluorescence microscopy can image single polymer molecules stained with an appropriate chromophore. Incredibly, even though the polymer diameter dimensions may only be just 20 angstroms, single molecules are easily visualized. If the molecule is stretched out and a computerized imaging apparatus is used to measure the length of the visualized molecule, the size dependence of the measurements varies as about M1. Measurements of length are particularly useful in sizing and ordering DNA fragments, such as restriction digests, as described in detail in Example 10.

A fifth preferred embodiment involves measuring the diameter of a relaxed molecule. Measurements of molecular diameter are made according to the same procedure of staining molecules, placing the molecules in a medium, etc. as the curvilinear length measurements. However, it is not necessary to perturb the molecules before measurement. Instead, the molecules are measured when they are in a relaxed state, having a spherical or elongated elliptical shape. Because the volume of a sphere is proportional to $R^3$ where R=radius, and the volume of an ellipsoid is proportioned to $ab^2$ where a is the radius of the major axis, and b is the radius of the shorter axis, resolution for this technique varies as about $M^{33}$. Molecules measured by this technique do not need to be deformable. This technique can be used for all sizes of DNA molecules and is useful for sizing large DNA molecules, which are now successfully be mounted on a microscope slide, as well as for sizing densely packed molecules.

Large molecules, such as large DNA molecules, are difficult to mount on a microscope slide without causing breakage, and the present invention addresses this problem using a novel technique, which is a further aspect of this invention. A typical human chromosome may contain a single DNA molecule stretching inches in length. Nature provides a clever packaging scheme to fit approximately six feet of DNA into a cell measuring only a few microns in diameter. However, these large DNA molecules are very sensitive to breakage. For example, solutions of large DNA molecules cannot be poured, pipetted, or stirred without breaking molecules. Thus, working with large DNA molecules can be very difficult. Some years ago the inventor developed a gel based method of preparing large DNA molecules without breakage that also permitted biochemistry using intact molecules, (see U.S. Pat. No. 4,695,548). The procedure is called the insert method and works as follows. Cells are washed and mixed with low gelling temperature agarose kept at 37° C. The cell-agarose mixture is pipetted into a mold (to produce small blocks to fit into the wells of a slab gel) and allowed to gel. The resulting blocks or "inserts" as they are named are then placed into a lysis solution containing EDTA, protease and detergent. The lysis solution diffuses into the insert, lyses the cells and renders intact naked DNA molecules stripped of their associated proteins. The DNA molecules do not diffuse out of the because very large coils are generally unable to diffuse.

The present invention provides the discovery that DNA molecules up to at least one megabase (1 megabase=1 million bases=660×10$^6$ daltons) when suspended in liquid agarose are protected against shear when mounted on a microscope slide. However for molecules larger than 2 or 3 megabases or for situations where the integrity of 100% of the molecules must be ensured, this procedure is not effective.

A sixth embodiment of the invention remedies the above-mentioned problem involved in placing molecules larger than 1 megabase on a microscope slide. The inventor developed a protocol using a condensation agent to collapse gel bound DNA (as obtained from inserts) into small shear resistant balls, that can be unfolded once mounted, with the addition of an ionic compound, for example, a salt such as sodium chloride or magnesium chloride. Preferably, the condensation agent is spermine. The spermine protocol, which is described further in Example 10, permits the mounting of DNA molecules of even the largest known DNA molecules, and feasibly even larger molecules, without any detectable shear mediated breakage. While the use of spermine is preferred, other suitable materials for collapsing the molecule include any material which can cause a particular molecule to collapse, e.g., any condensation agent which causes molecules to preferentially solvate themselves. Examples of such materials include, but are not limited to spermidine, alcohol and hexamine cobalt.

A seventh preferred embodiment of the invention relates to a specific application of the above embodiments of this invention to map DNA molecules using restriction enzymes. The previously known method for constructing a restriction map is to incubate DNA with a restriction enzyme and size separate the resulting fragments using conventional gel electrophoresis or pulsed electrophoresis. Size separation provides information on the number and size of the fragments but no information on the relative location of fragments or cutting sites on the uncut DNA molecule. By using the microscope to image molecules undergoing digestion by restriction enzymes, (1) size resolution is accurately determined by measuring relaxation kinetics, (2) positioning of fragments relative to each other can be determined, and (3) only one molecule needs to be digested (however, many molecules can be image processed in parallel). One limitation is space on the sample holder.

In brief, restriction mapping using the microscope involves mounting large gel embedded DNA molecules on a microscope slide, stretching them to some extent (it is not necessary that the molecules be completely stretched), and then inducing cleavage. The fragment positions are noted and their sizes are determined using the methods outlined in embodiments one to four, using visualization or spectroscopy. A preferred embodiment of this aspect of the invention is described in detail in Example 11.

The first step in map construction is to determine the number of cleavage sites within a molecule by examining histograms of cuts per molecule and corresponding cleavage patterns. Because the rates of enzymatic cleavage by different restriction enzymes are variable, careful adjustment of the timing is critical. Cleavage preferably occurs only after molecular fixation was complete because premature reactions would disrupt attempts to order fragments. As a non-limiting example, this timing problem can be solved by this invention by premixing the agarose-DNA solution with restriction enzyme, at 37° C. and triggering the reaction by diffusing Mg$^{2+}$ into the viewing field, without disturbing the gel. All possible cleavage sites did not appear simultaneously; instead, cuts usually appeared within 5 min. of each other. A typical mounted sample may contain approximately 3 to 5 molecules within a single viewing field, and overall roughly 50 to 95% of them showed evidence of one or more cuts.

The next step can be used to determine the size of the resulting restriction fragments. For this purpose there are developed two complementary approaches according to this invention, one based on relative fragment fluorescence intensity and the second on apparent relative length measurements.

Figure 10A:
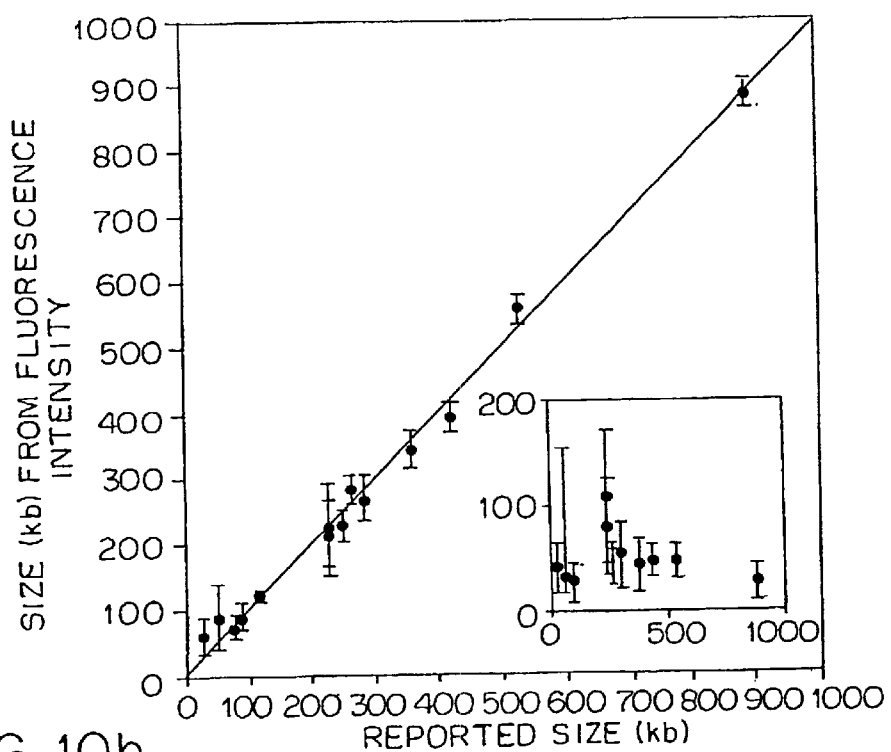
FIGS. 10A–B shows optical mapping sizing results for Not I endonuclease restriction fragments from *S. cerevisiae* chromosomes I, V, VIII, XI, XIII, and XVI calculated as described, plotted against published results. The diagonal line is for reference. Typical fragment images are shown in this figure. See example 13. The inset shows the estimate of population standard deviation (kb). Error bars represent 90% confidence (7) on means (main graph) or standard deviation (inset). 10A shows the relative intensity determination of fragment sizes. 10B shows the relative apparent length determination of fragment sizes.

Microscope-based intensity measurements are difficult to perform because of their dependence on many variables, including camera control and illumination intensity. By calculating the relative intensity of two fragments (from the same parental molecule), one of the fragments serves as an internal intensity reference for the other. Relative intensities are converted to kilobases by multiplying by the known or independently determined chromosome size. FIG. 10A shows the sizes determined for a series of yeast chromosome Not I restriction fragments measured optically and plotted against published values derived from electrophoresis-based measurements. Points close to the diagonal line are in good agreement. Excluding the two short fragments less than 60 kb and the low-resolution 8-bit chromosome 5 and 8 data, the pooled SD was 36 kb (FIG. 10A, inset). The average of the coefficients of variation was 16%, which is comparable to routine pulsed electrophoresis size determinations. The correlation with published results is excellent: the average of the relative errors is 5%, whereas the published errors average 4%. Due in part to the intensity normalization procedure, the precision becomes lower for very small fragments, and size agreement is poor for the measurements of the 30- and 55-kb DNAs. Fluorescence intensity measurements report a size of these fragments almost twice that of the above values.

One test of the validity of relative fluorescence intensity measurements is to monitor the constancy of fragment intensities over a usable range of molecular relaxation conditions. This requirement is most critically tested when restriction fragments differ greatly in size. Intensities are discovered to remain relatively constant over a wide size range despite a three- to four-fold change in measured molecular length. This beneficial effect can be attributed in part to the mild fixation conditions, so that Brownian motion can vibrate the elongated coil along the z-axis; this motion is clearly observed on the live video monitor as digestion proceeds. By averaging frames over a 1–5 interval, most of the DNA which is observable moves through the focal plane and within the gel pores.

Figure 10B:
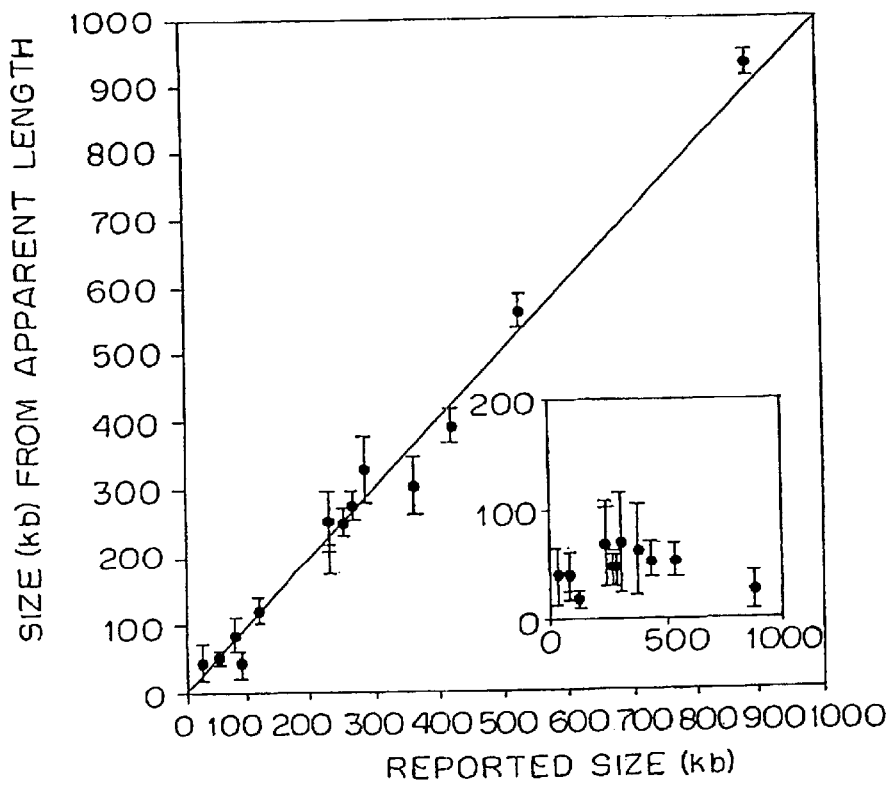

For measurement of the relative apparent length, each of the gel-embedded restriction fragments is assumed to have equal coil density, on the average. Relative apparent lengths can be converted to kilobases by multiplying by the chromosome size. Then, the apparent lengths of restriction fragments can be averaged obtaining accurate sizes from as few as four molecules. Relative determinations of apparent length can be standardized against the same set of restriction fragments as in the fluorescence intensity measurements, and these results (FIG. 10B) show a similar average relative error of 16% (excluding the 30- and 90-kb fragments). The pooled SD was 47 kb (FIG. 10B, inset): the average of the coefficients of variation was 29%, in these non-limiting examples.

Length measurements can be used to evaluate fragments that are out of focus, e.g., when out of focus images distort intensity-based measurements. Additionally, size determinations of small fragments are better by length than by intensity.

Single Molecule Sizing Methodologies. Optical mapping is dependent on methodologies for sizing single molecules and construction of restriction maps of higher resolution and precision can be provided by such methods of the present invention. As non-limiting examples, five single molecule sizing methods are provided, including apparent relative length, fluorescence intensity ratio, relaxation in a gel, baseline, and OCM (optical contour mapping). These can be classified into two groups: techniques that require molecular perturbation or external force and those that require none.

Non-perturbation sizing techniques such as measurements of fluorescence intensity of single molecules and apparent length measurements are convenient to use because they do not require a sophisticated microscope mounted chamber and attending controlling electronics. Additionally, non-perturbing sizing techniques are also well suited for parallel measurements. Despite some of these advantages for the non-perturbing class, the perturbation-based sizing techniques of the present invention have great utility for characterizing polymer molecules and mapping chromosomes, as provide higher precision and resolution.

Figure 12:
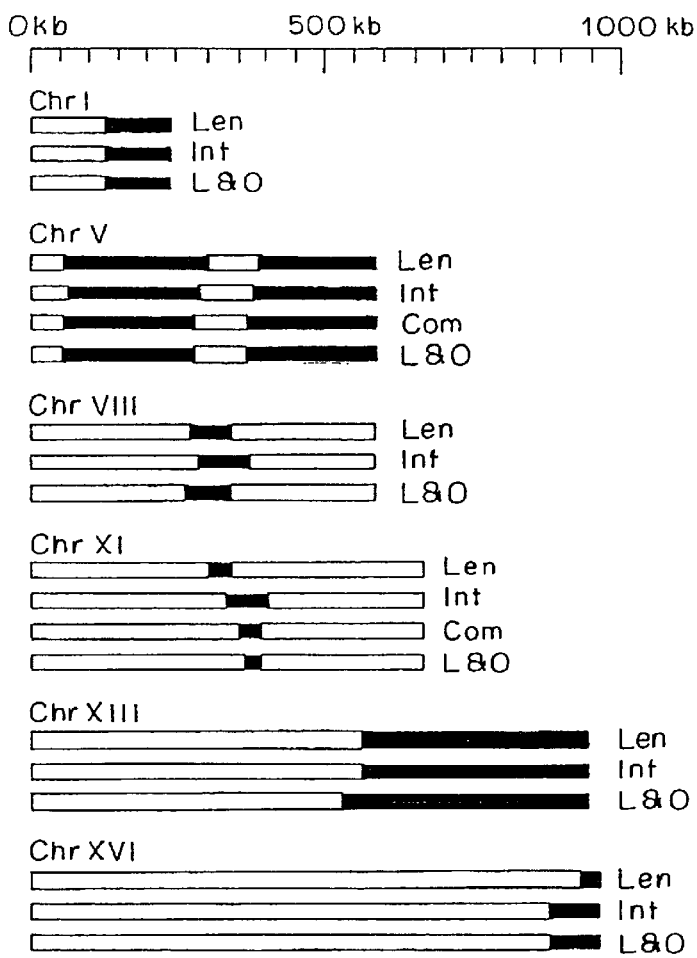
FIG. 12 is a graphical comparison of Not I endonuclease restriction maps of optical mapping results of *S. cerevisiae* chromosomal DNA molecules with published restriction maps (L&O). Maps were constructed from length (Len), intensity (Int) or a combination of both (Com). Bar lengths for the optical mapping data are proportional to the means plotted in FIGS. 10A–B, and typical images are shown in FIGS. 13A–F.

FIG. 12 illustrates three types of ordered restriction maps produced by optical mapping of the present invention as compared with published restriction maps. Additionally, FIGS. 13A–F, shows selected corresponding processed fluorescence micrographs of different yeast chromosomal DNA molecules digested with Not I. These images clearly show progressive digestion by the appearance of growing gaps in the fixed molecules. From such data, the order of fragments can be determined by inspection of time-lapse images obtained every time interval, e.g., 0.07–200 s, or any range or value therein, e.g., 1–30 s. Because observed molecules tend to move and can sometimes be confused with other molecules, inspection of a "cutting sequence" or "cutting movie" simplifies deconvolution of molecule-molecule interactions. Agreement is expected to be, and has been found to be excellent, between the optical (length or intensity) and the electrophoresis-based maps. The third type of restriction map (e.g., Com. FIG. 12) combines length- and intensity-derived data; small restriction fragments (100–20, or any range or value therein, e.g., <60 kb) can be sized by length, whereas intensity measurements can provide the remaining fragment sizes needed to complete the maps.

Figure 13A:
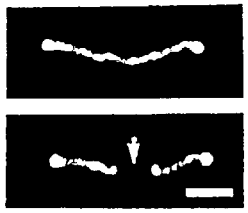
FIGS. 13A–F shows typical fluorescence microscopy images of *S. cerevisiae* chromosomal DNA molecules stained with DAPI and embedded in agarose gel during Not I restriction endonuclease cleavage. Chromosomal DNA molecules were prepared and fixed as described in example 13 and cited references. Images were background corrected using a smoothed and attenuated background image, smoothed, and stretched, using 16-bit precision. Images show Not I restriction digestion evolution, with arrows highlighting cut sites. Intervals are timed after addition of Mg+2. 13(A) Ch. I (240 kb), 20 and 60 sec; 13(B) Ch. XI (675 kb), 500, 880 and 1160 sec; 13(C) Ch. V (595 kb), 200, 240, 520 sec; 13(D) Ch. VIII (595 kb), 440, 1220 and 1360 sec; 13(E) Ch. XIII (950 kb), 100 and 560 sec; 13(F) Ch. XVI (975 kb), 460 and 560 sec. Bars, 5 µm. A 100× objective was used to image results in panels (13A–D) and a 63× objective was used for panels (13E and F).
Figure 13B:
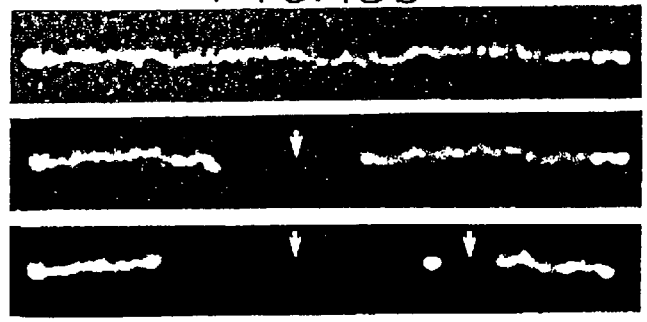
Figure 13C:
Figure 13D:
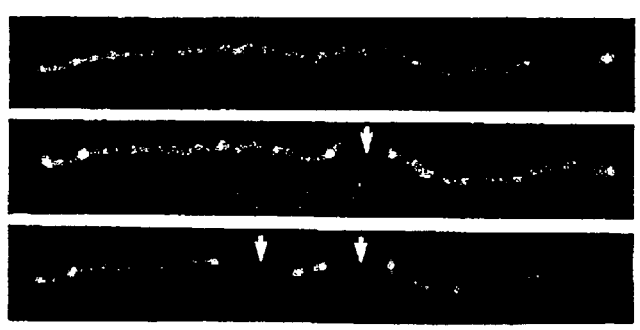
Figure 13E:
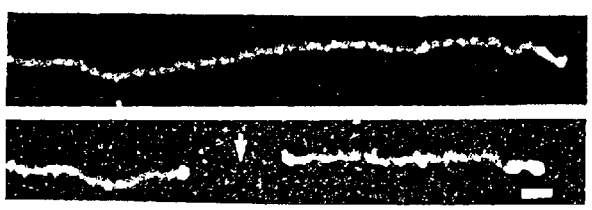
Figure 13F:
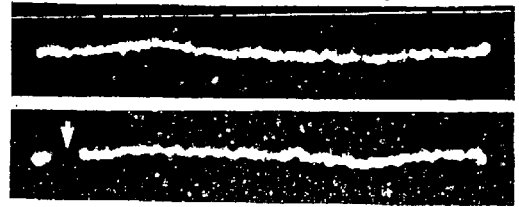

FIG. 13A shows a non-limiting example of images of a relatively small yeast chromosome (240 kb) that was elongated and fixed to roughly one-third of its contour length. Because chromosomal DNA molecules less than about (e.g., 200–500, or any range or value therein) relax quickly in molten agarose, trapped in an extended form at lower temperatures to hasten gelation. Note that molecular relaxation processes can produce a gap and form balls at the cut fragment ends, whereas the parental molecule ends remain essentially fixed. Molecules in this size range can form disproportionately large balls at parental molecule ends. Fragment relaxation motions at cut sites can be observed to re-trace the original gel pores occupied by uncut molecules as predicted by polymer reptational theory (FIGS. 13A–F, 14 and 15). These molecular characteristics can be conserved regardless of molecular size and the number of cut sites. Fragments, approximately less than about 50–100 kb, e.g., 90 kb, frequently relax completely to form balls as shown in FIGS. 13B, C and F and 15. Restriction digestion results that vary in fragment number, size and order can be used to readily characterize a mixture of similarly sized but different molecules. FIGS. 13C–D, and FIGS. 13E and F, show results obtained from two such chromosomal mixtures. In the first example, a small distal restriction fragment on chromosome 5 (FIG. 13C) serves to differentiate it from chromosome 8. The second example (FIGS. 13E and F) shows that a single cut can differentiate similarly sized molecules, given sufficient resolution. These shear-sensitive, megabase sized DNA molecules can be mounted with minor breakage and mapped by means of a lower power (e.g., 40–80×, e.g., 63×, as compared with 80–500×) microscope objective.

Figure 14:
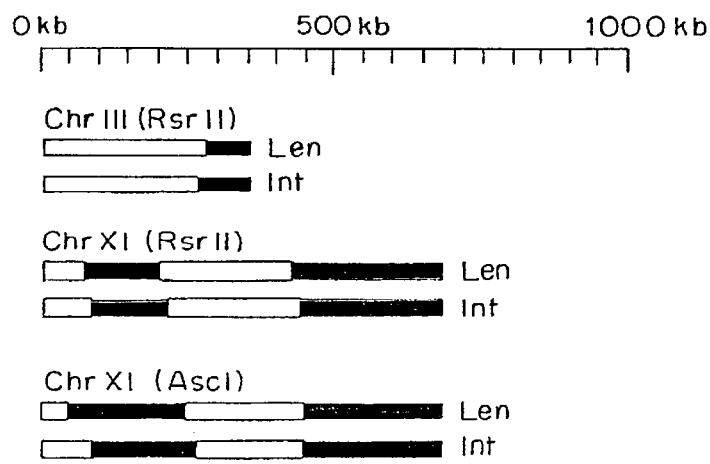
FIG. 14 shows optical mapping results from Rsr II and Asc I endonuclease restriction digest of *S. cerevisiae* chromosomes III and XI. Maps were constructed from fully cut length (Len) or intensity (Int) data, and refined using partial cut length. Bar lengths are proportional to the calculated means, and typical images are shown in FIG. 15. Number of cuts was determined as in FIG. 7.
Figure 15A:
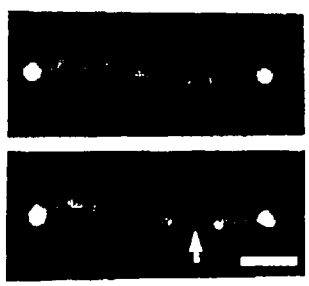
FIGS. 15A–C shows fluorescence microscopy images of *S. cerevisiae* chromosomal DNA molecules stained with DAPI and embedded in agarose gel during Rsr II or Asc I restriction endonuclease cleavage. Chromosomal DNA molecules were digested and analyzed as in FIG. 13. Images show restriction digestion evolution, with arrows highlighting cut sites. 15(A) Ch. III, Rsr II, 1100 and 1820 sec; 15(B) Ch. XI, Rsr II, 20, 600, 920, 1060 sec; 15(C) Ch. XI, Asc I, 1160, 1500, 1780, 1940 sec. An isoschizomer to Rsr II, Csp I, was also used and gave identical results. Bar, 5 µm.
Figure 15B:
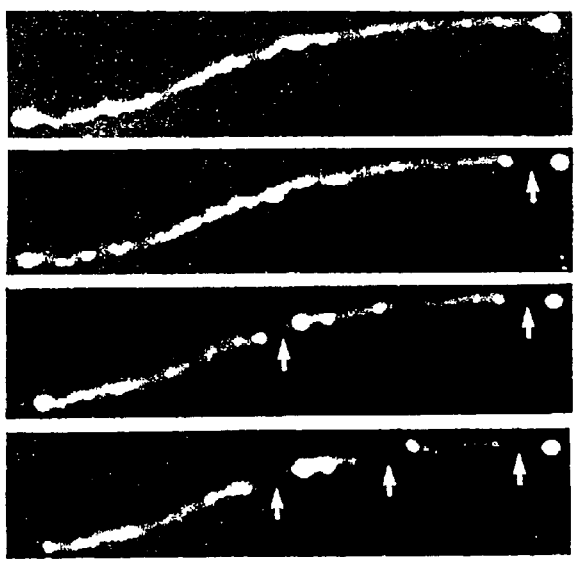
Figure 15C:
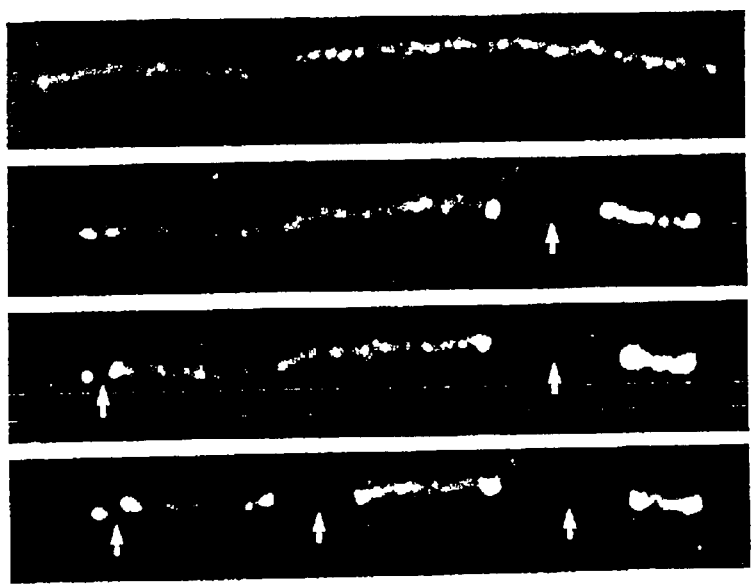

FIGS. 14 and 15 show an ordered restriction map (and corresponding fluorescence micrographs) created from a Csp I digestion of chromosome 9 by optical mapping as compared to maps created by pulsed-field gel electrophoresis (PFGE) and hybridization with a series of genetically mapped sequences. Chromosomes 3 and 11 are as known in the art. To avoid possible prejudicial selection and processing of image data, optical maps can be made and then checked with electrophoretically derived data. The overall agreement between the optical and pulsed electrophoresis maps is expected to be and found to be generally excellent.

Large-scale maps are rarely made without any errors. Maps created by optical mapping may contain some errors that stem from incorrect fragment number determination or from the stated limits on precision of our fragment-sizing methods. DNAs that have nearly symmetric maps cannot be optimally averaged to improve resolution unless one end is identified, so that map polarity must be established through ancillary means. Given expected levels of sizing precision, fragments can be detected above 10, 20, 31, 40, 50, 60, 70, 80, 90, 100, 151 or any range or value therein.

Optical mapping of this invention can be extended to mammalian genomes by technical advances that permit the detection and quantitation of restriction fragments (300–100,000, or 500 to 10,000 bp or any range or value therein) generated by frequent-cutting enzymes. Ordered contigs of well-characterized fragments can then be constructed from high-resolution, ordered restriction maps created from randomly sheared genomic DNA, e.g., 200–2000 kb in size or any range or value therein. YACs or cosmids can also be similarly analyzed and compared with the genomic map, to facilitate ordering. Engineering changes in chamber design, sample handling, image analysis, and informatics provide a high throughput methodology that is capable of rapidly mapping entire genomes and, more importantly, extending knowledge of sequence information to populations of individuals rather than to a prototype of each organism.

An eighth preferred embodiment of this invention relates to mapping nucleic acid sequences using hybridized probes. With this technique, a nucleic acid, a probe (a characterized nucleic acid) and under certain circumstances, a recombinational enzyme, are combined in a matrix. The probe may be of any practical length and may be labeled with any suitable labeling agent. If a recombinational enzyme is used, (e.g., if the probe is not capable of invading the target molecule without the use of a recombinational enzyme) it may be any suitable enzyme, for example, one known in the art for conventional labeling of DNA probes. As a non-limiting, specific example, a useful recombinational enzyme is recA.

Hybridization can be initiated by any suitable means, for example, by diffusing ATP and magnesium ions into the microscope slide.

Probes can be hybridized to a target molecule and visualized in at least two different ways. First, the probe may be visualized directly if it is sufficiently large. For example, a probe larger than 1 kb probably can be visualized using microscopy equipment which is currently available. Second, a chromophore, or other suitable labeling agent can be attached to the probe and can be detected visually or spectroscopically. For example, Texas Red or rhodamine, as well as other chromophores, may be used.

After the probe has been hybridized to the target molecule, there are at least two preferred ways to map the position of the probe. However, other methods are also within the scope of this invention. As a first preferred alternative, the curvilinear length of the target molecule can be measured. When a light microscope is used, fluorescence intensity measurements can be used to locate and quantify linear regions which are not totally stretched out. The position of the probe is located based upon its characterizing feature, e.g., chromophore, radioactive tag, and/or size. As a second preferred alternative, a target molecule is cut with restriction enzymes and all of the fragments are sized and measured by the methods of this invention. The location of the hybridized fragment is determined by one of the methods described above, e.g., by direct visualization of the molecule or by microscopy combined with spectroscopic technique. All of the fragments are sized, and the distance from the labeled fragment to either end of the target molecule is then easily calculated. The exact position of the probe on a particular restriction digest can be mapped with the addition of a new enzyme for further digestion, and these fragments can then be mapped visually.

A preferred approach to optical mapping of the present invention is imaging stained, single, deproteinized DNA molecules during restriction enzyme digestion allowing direct, ordered mapping of restriction sites. In brief, a flow field (or other type of field) is used to elongate DNA molecules dissolved in molten agarose and fix them in place during gelation. The gelation process restrains elongated molecules from appreciable relaxing to a random coil conformation during enzymatic cleavage. A restriction enzyme is added to the molten agarose-DNA mixture and cutting is triggered by magnesium ions diffused into the gelled mixture (mounted on a microscope slide). Cleavage sites can be visualized as growing gaps in imaged molecules. The resulting fragments are sized in two ways: by measuring the relative fluorescence intensities of the produces, and by measuring the relative apparent DNA molecular lengths in the fixating gel. Maps can be subsequently, constructed by recording the order of the sized fragment; averaging a small number of molecules rather than utilizing only one improves accuracy and permits rejection of unwanted molecules. Optical map production is very rapid because of the combination of restriction fragment ordering in real time with fast accurate sizing techniques. Optical mapping this provides a powerful new technology for rapidly creating ordered restriction maps of lower or higher eucaryotic chromosomes or YACs, without the need for analytical electrophoresis, cloned libraries, probes, or PCR primers. Incremental technical improvements should enable the rapid high resolution mapping of mammalian chromosomes and ordering of YACs.

In optical mapping, in which stained, single, deproteinized DNA molecules are imaged during restriction enzyme digestion to allow direct, ordered mapping of restriction sites. To briefly describe the steps involved in optical mapping, a flow field (or, in principle, an electrical or other field) is used to stretch out DNA molecules dissolved in molten agarose and fix them in place during gelation. The gelation process restrains elongated molecules from appreciably relaxing to a random coil conformation during enzymatic cleavage. The activity of a restriction enzyme already present in the agarose-DNA mixture is triggered by magnesium ions diffused into the gelled mixture (mounted on a microscope slide). Cleavage sites are visualized as growing gaps in imaged molecules. The resulting fragments are sized in two ways: by measuring the relative fluorescence intensities of the products and by measuring the relative apparent DNA molecular lengths in the fixating gel. Maps are then constructed by simply recording the order of the sized fragments. Averaging a small number of molecules rather than utilizing only one improves accuracy and permits rejection of unwanted molecules or fragments. Optical map production is very rapid because of the combination of restriction fragment ordering in real time with fast accurate sizing techniques. This approach opens up a powerful new technology for rapidly creating ordered restriction maps of lower eucaryotic chromosomes or YACs, without the need for analytical electrophoresis, cloned libraries, probes, or PCR primers.

Optimization of optical mapping for genomic analysis includes alternative molecular fixation techniques; new molecular sizing techniques that do not rely on analytical electrophoresis; new image processing approaches, tailored to mapping needs, and 4) new approaches for restriction map construction, which alternatives are now provided by the present invention. These efforts are described in the following subsections.

(i) Gel fixation and mechanics of DNA relaxation under tension and cleavage: A single large DNA molecule 200 nm long (600 kb) is a random coil in solution which can be visualized as a loosely packed ball averaging 8 nm across (61). Optical mapping begins with stretching out such a DNA molecule and fixing it in place to inhibit rapid relaxation, prior to imaging by light microscopy. The fixed molecule must lie within a shallow plane of focus for successful imaging. Elongated molecules in a gel behave mechanically like a stretched spring: fixed molecules are under tension which is released during coil relaxation to a random conformation. DNA molecules embedded in agarose gel, have been modeled during electrophoresis, as a series of connected pools of coil segments under tension with each other, and calculates that the force ($f_i$) associated with the free energy change of shuttling coil segments between pools is given by:

$$f_i = 3\ kT/(2\ n_i b)((a^2/n_i b^2) - 1) + (kT/b)1\ nC$$

where k is the Boltzmann constant, a is the gel pore diameter, $n_i$ is the number of associated coil segments, b is the coil segment length, T is the temperature and C is a constant relating to coil segment structure. This result shows that the tension developed between pools is inversely related to the number of segments contained within a pore volume. It follows that a stretched-out, elongated molecule is under more tension than a compact, relaxed one.

Large DNA molecules are conveniently stretched out in molten agarose by flow forces and then rapidly fixed in place by agarose gelation, without applying electrical fields. Experimentally, the kinetics of gelation are controlled by temperature, and optimization of the annealing conditions. for our analysis, DNA coils must be critically stretched: too much and the molecule becomes difficult to image; too little, and there is insufficient tension to reveal cut sites. Excessively stretched molecules present too little fluorochrome per imaging pixel, so that measured molecular intensities approach background values. Additionally, the fixation process has to be gentle enough to permit some coil slippage to reveal cut sites. Taking these and other considerations into account, one can practically optimize fixation conditions to produce molecules spanning approximately 20% of their curvilinear contour lengths.

Restriction Digestion of Single Molecules Including Optical Mapping detects restriction enzyme cleavage sites as gaps that appear in a fixed molecule while fragments relax to a more random conformation. Since the rates of enzymatic cleavage by different restriction enzymes are variable (64), careful adjustment of the timing is critical. Cleavage should occur only after molecular fixation is complete because premature reactions disrupt attempts to phase fragments. This timing problem can be solved by premixing the agarose-DNA solution with restriction enzyme, at 37° C., and triggering the reaction by diffusing magnesium ions into the viewing field, without disturbing the gel. Aside from gaps, cleavage is also signaled by the appearance of bright condensed pools or "balls" of DNA on the fragment ends at the cut site. These balls form shortly after cleavage and result from coil relaxation which is favored at ends. This pooling of segments is useful in map making because it helps to differentiate out-of-focus segments, that might appear as gaps, from actual cuts. Cleavage is scored reliably by both the appearance of growing gaps and enlarging bright pools of segments at the cut site.

Map Construction—Fragment Number Determination

As described herein, large scale restriction maps have been constructed primarily from electrophoretically derived data. In contrast, the present invention involves as the first step determining the number of cleavage sites within a molecule. The cut sites within a molecule tend to appear at irregular times after $Mg^{2+}$ addition. All possible cleavage sites may not appear simultaneously; instead, cuts usually appear within 5 minutes of each other, e.g., under the conditions described herein. The extent of digestion depends on a number of factors including both the fragment number and size. The correct number of cleavage sites may be determined by histogram analysis of partial digestion results (molecules are sorted, binned and counted by the number of cuts). Typically, 10–20 molecules suffice for this analysis, and the bin containing the largest number of cut sites whose molecules can be properly averaged by intensity and length measurements for size, can provide the correct number.

Fragment Sizing by Relative Intensity

The second step can be to size the resulting restriction fragments. For this purpose two complementary approaches can be used, one based on relative fragment fluorescence intensity and the second on apparent relative length measurements. However, neither approach may provide absolute values, but each can be standardized readily. The gel fixation technique described above also produces a natural substrate for intensity measurements since an entire molecule can be brought into focus. Gel fixation is able to flatten molecules spanning as much as 250 microns. Segments of molecules that are out of focus cannot be used for intensity measurements because their intensities are not proportional to mass in any simple way. A relevant observation here is that when an elongated molecule substantially relaxes, most of its mass moves out of focus, as expected, since the hydrodynamic diameter of a fully relaxed 700 kb DNA molecule in fluid is 8 microns while the depth of focus used for imaging molecules under the microscope is approximately 0.2 micron.

The absolute fluorescence intensity of a DNA fragment in the microscope is determined by any one or more of many variables, such as the camera gain control and lamp brightness, and therefore is not a desirable quantity to measure. By calculating the relative intensity of two fragments (from the same parental molecule), the fragments are allowed to serve as an internal intensity reference for the other. Relative intensities are converted to kb by multiplying by the known or independently determined chromosome size.

Other Methodologies for Sizing, Manipulating and Characterizing Single DNA Molecules Mapping Known Sequences Using Optical Mapping According to the present invention, specific sequences can be localized on single DNA previously proposed using RecA protein to D-loop chromophore-labeled homologous sequences into large target DNA molecules, followed by optical mapping, to accurately position this complex. However, with the development of the Achilles heel (66) technique and especially RARE (67, 68), a RATE technique which uses the RecA-probe-target complex to block EcoRI methylase action can also be used in methods of the present invention. Removal of the complex leaves a target molecule vulnerable to EcoRI cleavage at only the unmethylated site(s). Obviously, the RARE technique can cleave DNA at any location, given known sequences. Developed a type of high resolution FISH, since the target is a stretched-out naked DNA molecules instead of chromatin.

Figure 8A:
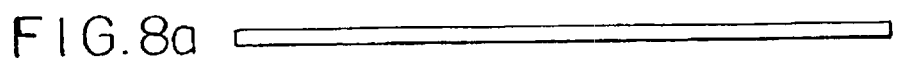
FIGS. 8A–H shows some restriction fragment relaxation modes for a singly cleaved, gel-fixed, elongated molecule. Horizontal arrows indicate direction of relaxation. Relaxation modes illustrated 8A fixed molecule before cleavage, 8B–E possible relaxation modes producing detectably cleaved molecules, and 8F–H relaxation modes producing undetectably cleaved molecules.
Figure 8B:
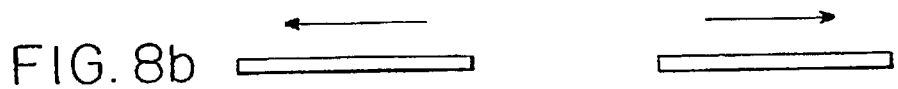
Figure 8C:
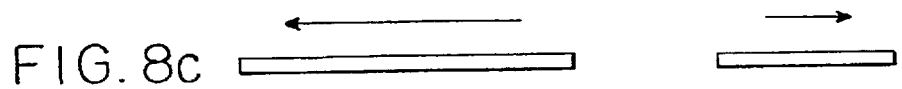
Figure 8D:
Figure 8E:
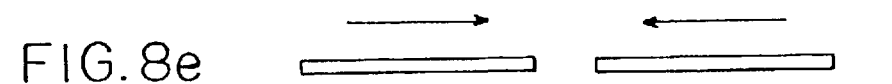
Figure 8F:
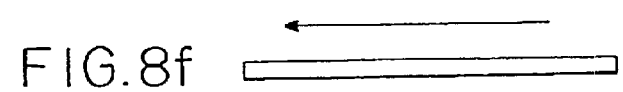
Figure 8G:
Figure 8H:

Optical mapping can be combined with RARE to create high resolution maps of lower eucaryotic chromosomes, or YACs. FIG. 8 shows results of cleaving yeast chromosomal DNA molecules. Oligonucleotides containing 50 bp from the yeast LEU2 and ERG16 genes were synthesized and used for RARE analysis on the microscope. Shown in FIG. 8A is a RARE mediated cleavage of *Candida albicans* Chromosome 5 DNA using an ERG16 oligonucleotide (69). Comparing the optical mapping data obtained from intensity ration in RARE mediated cleavage of *S. cerevisiae* Chromosome III, where fragments of 110 and 235 kb were obtained (the fluorescent intensity ratios of five molecules were binned and averaged), electrophoretically derived data yield 100 and 245 kb fragments. The published map for *Candida albicans* that is electrophoretically derived produced 180 and 1020 kb sized fragments compared to the optical mapping data of 250 and 950 kb; six molecules were averaged for this optical mapping.

RARE, combined with optical mapping, according to the present invention provides a very powerful combination for rapid restriction mapping of the human genome. RARE can be used to first excise specific mammalian genomic regions, which are purified using pulsed electrophoresis. Then, e.g., optical mapping can be used to create a restriction map for the defined genomic region.

Using Single Molecule for Sizing

Sizing Molecules by Coil Relaxation Dynamics

Fluorescence microscopy has been used to study the conformational dynamics of single DNA molecules during gel electrophoresis (53, 59, 70). Studies, both experimental and theoretical, of DNA conformation during gel electrophoresis show that a DNA molecule stretches out to form long hooks, which relax back to a compact conformation, in a cyclically occurring fashion (19, 53, 63, 71). Hook formation can be used to stretch DNA molecules out so that when the perturbing electrical field is shut off, relaxation kinetics of single molecules can be quantified by simply imaging them and measuring length changes. This measurement is similar to stretching out a spring, releasing it and monitoring the recoil kinetics by watching it shrink back to a relaxed coiled state. Traditionally, the viscoelastic technique (61) has been used to measure relaxation time (τ) so that molecular weights could be determined. However, a severe limitation is imposed on such molecular weight determinations, only the largest molecules in solution can be sized; a spectrum of sizes cannot be measured.

Parallel measurements can be made using molecular imaging techniques (e.g., fluorescence microscopy), and size distributions can be determined since the conformational dynamics of each molecule is measured separately. There is another compelling reason for studying relaxation kinetics: the associated relaxation time (τ) are strongly size dependent, with τ proportional to (molecular weight)$^{1.5-3}$, so that size discrimination is excellent. It surpasses any other sizing technique with the exception of sequencing. The determined size dependence will vary with the chosen relaxation mode.

The fast coil relaxation times that correspond to Zimm-Rouse relations (72, 73) normally encountered in solution can be initially measured. In a gel matrix, a stretched out DNA molecule with length L(t) (this is actually the length of the primitive tube) will relax as $<L(t)>=A\exp(-t/\tau)+<Le>$ (74, 75), where τ is the relations time, t is time and the brackets represent an ensemble average. L(t) is not the molecular contour length, but it can be interpreted here as the apparent molecular length as imaged by the microscope. Le is the equilibrium molecular tube length and is measured as a plateau region in an exponential decay. L forms the basis of the "Baseline" sizing methodology, as discussed herein.

Measurements of fast coil relaxation times are simple to carry out. Large DNA molecules, stained with ethidium bromide, are embedded in 1% agarose and mounted on a epifluorescence microscope, equipped with a SIT camera (a low light level sensitive device) and interfaced to an imaging board set contained within a computer. Electrodes in the microscope chamber are pulsed so that molecules form hooks, and their lengths are measured automatically during relaxation by a special program written in NIH image (Wayne Rasband) macroprogramming language. The relaxation of the DNA molecules starts when the applied field is shut off. Single exponential relaxation times are calculated for a series of yeast chromosomal DNAs and are graphed as shown in FIG. 9 (47), as a In-In plot versus size (a Mark-Houwink plot). The slope of this line gives the molecular weight dependency for τ, the relaxation time (τ)=constant (size)$^{1.45}$ (kb).

Sizing DNA Molecules by Baseline Measurement. Typical DNA relaxation plots, as apparent length versus time, provide plotted points which are averages of 4 relaxations. Such a plot shows that the measured length decreases in an exponential fashion and importantly that the molecule does not fully relax to a spherical random conformation. Instead, the quasiequilibrium structure is a thickened, short rod-like object, which signals an end of the exponential decay, and its length is the baseline for the plot. Additionally, very slow relaxation processes are still happening, but they are of a different nature and time scale, which could be proportional to mass$^3$. Within the time scale used (e.g., hundreds of seconds), length measurements settle down to an equilibrium value which is termed the "baseline". Baseline values vary linearly with DNA size and are very reproducible. Thus, a relaxation measurement yields sizes in two ways: 1) by determination of the relaxation time, τ, and 2) by baseline determination.

Optical Contour Maximization. DNA molecules can be almost totally elongated by the action of a relatively weak electrical field if one end of the DNA is fixed (59, 76, 77). Length is simply measured by imaging the elongated molecule using fluorescence microscopy. However, fixing large linear DNA molecules is cumbersome, and previous elongation studies did not attempt to correlate length with molecular mass in any systematic manner.

A practical sizing methodology, termed Optical Contour Maximization (OCM), is based on the discovery that when a linear DNA molecules snags an obstacle during electrophoresis in a loose gel matrix, it elongates nearly completely to form a metastable hook that can persist for several seconds (46). This loose matrix can be found at the coverslip-agarose gel interface. The longest observed hook contour length can be determined from rapidly collected images and that these maximal lengths which show a linear correlation with respect to reported size (240–680 kb; (46)). To summarize, OCM provides very precise size measurements that are superior to most results derived from analysis by pulsed field electrophoresis.

Spectroscopic Studies of DNA Molecules in a Gel

A fluorescence dichroism spectrometer (similar to (78–80)) can be constructed that is attached to an inverted microscope; the microscope can be also equipped with a SIT video camera and interfaced to a video-digitizing board housed in a computer. A major advantage of such spectroscopic instrumentation, in contrast to that of Boredjo and Holtzwarth (78–80), is that molecules can be imaged, as well as collecting spectroscopic data on a small number of molecules using the microscope-spectrometer combination. Imaging and spectroscopic data are somewhat complementary, and combining them allows almost completely characterization of an electrophoretic system. Consider that fluorescence dichroism monitors the average coil orientation, at a resolution that is beyond the Rayleigh limit (approximately 1 gel pore in size), whereas, imaging experiments elucidate gross coil conformation dynamics. Such an instrument can be used in this invention to correlate the imaged molecular dynamics of large DNA molecules during electrophoresis with their change in dichroic ratio.

As described herein, optical mapping is a new physical mapping approach that encompasses many new single macromolecular phenomena and which results in rapid construction of ordered restriction maps from single DNAs. Restriction fragments are sized optically with minimal perturbation, and multiple molecules can be analyzed in parallel.

The following methods used in the present invention provide improved sizing capabilities. New methods aimed at reducing or eliminating apparent partial digestion are also provided.

Methods for Fixing Single DNA Molecules for Light Microscopy

Optical mapping analyzes large naked DNA molecules, typically microns in diameter, that exist in solution as random coils. These molecules must be stretched out and fixed in place before image separation can be performed of fragments resulting from site-specific cleavage. Molten agarose is used to supply a fluid flow to stretch large DNA molecules and subsequent gelation to fix them in place. Gel fixation is firm enough to hold molecules in place, but gentle enough to permit some slippage upon cleavage so that cut sites are observable. Indeed, how agarose is able to fix large DNA molecules is not well understood. A more reproducible fixation can also be obtained with regards to controlling the level of elongation, to preventing premature relaxation and to allow more reliable detection of cleavage sites when formed, and to improve throughput.

(i) Understanding and Characterizing the Gel Fixation Process

Gel fixation is a fundamental component of optical mapping, yet how agarose traps and fixes molecules is poorly understood. It is not even certain that agarose fibers are physically locking and entrapping DNA molecules, thereby fixing them in place. Gel fiber-DNA interactions may also play a prominent role in DNA gel electrophoresis, as discussed herein. Indeed, full characterization of the mechanisms of gel fixation will lead to improved molecular fixation techniques that should be applicable to a broad range of single molecule methodologies beyond optical mapping. As described herein, gel fixation of elongated molecules is expected to result from a combination of gel fiber-DNA interaction and relaxation effects, particularly at the ends of molecules.

Such different interactions can be characterized by studying the DNA segment distribution in a series of samples of gel-fixed molecules that vary in the size of the DNAs and in the gel concentration. Intensity measurement techniques developed for optical mapping of the present invention can also be used to create intensity profiles of fixed, single DNA molecules along the major axis as a function of time after mounting (see FIG. 10), also of the present invention. By analyzing these intensity profiles as they vary with time, trapping points can be located and/or characterized along the embedded molecule as regions of intensity invariance. In other words, as a fixed, elongated coil attempts to relax, coil segments move in and out of pore volumes. If there is an obstruction, i.e., strong fiber-DNA interaction, coil segments will not be able to relax past that position. To further evaluate the degree of trapping, the system can be perturbed with a carefully measured electrical field and image resulting motions, with accompanying intensity measurements. From these analyses, the mean number of trapping points per kb of DNA can be determined as a function of the total coil size and gel concentration. The effects of ionic strength and divalent counter ions on fixation can also be measured.

Gel Concentration Effects

The gel concentration used for optical mapping has not been optimized; but 0.1–3% LGT (low gelling temperature) agarose, or any range or value therein can be used, such as 1% LGT agarose. Since gelation fixes embedded molecules, systematically varying the gel concentration should modulate the degree of fixation and ultimately the rate of molecule relaxation. For example, a higher gel concentration may be desired for small fragments as compared with larger ones, this would serve to retard relaxation and facilitate our analyses of these smaller fragments. Additionally, gel concentration affects gelation kinetics so that smaller molecules are trapped in an extended conformation before substantial relaxation takes place. Such kinetics and their effects on trapping can be determined by systematically vary gel concentration for a range of DNA sizes (30–1,000 kb) and studying its effect on stabilizing molecules against premature relaxation and on apparent cutting efficiency. Molecular relaxation are evaluated by measuring lengths as function of time, as described herein, and cuts are scored using optical mapping procedures.

(iii) Adhering Large DNA Molecules to Glass

Yanagida showed that short elongated DNA molecules could be adhered to glass in the presence of $Mg^{+2}$ and imaged by fluorescence microscopy (81). The adhesion was stable enough to permit film exposures, lasting several minutes, of individual fluorochrome stained DNA molecules. This technique can be adapted according to the present invention in order to spread and fix large DNA molecules to magnesium ion "loaded" glass slides (loaded with $Mg^{+2}$ by soaking glass slides in magnesium chloride solution). Our procedure consists of the following: spermine condensed molecules obtained from agarose treated electrophoresis gel slices of separated yeast chromosomes, where the agarose has digested agarose into small saccharides, is spread in a thin layer over the magnesium loaded glass. Spermine condensation can be included to substantially prevent shear-induced breakage. The spermine concentration is controlled so that the available magnesium in the loaded glass can decondense the molecule and at the same time adhere it to the glass surface. Subsequent optical mapping is carried out with the modification that restriction enzyme is added to the glass-fixed molecule, instead of $Mg^{+2}$ being added as conventionally occurs. If cut sites do not appear readily due to firm fixation conditions, then adding a small amount of EDTA helps loosen overly fixed molecules.

Glass fixed molecules possess several advantages over their gel-fixed counterparts: 1) since molecules are attached to the cover slip, images are very sharp and bright (no gel to scatter and obscure); 2) images have less fluorescence background in the field, agarose gel is a relatively crude product with extraneous fluorescence; 3) bright, clear images are easy to process by fully automated routines, and 4) fixation can be tighter so that molecules can be more effectively spread out. This last advantage is a critical requirement for producing higher resolution maps, which naturally consist of more numerous, smaller fragments.

(iv) Using Electrical Fields to Spread and Fix Molecules

DNA molecules can stretch out and elongate considerably during gel electrophoresis, as has been shown by fluorescence microscopy (53, 62). Although electrical fields elongate molecules during electrophoresis, it not obvious how to maintain this state in the absence of any applied field. In fact, trying to maintain elongation during gel electrophoresis is antithetical to separation mechanisms which require some relaxation processes to size resolve DNA molecules.

From our trapping studies, e.g., as described herein, segments of electrophoresing coils have been imaged that serve to trap or anchor a whole molecule in place. High electrical field strength can be used to form these anchors during agarose gel electrophoresis, and these anchors can persist long after the field is removed, e.g., for an hour or more. Trapped, fixed molecules are useless for electrophoresis, but are just the molecular conformation suitable for optical mapping. Exploitation of such conditions that trap molecules unproductively for electrophoresis, productively trap molecules for our optical mapping of the present invention. Accordingly, systematically varying of field strength conditions for a range of molecular sizes (200–1000 kb), as well as measuring the resulting lengths and elongated state persistence times, can be used according to the present invention for analytical techniques of optical mapping, as described herein. Agarose gel concentration can also be systematically varied. Thus, optimal elongation conditions for optical mapping can be established.

Single Molecule Sizing Methodologies. Optical mapping is dependent on methodologies for sizing single molecules and construction of restriction maps of higher resolution and precision can be provided by such methods of the present invention. As non-limiting examples, five single molecule sizing methods are provided, including apparent relative length, fluorescence intensity ratio, relaxation in a gel, baseline, and OCM (optical contour mapping). These can be usefully classified into two groups: techniques that require molecular perturbation and those that require none. Non-perturbation sizing techniques such as measurements of fluorescence intensity of single molecules and apparent length measurements are convenient to use because they do not require a sophisticated microscope mounted chamber and attending controlling electronics. Additionally, non-perturbing sizing techniques are also well suited for parallel measurements. Despite some of these advantages for the non-perturbing class, the perturbation-based sizing techniques of the present invention provide unexpectedly superior results, since they provide high precision and resolution.

Several approaches for optically sizing DNA fragments of at least 500 bp can be provided by the present invention, e.g., as follows.

Apparent Relative Length and Intensity Measurements

As described herein, ordered chromosome restriction maps can be generated according to the present invention by using relative intensity and relative length measurements. Molecules are first elongated and fixed in agarose gel containing restriction enzyme. Magnesium ions are then diffused in, triggering digestion, and restriction sites are visualized as growing gaps in the DNA molecules. This approach is simple, effective, and has superior sensitivity, since one molecule can be visualized directly. The microscope chamber may consists of a slide with a hole drilled in it, gel and a cover slip. Although no electrodes are used to apply electrical fields to stretch or manipulate the molecules, it is possible that applying electrical fields could beneficially perturb the system. Consider that both relative apparent length and relative intensity sizing methodologies require that fragments remain elongated for optimum results. Gel fixation is not perfect, and fragments suboptimally fixed are prone to premature relaxation which can complicate sizing attempts. Furthermore, fixation of the DNA to the gel matrix can interfere with the observation of cut sites, which requires local relaxation to produce visible gaps.

Bearing the above considerations in mind, electrical fields can be used to perturb molecules during optical mapping so that more usable and more precise data can result from a single mount. An electrical field can be controlled to stretch or move DNA molecules; these perturbations will elongated relaxed molecules and allow relative intensity and length measurements. Perturbations should also reveal apparently partially cut molecules so that cut sites, present but not otherwise visualized as gaps, appear. Recent preliminary data from our laboratory show that, indeed, electrical fields do decrease the degree of apparent partial digestion. Electrical perturbations are implemented during optical mapping by using the chamber. The only additional modification is to totally fill the chamber with agarose and DNA.

Alternate Approaches to Contour Lengths Measurements

A sizing methodology, termed Optical Contour Maximization (OCM (46)), which transiently stretches linear DNA molecules out in a loose gel matrix using an applied electrical field and then sizes them by optical length measurement. Molecules stretch out by snaring on obstacles in the loose matrix to form hook-like conformations. Remarkably, a relatively weak electrical field (e.g., 5–30, e.g., 20 volts/cm) is sufficient for complete elongation of a tethered or temporarily snared DNA molecule (46, 59, 77). If the hook arms are similarly sized, then the molecule can be stretched out to nearly its full contour length. OCM sizing accuracy and precision is very high, as good or better than pulsed electrophoresis based measurements.

Figure 11A:
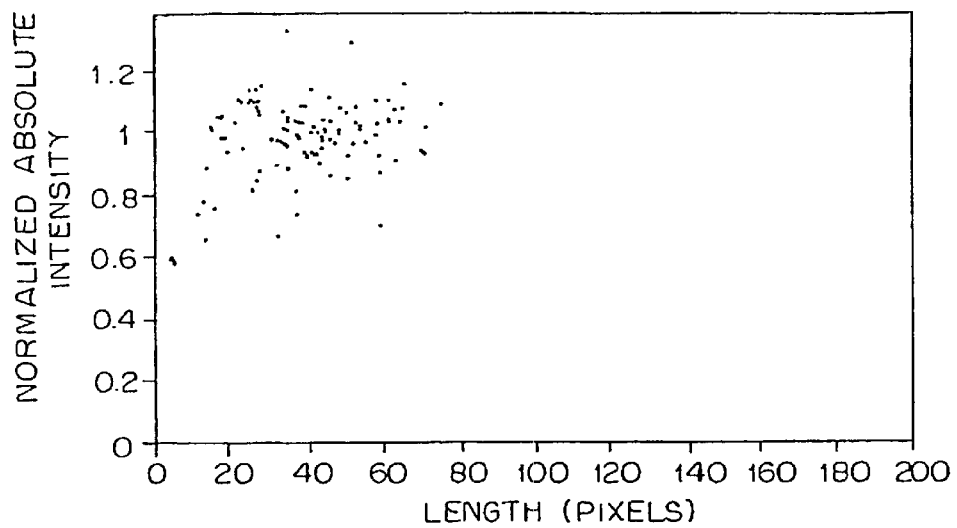
FIG. 11 shows a scatter plot of normalized absolute intensity vs. apparent length. Absolute intensities from individual images were calculated (6) and plotted against apparent length over a time interval typically used in optical mapping (10–15 minutes). For each sample, the initial intensity was found by averaging absolute intensity values from groups of 5 adjacent images and taking the largest value. The values from several samples were normalized by dividing values from each image by the initial intensity for the sample. (A) chromosome I 120 kb Not I fragment, 7 samples. (B) chromosome XI 285 kb Not I fragment, 4 samples. (C) chromosome XI 360 kb Not I fragment, 4 samples.
Figure 11B:
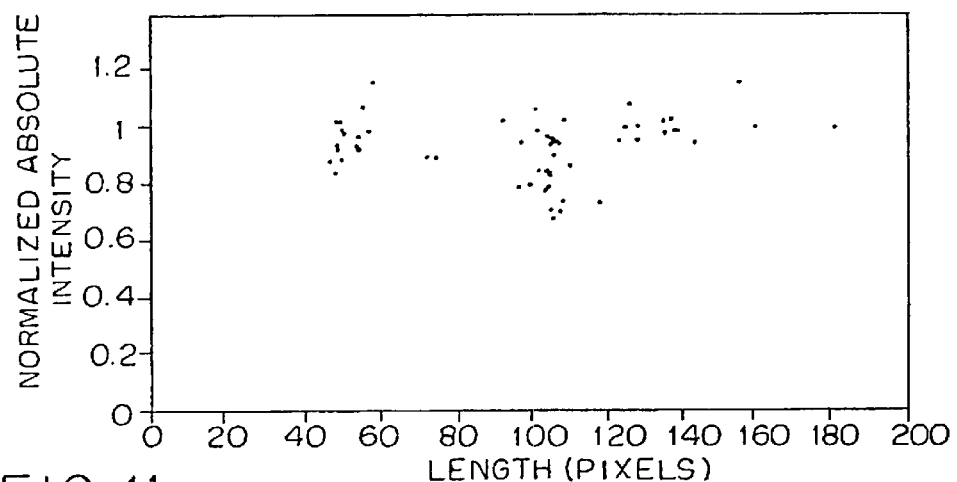
Figure 11C:
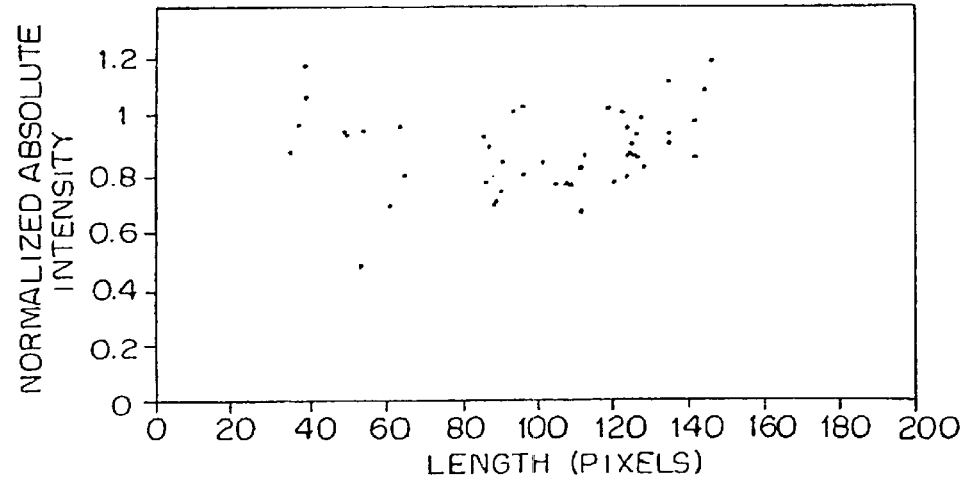

OCM can be modified as known to provide high throughput methodology of the present invention by using a new physical effect to elongate molecules and new image processing methods to measure molecular lengths in real time. A fluid-gel interface, which is easily made, provides an ideal situation for differential frictional forces to act on an electrophoresing molecule and elongate it to nearly its full contour length, just like in OCM. The net elongation force on the molecule is determined by the differences in DNA frictional coefficient in the gel matrix versus the fluid phase. More precisely, when a DNA molecule electrophoreses through a gel-fluid interface, as depicted in FIG. 11, the fluid frictional forces are much less than those posed in the gel matrix. These forces are, typically, at least 10-fold less (55), and differences vary with gel concentration. Molecular conformation is dynamic within the gel matrix, but on the average it is relatively compact. Frictional forces are reduced when a molecule merges from the gel matrix into the free solution presenting a differential force across the molecules sufficient enough to cause it to elongate. Immediately after a molecule completely pulls free of the matrix, elongation forces disappear, and the molecule relaxes back to a compact, free solution conformation. Reversing the electrical field sends the free molecule back into the gel matrix; the length measurements can then be repeated and averaged as many times as needed, depending upon the desired accuracy.

High throughput is accomplished by electrophoresing molecules through the interface at a rate of approximately 20–50 molecules/minute. Contour lengths can be measured and tabulated from stored data by the same techniques and computer algorithms developed for optical mapping and coil relaxation measurements, imaged, such as the non-limiting example of images from a SIT camera are rapidly digitized, frame averaged and stored as 16 bit files at a frame rate of 30/sec. For example, 120 file frame buffers can be used in the analyzing computer. This means that 120, 512×512 pixel images can be digitized and stored in as little time as 4 seconds. More rapid image storage is available by simply reducing image size, in which case the same hardware can store 480, 128×128 pixel images. Processing algorithms can thus size 5–10 molecules simultaneously by gathering approximately 10 images (averaging 4–16 frames together) in a 20 second interval. Using a 1 gigabyte hard disk for storage means close to 2,000 full frame images or sizing data for 1,000–2,000 molecules can be stored. Processing algorithms can be set up to work in batch mode and require approximately 3–5 hours to process 1 gigabyte worth of image data into 1,000–2,000 sizes tabulated on a spreadsheet. These processing times are based on unattended operation, but operator interfaces can also be used that permit convenient manual identification and marking of molecules for analysis.

High image quality greatly facilitates image processing. Fluorescence images of DNAs obtained in fluid rather than gel are brighter, sharper and relatively free of fluorescing artifacts. Consequently, they are ideal for unattended image processing since they can be transformed into reliable binary or digital images, which are easily accepted by our processing algorithms. This high throughput sizing methodology can be tested and benchmarked by using a series of Not I digested yeast chromosomes mixtures (containing DNAs 30–900 kb), of increasing complexity. Statistical analysis to calculate the precision of single measurements can be performed and the ultimate accuracy of this methodology determined. Confidence intervals are determined to establish the minimum number of molecules necessary for adequate analysis of complex mixtures. This analysis will help determine the usable size resolution and size discrimination levels. Sources of noise and systematic error are detected and eliminated as much as possible. A lower size limit of 5–20 kb and an increased upper size limit are provided by the present invention since molecules with contour lengths greater than the microscope viewing field are sized by offsetting a known distance from the interface and monitoring only coil ends.

A Fluid Interface System for Sizing by Coil Relaxation

As discussed herein, coil relaxation is quantitated in gel and derived mathematical relationships for molecular size based on our theoretical and experimental calculations and observations. This measured relaxation time is very sensitive to molecular weight and varies as (molecular weight)$^{1.66}$, whereas length measurements vary only as (molecular weight)$^1$ at their best. Within a given size distribution the largest molecules dominate the measured relaxation, so that the smaller molecules in heterogeneous mixtures cannot be analyzed in a chamber (83). Unfortunately, the inability of this method to determine a size distribution made it impractical for use in most standard analyses in molecular biology. Under the microscope, of course, individual chains are observed independently, effectively deconvoluting any mixture.

Coil relaxation can be measured according to the present invention in free solution using the described gel-fluid interface system in free solution for providing rapid and sensitive techniques for size determination of heterogeneous samples, a continuation of our present work. Yanagida and colleagues were able to measure coil conformational dynamics of single molecules in solution, using fluorescence microscopy, yielding reliable average molecular dimensions that can easily be related to size (44). Other optical methods such as electric birefringence (84) and dichroism (85) have also determined the same weight dependence on relaxation as the shear based, viscoelastic technique.

The gel-fluid interface system offers an almost ideal set of conditions for relaxation measurements in free solution: 1) the degree of elongation can be easily controlled by varying the electrical field strength or the gel concentration; 2) elongation conditions are uniform and reproducible; 3) repeated measurements are simple since reversing the field permits re-extraction of molecules from the interface, and 4) overall, experimental conditions are controllable and measurements take place in a well-defined field of view, an important consideration in microscopy.

Relaxation times are determined by electrophoresing molecules through the gel-fluid interface described in the previous section (see FIGS. 11A–C) and initially using the same techniques developed for gel-based relaxation measurements. These determinations use optical length measurements at periodic intervals to quantitate the degree of relaxation. The change of measured molecular lengths as a function of time are fitted to a single exponential decay to obtain the relaxation time. Solution relaxation mechanisms are somewhat different than gel-based ones, in that coil segments are not confined to move within a tube, or a series of connected gel pores. In free solution, elongated DNA molecules relax by evolving from a drawn-out prolate ellipsoid to a more symmetric, spherical conformation (44). Relaxation times are also shorter in free solution (generally 10-fold less, (55)): for example, a 500 kb molecule has a relaxation time of 4 seconds. However, since solution relaxation times are inversely proportional to solution viscosity, measurements on small molecules can be made on a convenient time scale by simply adding glycerol or sucrose to increase viscosity. It is significant that the shorter relaxation times manifested by solution based relaxation measurements are advantageous for any high throughput approach.

Image collection procedures are virtually identical to those described in the previous section and the same images can be used for length and relaxation measurements. Image processing routine can be modified to fit ellipsoids around the relaxing coil mass, and the associated major and minor axes are used to measure relaxation progress. As described in the previous section, a set of molecules are used to benchmark and establish relaxation dependent sizing conditions. Statistical analysis can be used to determine the precision and accuracy of these measurements.

Providing the Gel-Fluid Interface System for Fluorescence Intensity Measurements A single molecule fluorescence intensity method can be used to measure the relative fluorescence intensities of restriction fragments embedded in agarose gel that form during optical mapping. The relative fluorescence intensity of a restriction fragment correlates well with its relative mass and have used these measurements to construct preliminary Optical Maps for several chromosomes of *Saccharomyces cerevisiae*. In general, fluorescence intensity measurements are difficult to quantitate on a microscope-derived image, so that relative measurements provide a sort of internal standard. There are several drawbacks to this approach since errors are absolute instead of being relative. This means that, for example, a 20 kb standard deviation applies equally to a 60 kb fragment as well as to a 900 kb sized one. In other words, the coefficient of variation (mean/standard deviation) can vary enormously and will penalize small fragments more than larger ones.

The gel-fluid interface system can be used in this invention to obtain high resolution fluorescence intensity measurements of single molecules. Measurement precision can be increased and lower size limitations made for these measurements. Increased sizing performance accrues from a number of factors, such as, but not limited to, the simultaneous use of three sizing methods will increase precision and accuracy (length, relaxation and intensity); the fluid-gel interface system produces optically flat molecules more consistently than gel fixation; the degree of molecular elongation is more controllable than gel fixation, and the elimination of gel provides sharper, brighter images that are more free of fluorescing artifacts. As mentioned previously, high quality images are easier to image process automatically.

Intensity quantitation requires that molecules be in focus. The gel-fluid interface system creates elongated molecules which are optically flat. More precisely, a high power, high numerical aperture objective has a depth of focus approximately 0.2 microns deep (86), so that for a molecule to be optically flat, or totally in focus, it must lie completely within a box with a thickness comparable to this value.

Since molecules are continuously electrophoresed in the gel-fluid interface system, intensity measurements must be made on moving targets. A potential problem is that images must be grabbed quickly to avoid serious motion-induced distortion, and time is limited for frame averaging. However, for short observation times, higher illumination levels (providing greater signal to noise) can be used without significant breakage or bleaching. Frame averaging can be used to reduce noise and increase the number of gray levels. For example, we use a 8 bit digitizer with a 16 bit frame buffer and average 32 frames, which is approximately 1 second of video. This gives 13 bit images containing almost 8,200 levels of intensity. If images are grabbed more quickly, the resultant images contain fewer levels of intensity. Shutting off the electrical field is one way to increase image averaging time. However, molecules begin to relax immediately and move partially out of focus.

Motion problems can be solved by initiating imaging while the molecule is still partially embedded in the agarose. At this point, the molecule is optically flattened and is not moving rapidly since it is still embedded in the agarose matrix. To ensure that long molecules are completely in view, the electrical field can be varied to produce different degrees of elongation. Using computer-interfaced programmable power supplies, ramping the field strength systematically can also be tested to provide initial conditions that mildly elongate molecules for intensity measurements and then increase the field strength to induce full elongation for length measurement and relaxation time determination after molecules completely disengage from the gel. As a non-limiting example, averaging for 16 frames, or 0.5 seconds, should not be at risk for significant motion-induced distortion effects. This produces 11 bit data, which provides sufficient resolution for most intensity determinations; satisfactory results have also been obtained with only 8 bit data.

To minimize errors arising from relative intensity measurements, a number of internal standards can be placed into samples so that fluorescence non-linearities arising from uneven illumination can be substantially reduced or eliminated. The internal standard preferably meets several requirements: 1) negatively charged to avoid sticking to DNA; 2) fluorescent in the same absorption and emission wavelengths as the DNA-fluorochrome complex, and 3) readily distinguishable from the test DNA molecules to be measured. Small DNA molecules (20–50 kb) can be used as internal standards. These molecules are dispersed throughout the sample to be measured and preferably react identically as the sample DNA to illumination and electrophoretic conditions (e.g., in free solution). The internal standards to determine relative mass, instead of using contiguous restriction digestion products from the same parental molecule. To optimize these determinations, we will systematically vary the DNAs used as standards, utilizing standards of different sizes, and measure their relative fluorescence intensities. If necessary, empirical correction factors are calculated to ensure linearity.

Sizing Small DNA Fragments by Measurements of Fluorescence Intensity

The lower size limit of optical mapping is currently 30 kb, and it would be useful to extend resolution to smaller fragments. Thus, accurately sizing DNA fragments as small as 500 bp using fluorescence microscopy is an important step in creating high resolution maps of large DNA molecules, e.g., using restriction enzymes with 6 bp recognition sites.

Conventional measurements of fluorescence intensity of molecules containing small numbers of fluorochromes are plagued with problems of low signal intensity and low signal/noise levels. Essentially, when the photon counting level on a microscope is approached, more than the sample fluoresces and your microscope is full of stray light. Fluorescence lifetime capabilities of this instrument can be applied as a sophisticated filtering system to eliminate stray light and background fluorescence (87, 88). This approach is expected to significantly improve the low light detection capability relative to our present SIT based system.

The heart of the imaging fluorescence lifetime microscope is the coiled image intensified charge coupled device, or, simply, ICCD. This low noise device can image under remarkably low light conditions that approach single photon counting levels (86). The signal/noise performance is at least twice as good as a frame averaged SIT camera (89). The ICCD is also gatable down to 5 ns, which is shorter than most fluorescent probe lifetimes. The intensification stage on this camera consists of a microchannel plate, which functions like a bundle of photomultiplier tubes, so that a small number of photons triggers an avalanche of electrons that hit a phosphor screen and produce a bright image. The phosphor screen image is sensed by a CCD chip attached to the intensifier by a fiber optic coupler, and the chip-born image is dumped into the camera controller and digitized (90, 91). Similar devices are often used for military night vision equipment. As mentioned, the intensifier is gated so it can be opened and closed, just like a camera shutter. This "shutter", however, is very fast and has a gating ratio of greater than $5 \times 10^6:1$. The ICCD is a preferred imaging system for quantitative work when using fixed, non-moving samples (92), such as in methods of the present invention.

To maximize the signal/noise ratio, exploitation of the gating feature of the ICCD is used to open the shutter only after the excitation pulse is finished, stray light and scattering from the illumination source being substantially eliminated. Hence, having created emission photons exclusively from fluorescence under controlled and careful timing of the image collection, bound from unbound emissions, or stray fluorescence, can be distinguished on the basis of fluorescence lifetimes.

As non-limiting example, for the ethidium bromide-DNA complex, the dye lasers are tuned to 525 nm, and the gate widths are set to 63 ns, since the lifetime of the bound species is 21.1 ns (93), so approximately 3 t should be optimal. The lifetime of unbound ethidium bromide fluorescence in water is only about 1.6 ns, so the free fluorochrome emission will closely follow the excitation laster profile and are easily selected against. Other sources of background fluorescence include immersion oil, glass slides and sample impurities, and fluorescence from these sources can also be attenuated with this technique.

Gated pulses can be are timed and synchronized with fluorescence decay. The gating pulser is timed to produce a high voltage signal during the fluorescence lifetime of the fluorochrome-DNA complex. The high voltage pulse opens and closes the electronic shutter. Illumination are pulsed with a 8 ns FWHM duration so that excitation is present only when the shutter is closed. Eliminating filters increase light throughput and remove another source of unwanted fluorescence. the laser excitation repetition rate is variable (1–100 Hz), and the fluorescence emissions accumulate as charge on the ICCD head; a resultant image builds up consisting of bright spots with intensities proportional to mass.

Two nanosecond lasers are appropriate for these methods, such as but not limited to, a Continuum Corporation Nd-YAG pumped TiSaphire tunable solid state laser and a Lambda Physik excimer pumped dye laser.

The sensitivity and size resolution of such system can be evaluated using EcoRI digests of lambda bacteriophage DNA stained with ethidium bromide. Images are generated in the described system and the spot intensities, corresponding to single molecules, are tabulated by our image processing routines. These are subsequently binned to obtain histograms depicting intensity populations which correspond to fragment size populations. This sort of analysis can be done according to (94) on DNA molecules flowing through a synthetic silicon matrix. The precision and accuracy of these measurements can be calculated and used to set proper bin widths for the histogram analysis.

DNA fragments preferably are in nearly perfect focus. If fragments are out of focus, intensity values can vary for the same sized molecule. To ensure that molecules are in focus, magnesium ions adhered DNA molecules can be used to clean glass surfaces. Other methods may also include the use of centrifugal forces to spread DNA fragments in solution or gel out on a glass surface.

Non-uniform illumination can be corrected by a combination of careful illumination adjustments and by use of processing routines developed for relative intensity measurements in optical mapping. Essentially, this routine locates local surrounding pixels and uses their intensity values to calculate local background values. Local background values will compensate for uneven illumination and thus act as shading correction.

Other fluorochromes can be used, e.g. those having varying degrees of sequence specificity and, if appropriate, fluorochromes with complementary sequence biases used, such as ethidium homodimer and ethidium-acridine orange heterodimer. Contrast can be further improved by eliminating unbound fluorochrome. Ethidium monoazide (Molecular Probes, Inc.) is a fluorochrome that covalently attaches to DNA in high yield by photochemical means, and unbound compound can be readily extracted from the labeled DNA before mounting.

A series of well-defined DNA fragments is added to the sample as internal fluorescent size standards. The concentration of fluorescence intensity standards is adjusted so that they are readily identifiable in any histogram analysis. A nearly linear relationship between mass and fluorescence intensity is expected.

Fluorescence lifetime microscopes can also be used to improve intensity based sizing for larger fragments (50–1,000 kb) or 1–1,000,000 kb.

The results of the above sizing analysis obtained for a restriction digest of a pure sample can be an optical fingerprint and analogous to a fingerprint (without the hybridization step) derived from gel electrophoretic methods. Ancillary methods can use this advanced sizing methodology to produce ordered maps from genomic DNA and YACs of particular individuals or populations or subpopulations.

Detection Methods for Localization of Specific Sequences by Hybridization to Single DNA Molecules While optical mapping creates ordered restriction maps, these maps alone cannot locate precisely where known sequences or genes lie on the chromosome. Modern in situ hybridization techniques (96–99) can locate single copy genes, and the resolution of localization is steadily improving due to the trend in using increasingly decondensed chromatin (98, 99). The chromatin is spread out as much as possible so that the detected DNA loci are as far apart as feasible. The ultimate extension of this idea is to use single DNA molecules stretched to a length corresponding to their molecular contour length and then fixed. Optical mapping and/or RARE can be used to fine-map genomic DNA, such as genes in *Saccharomyces cerevisae* and *Candida albicans* or other genes in higher animals, such as humans.

Gene locations can thus be determined for single, elongated, fixed molecules by using optical mapping to size single restriction cuts mediated by RATE, and the sizing resolution is comparable to that obtained by pulsed field electrophoresis analysis.

Approaches to precisely locate sequences on large naked DNA molecules may include techniques of this invention which allow tagging and detection of RARE-mediated hybridizations to double-stranded molecules using microscopy. These new approaches rely, in part, on labeling the RecA-oligonucleotide filaments prior to complex formation (68) with the target DNA. Detection is based on fluorescent beads and on chemiluminescent tagging using alkaline phosphatase. Hybridization with tagged RecA filaments to optically mapped single molecules is similar to in situ Southern analysis.

Providing Optical Mapping Methods to Use RARE for Gene Localization

RARE sites can be detected on a large DNA molecule using optical mapping. However, direct detection of the formed complex eliminates the requirement for detection of the gap due to cleavage and serves as a touchstone for the formulation of a new set of methods for fine mapping known sequences. In direct detection strategy, tagged RARE binding sites appear along a molecule as bright spots of a color differing from the main molecule. The color difference provides, of course, the needed contrast. This is analogous to in situ hybridization with different colored probes against DAPI stained chromosomes.

Cleavage Visualized RARE

Specific genes can be mapped onto single naked DNA molecules using RARE cleavages coupled with optical mapping. A number important experimental variables provide optimization, optimizing the RARE reactions to increase yield of clean fragments, using protocols developed by Koob and Szybalski (66, 67); (optical contour mapping); visualizing RARE cleavage in our more advanced microscope chamber that has electrodes to electrically manipulate and perturb the system; extending visualization of RATE cleavage to multiple sites; and combining RARE with other restriction enzyme digestion during optical mapping. To do this RARE is performed on a mounted sample, followed by diffusion of another enzyme into the viewing field, by simply adding enzyme through the same space used to add magnesium ions for optical mapping.

Attached Fluorescent Beads for Optical recA Mediated hybridization Detection. Single fluorescent beads are easily imaged with fluorescence microscopy, including the smallest ones with a diameter of just 0.01 microns. (Although exceeding the Rayleigh limit, this bead appears as a bright spot.) Fluorescent beads are a good way to label single DNA molecules for image processing because individual beads are intensely fluorescent, morphologically distinctive, available in wide range of fluorochromes of differing spectral qualities, and are easily attached to oligonucleotides. For example, Molecular Probes, Inc., sells latex beads with coatings of carboxylate, avidin or streptavidin in 6 spectral ranges (colors) and sizes varying from 0.01 to 2 microns. The availability of carboxylate modified and streptavidin coated beads offers many alternatives for binding them to DNA molecules.

Synthesizing oligonucleotides can be covalently attached to a series of differently sized fluorescent beads (0.01–0.05 microns) to optimize RARE conditions. Smaller beads are preferable because they diffuse more readily through agarose gel but larger beads are easier to derivatize due to their larger surface area (100). Fluorescent beads of similar size have been imaged electrophoresing through gels by fluorescence (101). Forming RecA filaments using these modified oligonucleotides and assaying their formation by functionality in a RARE test system can also be used. The test system is a 60 base region of the yeast LEU2 gene, and the target LEU2 gene, located on Chromosome III. The RARE protocol is followed: a RecA filament is made with this oligonucleotide and diffused into a chopped yeast gel insert, followed by treatment with EcoRI methylase, extraction of the targeted complex and digestion with EcoRI. The digested sample is then run out on a pulsed field gel for analysis. Conjugating oligonucleotides can use streptavidin-biotin attachment schemes since biotinylated oligonucleotides have previously been shown to form functional filaments with RecA and offer the option of adding beads after the filament has complexed with the target DNA (102).

Detection of the RecA complex on the microscope can require visualization of the fluorescent bead attached to the target molecule,, no addition of enzyme may be needed, no magnesium ions are diffused in and no prior methylation is carried out. For microscope work, electrophoretically separated chromosomal DNAs instead of total genomic material are used. Samples can consist of our yeast chromosome test system; other chromosomes with previously mapped sequences can also be used. Isolated yeast chromosomal gel bands, are chopped into bead sized pieces, equilibrated in RARE buffer, melted, and re-equilibrated at 37° C. Bead-linked RecA filaments are then added to the molten mixture to form filament complexes at the target sequence site; the mixing in the molten agarose are more effective than during diffusion through agarose gel. The molten RecA-bead-DNA mixture is then stained with DAPI and spread on a microscope slide for optical mapping. Finally, length and intensity measurements are used to map the bead position. "Red" beads (Molecular Probes, Inc.), can be used to provide contrast to DAPI's blue fluorescence.

Reducing Background from Tagged RecA Filaments

The efficiency of RecA mediated hybridization is strongly dependent on the filament size (in bases) and concentration (194). The amount of labeled RecA filament may be a concern in optically based methods: too many free fluorescent beaded filaments can obscure imaging beads present in the complex with target molecules. The following simple actions can be taken to eliminate this problem if it occurs:

Carefully titrate the amount of labeled filament and balance the minimum necessary hybridization efficiency for convenient observations against contrast quality. RecA-mediated hybridization does not require the RARE methylation and restriction enzyme cleavage steps, so that hybridization efficiencies do not have to be critically optimized for acceptable results.

Unbound filaments can be diffused out through dialysis, or mild electrophoresis in gel fixed systems could selectively sweep filaments from the viewing field and leave the much larger target-filament complexes in place. If necessary, additional RecA protein can be added for stabilization.

Providing Chemiluminescent Detection of RecA-Mediated Hybridization

Chemiluminescent labeling of oligonucleotides for non-isotopic detection in Southern blots and other techniques is becoming popular because of its high sensitivity, among other merits (105). In general, alkaline phosphatase is attached to oligonucleotides (there are several ways to do this and commercially available systems), which are then hybridized to target DNA. Following formation of hybrids, a chemiluminescent substrate is added, usually 1,2dioxetane, which rapidly decomposes into a chemiluminescence generating compound. Light is emitted with a maximum at 470 nm and a half life of 2–30 minutes depending upon the chemical environment.

Given the tremendous sensitivity of chemiluminescence and the availability of high quality commercial kits, chemiluminescence can be used in this invention to optically detect RARE on single DNA molecules using the techniques developed for optical mapping. For example, alkaline phosphatase can be covalently linked to oligonucleotides (106), or DNA linked to biotin-streptavidin attachment schemes (107; with kits commercially available). The conjugated oligonucleotides will then be made into RecA filaments and tested for RARE effectiveness as described in the previous section. One advantage of the biotin-streptavidin mediated alkaline phosphatase linkage is that excess biotinylated alkaline phosphatase can be easily dialyzed out of the system to reduce stray chemiluminescence. A chemiluminescent detection system can be used with RARE, and optical mapping using most of the steps described herein. The RecA-oligonucleotide (linked to alkaline phosphatase)-target DNA complex in molten agarose gel and then mount this for optical mapping. Instead of diffusing magnesium ions in to trigger enzymatic cleavage, dioxetane is diffused, required by the chemiluminescence system, for visualization of RARE sites. The chemiluminescence activity can then be visualized through the microscope using an ICCD camera (105); with no illumination necessary. To image the entire molecule, DNA-fluorochrome fluorescence can be used, and different fluorochromes used if initial compounds used quench or interfere with chemiluminescence.

Using Imaged Energy Transfer to Reduce Background from Tagged RecA Filaments. An alternative approach is to exploit energy transfer between the fluorochrome labeled DNA and the bead attached to the oligonucleotide. Excitation can be selected making the DNA-fluorochrome complex the donor and the bead the acceptor. This would mean that the bead could fluoresce only when it is within 100 angstroms or less of the donor. However, efficiency of transfer falls off dramatically with distance (108). Energy transfer imaging using fluorescence microscopy with different microscope filter combinations allows visualization of the donor, acceptor, and the donor-acceptor pair; these are conveniently slid in and out of the illumination path. A good energy transfer donor to use here is ethidium bromide or the homodimer (110), since these fluorochromes bind tightly the fluorescence yield increases dramatically upon binding. A concern is that free fluorochrome can act as a donor, though probably not as effectively the intercalated material. If free chromophore proves to be problem, the filament can be split into two parts and fluorescent beads attached in a head-to-head fashion so that they will serve as the acceptor-donor pair for energy transfer imaging. Another concern is that latex beads are notoriously prone to aggregation, which problem can be solved appropriate selection and use of chromophores (Molecular Probes, Inc., Portland, Oreg.). Measures ensuring against aggregation include maintaining some charge on beads through careful attention to ionic strength, and use of Triton X-100 detergent or BSA.

Increasing Throughput in mapping using Genomic DNA or YACs. The electrophoretic fingerprinting of YACs is an important technique in many contig assembly efforts (i, 11–13, 32, 33, 38). Although many gel related manipulations have been automated (11, 39), the task of running, analyzing and tabulating the results of thousands gels is far from routine. One major obstacle in automation is gel electrophoresis. It can be slow, and there are often difficulties involved in converting band positions to tabulated numbers automatically and with a high degree of reliability and accuracy. Manual intervention is often necessary to check and monitor results. Southern blotting and hybridization steps are required to complete the fingerprinting process, and this procedure is also plagued with difficulties when automated (11, 38–41, 111, 112).

RARE Based Approaches to Mapping

Rapid Chromosome Fingerprinting by Optical Mapping, A Simple Approach

Rapidly fingerprinting of eukaryotic chromosomes, using the fluorescence intensity measurement methodology described herein can be accomplished by the present invention without any hybridization. For example, the steps involved in analyzing YAC fingerprints are described: Yeast bearing YACs are incorporated into gel inserts (3, 55), and their DNAs separated using pulsed field electrophoresis in low gelling temperature agarose. Identified YAC gel bands are cut out and digested with a series of enzymes, in separate tubes or together. Mounting and fixation techniques are chosen from the ones described in this proposal. Preferably magnesium ions are used to fix small molecules onto the slide after extracting the DNA from the gel band using standard techniques. Size distributions are determined from fluorescence intensity measurements as described herein.

The fingerprints produced by a series of different restriction enzymes ranging from frequent to rare cutters, are evaluated to assess contig formation and ordering. YACs are digested using traditional bulk methods, and their fragments imaged and analyzed serially on the microscope. In fact, a robot could also be programmed to produce slides for the microscope, if desired.

Rapid Production of Ordered Chromosome Restriction Maps

Since Chromosomes have left and right arms, chromosomal polarity can be established on single molecules by appropriate hybridization to a distal most unique sequence and imaging the resulting hybrid (9). Adaptation of Smith-Birnsteil partial digestion analysis (113) can be used to rapidly maps Chromosomes using the techniques of optical mapping.

Optical Mapping of Large Mammalian Genomes

Ferrin and Camerini-Otero (68) have shown that two RARE sites can be designed to selectively cleave a sizable mammalian genomic stretch; it can then be resolved on a pulsed field gel from uncut genomic DNA. These authors, as well as Koob and Szybalski (67), suggested that these dissected and isolated genomic sections could be used to construct locus-specific libraries for physical mapping studies. These libraries help in tying contigs together or in mapping uncloneable regions, for example. Although directly mapping the small amount of cleaved, genomic DNA obtained from gels would be convenient, obviating steps and artifacts of cloning, the concentration of the recovered DNA is generally insufficient for direct analysis, except by PCR and optical mapping.

RARE can be used in this invention to dissect large regions from mammalian genomes for further analysis by optical mapping. Human cystic fibrosis (115–117) gene can be used as a test system, along with the same set of RARE oligonucleotides described by Ferrin and Camerini-Otero (68). Using a series of well screened STS (118) markers is another approach (67). However, such analysis are otherwise different. The RARE products are separated from HeLa cell genomic DNA on a pulsed field gel and, based on Southern analysis, determination is made onto where to excise the gel band for optical mapping. The RARE products are not pure but are highly enriched; their purity can be quantitated by Southern hybridization to a series of human probes. For optical mapping the dissected genomic DNA, a battery of 6 and 8 base pair recognition restriction enzymes can be used optical mapping results compared with the detailed, published ones (115–117). The number of molecules needed to complete a restriction map will depend on a number of factors, including the degree of fragment enrichment. RARE-mediated cleavage of an internal fragment, can also be used as a means of optically selecting molecules from unwanted ones.

A Flow-Based mapping System. Flow cytometry depends heavily on flow to accomplish its aims, as the name implies, and decades of efforts have been invested in perfecting flow systems to accommodate different types of samples (119, 120). But a drawback in flow cytometry is that large naked DNA molecules cannot be routinely sorted, although chromosomes can be. This is understandable since large DNAs are very easily broken by shear forces generated in typical flow cytometry instrumentation. Gentle solvent flow fields can be used (e.g., $5 \times 10^{-2}$ nl/sec at 100×20 micron opening) to move large DNA molecules in fluid without any apparent breakage, as discerned by fluorescence microscopy. Solvent flow fields with low rates of shear (shear is the change of solvent velocity with distance across a flow) can be exploited to stretch out and align DNA molecules as big as those contained within mammalian chromosomes (61, 83, 85, 121). Viscoelastic measurement (61, 83, 122) of chromosomally sized DNA molecules rely on flow fields to stretch out long molecules for subsequent relaxation measurement. Solvent flow has also been used by Smith and Bustamante to stretch out tethered lambda bacteriophage DNA concatamers (77). In addition, Yanagida and colleagues used solvent flow to elongate molecules in their pioneering DNA imaging work (44, 81). Gentle flow fields do not break large DNA molecules.

A microscope mounted chamber can be used to simultaneously flow and elongate large DNA molecules, with the following objectives in mind: 1) evaluation of flow chamber characteristics and their effect on DNA stability and elongation, with respect to imaging, 2) control of molecular elongation with flow rate, 3) development of systems to deliver reagents and enzymes to flowing molecules, with concurrent observation of molecular events; adapting our software to image and size flowed molecules; creation of high speed restriction maps using this system.

Flow Chamber Design Fluid

Fluid flow fields and electrical fields have somewhat complementary engineering needs, so that chambers designed utilizing both effects should be robust and flexible. The chamber is designed to liberate DNA molecules embedded in gel; these samples can be gel inserts or excised electrophoresis gel bands. DNA molecules are moved from the gel into a thin space for observation. The flow field accomplishes two operations simultaneously. It moves DNA molecules out of the "extraction area" into the viewing area, and it elongates and positions large DNA molecules in the flow streamlines for optical measurement.

Phased Restriction Maps from Flowed Molecules

To perform optical mapping restriction enzyme or magnesium ions are used to trigger digestion into the flow chamber after the molecule is aligned and elongated in the field to induce cleavage. Controlling these steps is important. The restriction enzyme must be triggered, for example, by the addition of magnesium ions, and then its cutting imaged before the resultant fragments have flowed out of view. Additionally, restriction fragments should retain their relative positions to remain phased. Avoidance of turbulence is important, and the literature is plentiful on flow cytometry techniques to handle such difficulties. If necessary, chambers cam be constructed to produce an accelerating flow rate (easily accomplished with a tapered geometry) so that fragments will separate efficiently when cleaved. Fragment sizes are determined using known and described methods. Large fragments (e.g., >30 kb) are sized using fluorescence intensity ratio, apparent and absolute length, and relaxation measurements performed at flow cessation. Small fragments (e.g., <30 kb) can be sized using the intensity methods described earlier for the gel-fluid interface system and the fluorescence lifetime instrumentation if great sensitivity is needed. Compromises may be made here concerning flow rate, illumination intensity and imaging time, which affects the number of usable gray levels (bit depth).

A less demanding measurement is determining size distributions of restriction digests performed in a test tube. Full digests can yield fingerprints, while partial digests with end-labeled molecules (using beads,) can produce fully ordered maps. If the flowed "in situ restriction digest"

disorders fragments, the map defaults to an unordered, but still useful fingerprint.

Rapid Maps for Human Genome(s)

A main purpose in providing a flow based restriction mapping system is speed and simplified automation of analysis techniques as compared to gel based approaches. The throughput of the flow system described herein can image 5–500 kb molecules/minute; or additionally 5–10 molecules can be imaged in parallel, e.g., 25–5000 kb molecules/minute. In 1 hour, 150 mgb can be processed, which is equivalent to 1.5 human chromosomes. In 24 hours one human genome worth of DNA can be imaged. These numbers compare favorably with the Cohen laboratory YAC fingerprinting throughput of 61 YACs/day/person (11); and this rate only describes the film to computer file stage. The potential high throughput capabilities of the optically based system described here, coupled with its high information content, provides such rapid mapping:

If 500 kb molecules are digested while flowing to produce ordered restriction maps could be made from these fragments with a high degree of confidence, depending upon the number of cuts made per 500 kb fragment and the precision of sizing. Obviously more cuts per 500 kb fragment simply contig formation. The Smith-Birnsteil partial digestion approach discussed previously can also be used in here if there are problems with the flow-and-cut approach. Briefly stated, ordered restriction maps would be invaluable for dependably forming mapped (or fingerprinted) YACs into contigs and determining internal order. Ordered, accurate restriction maps of 500 kb fragment might reduce the number of genome equivalents needed for coverage, due to less overlap needed to for contig assignment. Additionally, these maps are an important resource for any studies concerning genome structure and organization. A good source of genomic DNA might be from flow sorted chromosomes that are partially digested to produce 500 kb overlapping fragments. Here again optical mapping should ideally interface with this relatively meager (in terms of number of DNA molecules) source of DNA. With enough precisely sized fragments generated from a single molecule it is possible to construct contigs without hybridization-fingerprinting because optical mapping can produce data with greater information density than electrophoresis based methods.

In comparison, electrophoretic methods poorly characterize size distributions and requires hybridizations to decompose gel bands consisting of multiple fragment types. It is also not common to run agarose gels and discern 100 separate bands with any clarity. This approach is suitable for whole genome analysis in a global approach, analogous to the Cohen laboratory's largely successful tact in using fingerprinted large YACs.

Ordered restriction maps provide more information than simple fingerprints so that less overlap may be necessary for contig formation (124) than simple unordered restriction fingerprints (125). However, these 500 kb partial digestion fragments can also be fingerprinted more simply by digesting them to produce unordered or partially ordered maps. If necessary such fingerprints could also be augmented with RecA mediated hybridization of sequences such as LINE-1 (11, 126) in the same way these commonly used on Southern blots (11, 38;).

In summary, the medium-based sizing process of this invention involves characterization of molecules using a microscope. Molecules, particularly small or medium-sized molecules, are placed in a medium and mounted on a slide using conventional techniques. Large molecules are mounted on a microscope slide using spermine condensation, which avoids breakage problems. At some point the molecules may be stained. The molecules may be perturbed in the medium by the application of an electrical field. The field is then shut off, allowing the molecules to relax to their equilibrium conformation, which on the average is spherical or ellipsoidal, or to assume a certain position. An image processor connected to a video camera counts the molecules and follows their shape changes. The kinetics of relaxation, reorientation and rotation of the molecules, as well as their length and diameter are calculated automatically, and molecular weights for all of the imaged molecules are calculated from established relationships.

The following examples are offered in order to more fully illustrate the invention, but are not to be construed as limiting the scope thereof.

EXAMPLE 1

Preparing DNA for Microscopy

G bacteria was grown as described by Fangman, W. L., Nucl. Acids Res., 5, 653–665 (1978), and DNA was prepared by lysing the intact virus in ½× TBE buffer (1×: 85 mM Trizma Base (Sigma Chemical Co., St. Louis Mo.), 89 mM boric acid and 2.5 mM disodium EDTA) followed by ethanol precipitation; this step did not shear the DNA as judged by pulsed electrophoresis and microscopic analysis.

DNA solutions (0.1 microgram/microliter in ½× TBE) were diluted (approximately 0.1–0.2 nanogram/al agarose) with 1.0% low gelling temperature agarose (Sea Plague, FMC Corp., Rockport Me.) in ½× TBE, 0.3 micrograms/ml DAPI (Sigma Chemical Co.), 1.0% 2-mercaptoethanol and held at 65° C. All materials except the DNA were passed through a 0.2 micron filter to reduce fluorescent debris. Any possible DNA melting due to experimental conditions was checked using pulsed electrophoresis analysis and found not to be a problem.

EXAMPLE 2

Imaging DNA in a Gel

The sample of Example 1 was placed on a microscope slide. To mount the sample, approximately 3 microliters of the DNA-agarose mixture were carefully transferred to a preheated slide and cover slip using a pipetteman and pipette tips with the ends cut off to reduce Shear. Prepared slides were placed in a miniature pulsed electrophoresis apparatus as shown in FIGS. 1 and 2. All remaining steps were performed at room temperature. Samples were pre-electrophoresed for a few minutes and allowed to relax before any data was collected. Pulsed fields were created with either a chrontrol time (Chrontrol Corp., San Diego, Calif.) or an Adtron data generating board (Adtron Corp., Gilbert, Ariz.) housed in an IBM AT computer and powered by a Hewlett Packard 6115A precision power supply. Field Strength was measured with auxiliary electrodes connected to a Fluke digital multimeter (J. Fluke Co., Everett, Wash.). A Zeiss Axioplan microscope (Carl Zeiss, West Germany) equipped with epifluorescence optics suitable for DAPI fluorescence and a Zeiss 100× Plan Neofluar oil immersion objective was used for visualizing samples. Excitation light was attenuated using neutral density filters to avoid photo-damage to the fluorescently labeled DNA. A C2400 silicon intensified target (SIT) camera (Hamamatsu Corp., Middlesex, N.J.) was used in conjunction with an IC-1 image processing system (Inovision Corp., Research Triangle Park, N.C.) to obtain and process video images from the microscope. Images were obtained continuously at the rate of one every five or six seconds, and as many as 200 digitized images could be stored per time course. Each digitized time-lapse image benefited from the integration of 8 frames obtained at 30 Hz, which was fast enough to avoid streaking due to coil motion. After the time-lapse acquisition was complete, the microscope was brought out-of-focus and a background image was obtained. Each time-lapse image was processed by first attenuating a copy of the background image, so that the average background intensity was 82% of the average time-lapse image intensity. The attenuated background was subtracted from the time-lapse image and the resultant image was then subjected to a linear-stretch contrast enhancement algorithm. Photographs of the processed images were obtained using a Polaroid Freeze Frame video image recorder (Polaroid Corp., Cambridge, Mass.).

EXAMPLE 3
Perturbing Molecules in a Gel

The molecules of Example 2 were perturbed by POE. POE was accomplished by using a series of relatively short normal pulses of a chosen ratio and then after a longer time period, the polarity of one of the fields was switched. The switch time and normal field ratio are analogous to the pulsed electrophoresis variables of pulse time and field angle.

The nomenclature used to describe a POE experiment is as follows: 3,5–80 second pulses, 3 volts/cM). "3,5–80 seconds" means a 3 second pulse south-north, followed by a 5 second pulse east-west; after 80 seconds of this 3,5 second cycle, the polarity of the 5 second pulse is changed (west-east) for another 80 seconds, and a zigzag staircase path is defined for the molecules involved. The pulse intensity was 3 volts/cM. In this Example, epifluorescence microscopy was coupled with the POE method to enable the general study of DNA conformational and positional changes during electrophoresis. While the POE method using the adapted microscopy chamber shown in FIG. 2 was used in this experiment, ordinary electric fields switched on and off could have been used. POE offers certain advantages when electric fields are to be applied at different angles, as may be needed to rotate a molecule about its long axis. FIGS. 1 and 2 show diagrams of the adapted POE chamber.

EXAMPLE 4
Observing and Measuring Molecular Relaxation in a Gel

The relaxation of the G bacteriophage DNA of Examples 1–3 was observed after POE was conducted for 600 seconds (3,5–80 second pulses, 3 volts/cm).

The image processor is used to quantify and automate the imaging of the relaxation process, for example, through "feature analysis". Feature analysis works after successive images have been digitized and stored, as shown in FIG. 3(a). The image processor then identifies discrete objects in the images, numbers them, and characterizes them according to shape. For example, the computer determines the effective ellipsoid axes (long and short) for a collection of distorted coils and calculate these features as a function of time as the coil approaches a spherical conformation during the relaxation process. Other types of computerized measurements also can be made to characterize the DNA.

The images displayed in FIG. 5, obtained at 12 second intervals, show the relaxation of several molecules over a 96 second time span. In (a), several coils are shown 3 seconds after the applied field was turned off. The coils appear to relax through the same corrugated staircase path defined by the applied electrical pulses (see molecules marked by arrows) as determined by the limits of microscopic resolution. In (c), a molecule is shown splitting into two, and by (j), all coils have relaxed to a round, unelongated conformation. The bar shown in (j) is 10 microns in length.

EXAMPLE 5
Determining the Molecular Weight of One or More Molecules by Measuring Relaxation Kinetics Molecules of known molecular weight are prepared for imaging according to the procedures of Examples 1–3, and the relaxation time of the molecules is determined by the methods of Examples 1–4. Relaxation time data is collected by imaging and is used to calculate a mathematical relationship between molecular weight and relaxation time of DNA molecules of similar composition. The relaxation time of a sample of molecules of unknown size is then measured, and the size of the molecules is calculated using the mathematical relationship determined on the basis of molecules of known size.

EXAMPLE 6
Determining the Molecular Weight of One or More Molecules by Measuring Reorientation Rate in a Gel Polymers of any size, but particularly those that are too small to image (less than approximately 0.1 micron), are sized in a matrix such as agarose or polyacrylamide gel by measuring the reorientation rate as induced by an applied electrical field. Although a reorientation measurements could be done in free solution, a matrix is preferred because it prevents unnecessary polymer convection and movement. Additionally the presence of a matrix may enhance the size sensitivity, partly because the orientation mechanism is different. POE is particularly useful for measuring reorientation time because of its experimental versatility and very high size resolution of perhaps 15 to 20 megabases. Stiff polymers such as DNA molecules (sized less than 150 base pairs) exist in solution as rods and the rotational diffusion coefficient (the friction felt by the rod as you try to spin about its long axis) varies as M3. Using microscopy, molecules which are large enough to be imaged are visualized, and their reorientation time is determined from the images. For any size of molecules, particularly those which are too small to visualize, the reorientation time of each rod in the field of view is preferably measured by spectroscopic methods. Two such methods are described in detail below, namely fluorescence dichroism and birefringence:

1) A chromophore that binds in a sterically predictable way (ethidium bromide intercalates into DNA molecules) is attached to a polymer molecule. Polarized radiation is used to excite the chromophore. Measuring the total fluorescence intensity temporally provides orientation information of each molecule. The fluorescence radiation of each molecule in the microscope field is measured using a sensitive microchannel plate detector.

2) The orientational dynamics of a molecule is followed with birefringence measurements. Birefringence techniques measure the change of refractive index, which is easily correlated with the orientation of macromolecules in solution or in a matrix. Birefringence measurements are taken while the DNA molecules are undergoing gel electrophoresis. When an electrical field is applied, the DNA molecules stretch out and align with the field, thereby changing the refractive index. By measuring the change of birefringence with time, it is possible to understand details of DNA blob train motion as the molecule orients with the applied electrical field.

Figure 3B:
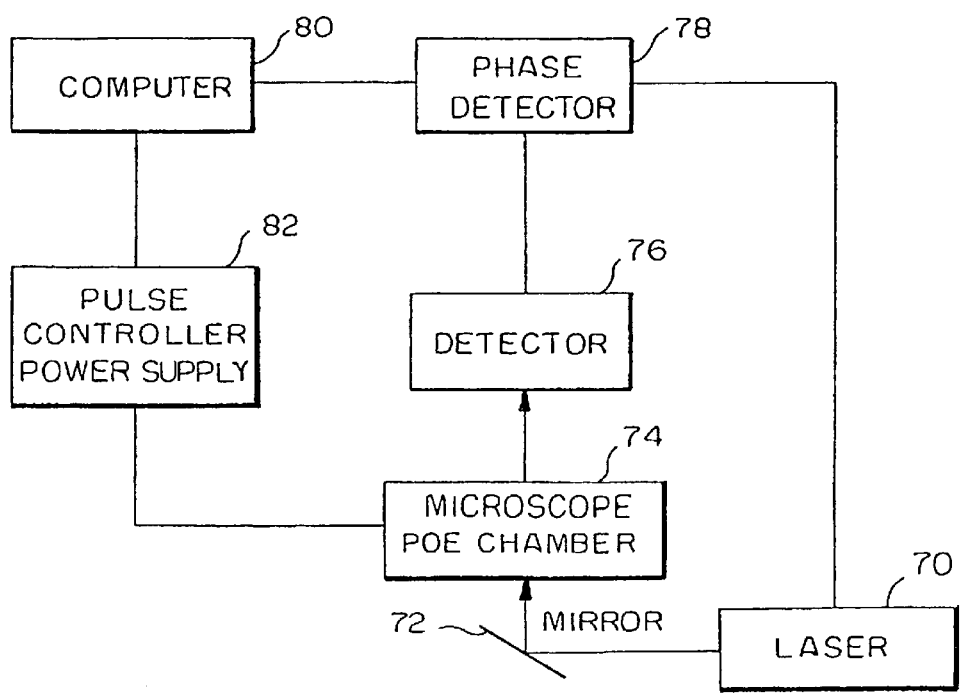

More specifically, birefringence measurements are made by determining the phase difference of two orthogonally polarized planes of laser radiation (red light) differing by a small frequency difference (supplied by the two frequency laser). As the molecules align with the applied electrical field (in the POE chamber), which is generated by pulse controller 82, the refractive index changes with molecular alignment. Light is detected by detector 76, and results in a phase difference in the transmitted radiation, which is measured by the phase detector 78 (FIG. 3(b)) by comparing the value to a standard, sourced at laser 70. The phase difference data obtained as a function of time (the period of field application) is digitized and stored on computer 80 for later retrieval and analysis.

The instrument depicted in FIGS. 1 and 2 applies the necessary fields to cause molecular reorientation. Many different rotational schemes can be described to optimally size molecules in the field. For example, the rotating field frequency can be swept to find resonant frequencies with the polymer sample.

EXAMPLE 7

Determining the Molecular Weight of One or More DNA Molecules by Measuring the Rotation Time of the Molecules in a Gel Molecules in the shape of rods or stiff coils are prepared and observed as in Examples 1–4, except that an acrylamide, rather than agarose gel optionally may be used.

The rate of rotation of a coil or a rod is measured with a microscope-based system using any one of the techniques described above in Example 6. Measurements are made of a sinusoidally varying signal as the molecule spins about its center. The sinusoidal signal is used to determine the polymer size or molecular weight by fitting the period of the sinusoidal signal to the rotational frictional coefficient, which varies as the cube power of the rod length. In other words, the measured angular velocity as measured from the sinusoidal signal (radians/sec.) varies as the rod length cubed in free solution (Boersma, S. (1960) J. Chem Phys. 32:1626–1631, 1632–1635).

The conditions for a proposed series of experimental runs, with constant t, are shown below.

| M<br>Molecular Size<br>(base prs or<br>kilo bases) | E<br>Electric Field<br>Strength<br>(volt/cm) | $\Delta t$<br>Duration of<br>each Pulse<br>(Sec) | $\theta_i$<br>Incremental<br>angle (in<br>clockwise<br>direction<br>(Deg.) |
|---|---|---|---|
| 50 bp | 5 | $1 \times 10^4$ | 10 |
| 150 bp | 5 | $1 \times 10^4$ | 10 |
| 50 kb | 5 | 1 | 10 |
| 500 kb | 5 | 5 | 10 |
| 500 kb | 5 | 900 | 10 |

Thus, in the first example, pairs, triplets or other sets of pulses of 5 volts/cm are successively applied for 0.1 millisecond in opposite directions, with the direction of the first of each successive set of pulses increasing by 10 degrees in a clockwise direction away from the starting point.

Molecules of known molecular weight are placed in a gel, and their rotation rate is determined when the above-described electric fields are applied. Rotation time data is collected and is used to calculate a mathematical relationship between molecular weight and rotation time of G bacteriophage DNA molecules in a particular gel. The rotation time of molecules of unknown size is then measured, preferably using a similar electric field, and the size of the molecules is calculated using the mathematical relationship determined on the basis of molecules of known size.

EXAMPLE 8

Determining the Molecular Weight of One or More Molecules by Measuring Curvilinear Length of DNA Molecules in a Gel The procedure of Examples 1–4 is followed for molecules of known molecular weight. Measurements of the curvilinear length of the molecules while they are in a perturbed state is collected by visualizing the molecules and is used to calculate a mathematical relationship between molecular weight and length. The curvilinear length of perturbed molecules of similar composition and unknown size is then measured using the procedures of Examples 1–4, and the size of the molecules is calculated using the mathematical relationship determined on the basis of molecules of known size. FIGS. 4 and 5 show perturbed molecules for which curvilinear length measurements can be made.

EXAMPLE 9

Determining the Molecular Weight of One or More Molecules by Measuring Diameter of DNA Molecules in a Gel The procedure of Examples 1–4 is followed for molecules of known molecular weight, except that measurements are made when the molecules are in a completely relaxed state. Measurements of the diameter or diameters of the substantially spherical or ellipsoidal G bacteriophage DNA molecules are collected and are used to calculate a mathematical relationship between molecular weight and diameter of G bacteriophage DNA molecules in the gel. The diameter of molecules of unknown size is then measured, and the size of the molecules is calculated using the mathematical relationship determined on the basis of molecules of known size. FIGS. 4(a) and 5(j) show relaxed molecules for which diameter measurements can be made.

EXAMPLE 10

Preparing Large DNA Molecules for Imaging

Chromosomal DNA molecules from *Saccharomyces cerevisiae* were prepared and isolated using the insert method and pulsed electrophoresis. Low gelling temperature agarose gel (FMC Corp. Rockland Me.) was used for preparation to permit relatively low temperature melting. Since UV radiation can break DNA molecules, desired bands were cut out of the gel, guided by ethidium stained flanking edge sections that were cut out of the gel, guided by ethidium stained flanking edge sections that were cut out of the gel, which were then photographed on a 301 nm transilluminator apparatus. The bands were then weighed and equilibrated with a 10-fold excess of 10 mM spermine in water for 3 hours at room temperature. Spermine requires a very low ionic strength environment to condense DNA and, fortunately, the buffers used in electrophoresis are low ionic strength, thus eliminating the need for an equilibration step. The equilibrated samples were then melted in an oven at 74° C. for two hours and after melting. DAPI (1 microgram/ml) and 2-mercaptoethanol (1%) were added. 3 microliters of the melted agarose/DNA mixture were carefully applied to a pre-heated microscope slide and a cover slip was placed on top before the mixture gelled. The slide was then viewed using a Zeiss Axioplan epifluorescence microscope fitted with a 100× Plan Neofluar objective and showed small intensely bright balls which could be decondensed by the addition of salt, through the edges of the coverslip sandwich.

As mentioned above, spermine is particularly useful in an environment of low ionic strength. On the other hand, if DNA molecules are placed in a highly ionic environment, the same type of condensation effect are accomplished with alcohol. Neither of these examples are to be construed as limiting the scope of the invention.

EXAMPLE 11
Restriction Mapping *Schizosaccharomyces pombe* Chromosomal DNA Molecules The DNA of *Schizosaccharomyces pombe*, a fungus with a genome size of about 17–19 megabases distributed on three chromosomes 3, 6 and 8–10 megabases in size, is prepared for microscopy by condensation and uncollapsing, according to the method of Example 10. The 3–5 microliter agarose mixture contains approximately 0.1 nanograms of DNA, 0.5% b-mercaptoethanol, 1 microgram/ml DAPI, 100 micrograms/ml bovine serum albumin (acetylated; Bethesda Research Laboratories, Gaithersburg, Md.) and 10–20 units of an appropriate restriction enzyme. This mixture is briefly held at 37° C. and carefully deposited on a microscope slide and then topped with a coverslip. Prior to digestion with restriction enzymes the DNA is stretched by one of two ways: (1) the liquid slide/agarose/coverslip sandwich is optionally sheared slightly by moving the coverslip or (2) an electrical field is applied using, for example, the POE instrument described in FIG. 3. A 10 mM magnesium chloride solution is then diffused into the sandwich once the gel has set. When the magnesium ions reach the DNA/enzyme complex, the enzyme cleaves the DNA molecule.

The positions of the restriction cutting sites are determined by following the DNA strand from one end to the other using the microscope setup and noting cut sites. These sites appear as gaps in the strand, which is continuous before enzymatic digestion. The size of each of the fragments is then determined by the microscopic methods of this invention, including, (1) measuring the curvilinear length of each fragment, (2) allowing the fragments to relax and measuring their diameter, (3) perturbing the conformation of each fragment with an applied electrical field or flow field (as generated by moving solvent through a gel) and measuring the relaxation kinetics with direct visual detection of conformational and positional changes or microscopy combined with spectroscopy. Direct visual observation is preferred for larger molecules, while the other methods are well suited for fragments too small to image.

The resulting sample when viewed using a fluorescence microscope shows a number of bright balls of three different sizes, with diameters varying as M.33, which is based upon the formula for the volume of a sphere, 4/3R3. The gel also contains a restriction enzyme which is active only when magnesium ions are present.

EXAMPLE 12
In situ Hybridization of Nucleic Acid Probes to Single DNA Molecules Nucleic acids are prepared for microscopy as described in Examples 1–4 above. The agarose medium containing the nucleic acid molecules also contains labeled probes and a recombinational enzyme, recA, which mediates strand displacement of the target molecule by the probe. Strand displacement and pairing occurs by D-looping (see Radding, C., *Ann. Rev. Genet.* 16:405–37 (1982)). ATP and magnesium ions are added to begin the reactions. These ingredients are diffused into the slide/gel/coverslip sandwich as described in Example 11. The reaction is incubated at 37° C. Many different target molecules are simultaneously analyzed, using probes with different labels.

Variations of the method of this invention other than those specifically described above are within the scope of the invention. For example, other parameters of the molecules can be measured, and various type of microscopes and spectroscopic equipment may be used. The pulsing routines for effecting molecule rotation can be varied. Combinations of the above-described techniques are also contemplated. For example, combinations of various types of external forces, mediums and spectroscopic techniques are within the scope of the invention. Furthermore, a measuring technique may be repeated several times, and the measurements from each trial may be averaged.

Figure 6:
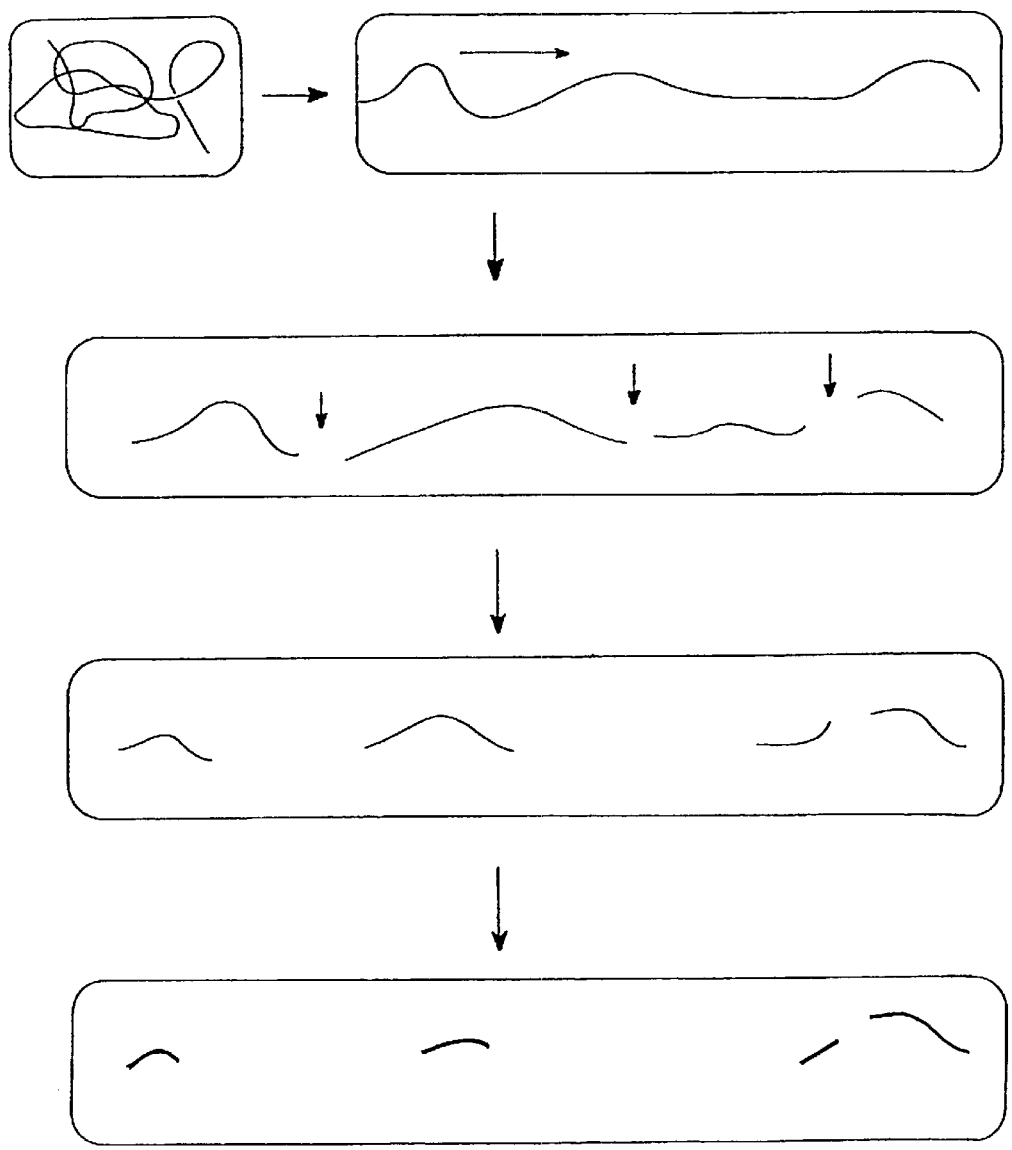
FIG. 6 shows optical mapping, where DNA molecules and restriction enzyme are dissolved in molten agarose without magnesium ions. The DNA molecules are elongated by the flow generated when the mixture is sandwiched between a slide and coverslip. Stretched molecules are fixed in place by agarose gelation. Magnesium ion diffusion into the gel triggers digestion and cleavage sites appear as growing gaps as the molecular fragments relax.

EXAMPLE 13
Ordered Restriction Maps of *Saccharomyces Cerevisiae* Chromosomes Constructed by Optical Mapping Optical mapping (e.g., as shown in FIG. 6), images are made stained, single, deproteinized DNA molecules during restriction enzyme digestion, allowing direct, ordered mapping of restriction sites. In brief, a flow field (or, in principle, other kinds of electrical field) is used to elongate DNA molecules dissolved in molten agarose and fix them in place during gelation.

As a non-limiting example, yeast chromosomal DNA (yeast strain AB972) was resolved by pulsed electrophoresis (Schwartz et al., *Cell* 37:67 (1984)) using 1.00% Seakem low melting agarose (FMC), ½×TBE(42.5 mM Trizma base, 44.5 mM boric acid, 1.25 mM disodium EDTA). Cut gel bands were repeatedly equilibrated in TE (10 mM Tris-Cl, 1 mM EDTA, pH 8.0). The gel embedded, purified chromosomes were then equilibrated overnight at 4° C. in magnesium-free restriction buffer containing 0.1 mg/ml acetylated bovine serum albumin, 1% β-mercaptoethanol, 0.1% Triton X-100 (Boehringer Manheim, membrane quality), and 0.2 µg/ml 4', 6-diamino-2 phenylindole dihydrochloride (DAPI) with slow shaking. Equilibrated samples ranging in volume from 50 to 100 µl were melted at 72° C. for 5 minutes, and then cooled to 37° C. Approximately 0.3–0.5 ul of enzyme (2 to 14 units/µl) was spread on a slide. Enzyme reaction temperatures were as recommended by manufacturers. β-mercaptoethanol was added to discourage photolysis M. Yanagida et al. in *Applications of Fluorescence in the Biomedical Sciences*, D. L. Taylor et al., Eds. (Alan R. Liss, New York, 1986), pp. 321–345. and was tested at this concentration for any deleterious effects on digestion using electrophoresis. A 7 µl volume of the melted sample was typically pipetted (slowly) using a wide bore pipette tip onto an 18×18 mm cover glass and rapidly deposited onto a slide. Timing and quenching of the gel is critical for controlling elongation. The reaction chamber was then sealed with mineral oil to avoid evaporation, and the agarose was allowed to gel for at least 30 minutes at 4° C., prior to diffusion of 50 mM MgCl2 through an open space. For chromosome I(240 kb) and III (345 kb), slides were in a cold desiccator (4°) prior to casting to hasten gelling avoiding premature molecular relaxation. For the larger chromosomes, which relax more slowly, slides were kept at room temperature. The slide was placed on a temperature controlled microscope stage at 37° C. (except CspI, 30° C.). The gelatin process restrains elongated molecules from appreciably relaxing to a random coil conformation during enzymatic cleavage. A restriction enzyme is added to the molten agarose-DNA mixture and cutting is triggered by magnesium ions diffused into the gelled mixture (mounted on a microscope slide). Cleavage sites are visualized as growing gaps in imaged molecules. DNA molecules were imaged using a Zeiss Axioplan or Axiovert 135 microscope equipped for epi-fluorescence (487901 filter pack for UV excitation and Blue emission) and a 100× or 63× Plan-Neofluar objective (Zeiss) coupled to Hammamatsu C2400 SIT cameras. Care was taken to adjust the camera controls to avoid saturating the digitizer at either end of the intensity range. Every 20 seconds, 32 video frames were digitized to 8 bits and integrated to give 13 bit precision by a Macintosh based Biovision image processor or a Pixel pipeline digitizer (Perceptics Corp.). A computer controlled shutter was used to limit illumination to 1.5 seconds per image giving a total of about 135 to 255 seconds for typical experiments. Neutral density filters were used to keep the illumination intensity below 100 µW measured at the objective. Control experiments showed no damage to DNA molecules under these conditions. Digitized images were recorded directly to disk and archived on tape. The resulting fragments are sized in two ways: by measuring the relative fluorescence intensities of the products, and by measuring the relative apparent DNA molecular lengths in the fixating gel. Maps are subsequently constructed by simply recording the order of the sized fragments. Length and relative fluorescence intensity were calculated to 16-bit precision using a modified version of NIH Image for Macintosh by Wayne Rasband, available upon request from the authors (e-mail huff@mcclb0.med.nyu.edu). Briefly, the original unprocessed image was displayed in an enlarged format and an overlay image was prepared by manually tracing the DNA. The length map was made directly from this overly. For intensity calculations, the 13-bit raw data image was smoothed and the overlay image was dilated five times to cover all foreground pixels. For each pixel marked on the overlay, a synthetic background value was calculated as the weighted average of surrounding pixels, with a weight that decreased with distance, but was zero for all marked pixels. These values are intended to approximate those which would have been measured had the DNA been absent. The intensity of a particular DNA fragment was the sum of all pixels of the fragment minus the matching background pixels. The are of the fragment was the original overlay dilated twice. This process was repeated for each frame of raw data which had an overlay image, excluding those with poor focus. Intensity results were averaged for five images following a cut, and the relative sizes of the two fragments were calculated as $x/(x+y)$ and $y/(x+y)$. If fragment y later cuts into u and v, then $(y/(x+y))(u/(u+v))$ is used for the size of u. The resulting numbers constitute a single sample for the purposes of subsequent analysis. Averaging a small number of molecules rather than utilizing only one improves accuracy and permits rejection of unwanted molecules. The samples were averaged and the 90% confidence interval on the mean was calculated using the t distribution with n−1 d.f. and the sample standard deviation. This calculation is valid if the data represent random samples from a normal distribution. There is a 90% chance that the population mean falls within the confidence interval. For chromosome I, the reported confidence interval was found by taking the lower bound from the short fragments and upper bound from the long fragments. The 90% confidence interval for the population standard deviation was calculated using the sample standard deviation, the number of samples, and the chi-square distribution with n−1 d.f. The midpoint of this interval was used to estimate the population standard deviation. The coefficient of variation (CV) is the estimated population standard deviation divided by the sample mean. The pooled standard deviation is the square root of the average of the variances. The relative error is the differences between our value and the reported value divided by the reported value. Optical map production is very rapid because of the combination of restriction fragment ordering in real time with fast accurate sizing techniques. Optical mapping is a powerful new technology for rapidly creating ordered restriction maps of eucaryotic chromosomes or YACs, without the need for analytical electrophoresis, cloned libraries, probes, or PCR primers. Incremental technical improvements should enable the rapid high resolution mapping of mammalian chromosomes and ordering of YACs.

Gel fixation and mechanics of DNA relation under tension and cleavage. A single large DNA molecule 200 µm long (600 kb) is a random coil in solution which can be visualized as a loosely packed ball averaging 8 µm across (Roberts, 1975). Optical mapping begins with stretching out such a DNA molecule and fixing it in place to inhibit rapid relation, prior to imaging by light microscopy. The fixed molecule must lie within a shallow plane of focus for successful imaging. Elongated molecules in a gel behave mechanically like a stretched spring (Schwartz, Koval, 1989): fixed molecules are under tension which is released during coil relaxation to a random conformation. However, excess fixation is undesirable for optical mapping, since restriction cleavage sites must relax to be detected and imaged as growing gaps.

Zimm (Zimm, 1991) has modeled DNA molecules embedded in agarose gel, during electrophoresis, as a series of connected pools of coil segments under tension with each other, and calculates that the force (fi) associated with the free energy change of shuttling coil segments between pools is given by $fi = 3\ kT/(2\ nib)((a2/nib2)-1)+(kT/b)\ln C$, (Chumakov, Nature 359,380 1992) where k is the Boltzmann constant, a is the gel pore diameter, n is the number of associated coil segments, b is the coil segment length, T is the temperature and C is a constant relating to coil segment structure. This result shows that the tension developed between pools is inversely related to the number of segments contained with a pore volume (Eq.1). It follows that a stretched our, elongated molecule is under more tension than a compact, relaxed one.

Large DNA molecules can be stretched out in molten agarose by flow forces and then rapidly fixed in place by agarose gelation, without application of electrical fields. Yeast chromosomal DNA (yeast strain AB972) was resolved by pulsed electrophoresis (D. C. Schwartz and C. R. Cantor, Cell 37,67 (1984)) using 1.00% Seakem low melting agarose (FMC), ½× TBE(42.5 mM Trizma base, 44.5 mM boric acid, 1.25 mM disodium EDTA). Cut gel bands were repeatedly equilibrated in TE (10 mM Tris-Cl, 1 mM EDTA, pH 8.0). The gel embedded, purified chromosomes were then equilibrated overnight at 4° C. in magnesium-free restriction buffer containing 0.1 mg/ml acetylated bovine serum albumin, 1% β-mercaptoethanol, 0.1% Triton X-100 (Boehringer Manheim, membrane quality), and 0.2 µg/ml 4',6-diamino-2 phenylindole dihydrochloride (DAPI) with slow shaking. Equilibrated samples ranging in volume from 50 to 100 µl were melted at 72° C. for 5 minutes, and then cooled to 37° C. Approximately 0.3–0.5 ul of enzyme (2 to 14 units/µl) was spread on a slide. Enzyme reaction temperatures were as recommended by manufacturers. β-mercaptoethanol was added to discourage photolysis M. Yanagida et al. in *Applications of Fluorescence in the Biomedical Sciences*, D. L. Taylor et al., Eds. (Alan R. Liss, New York, 1986), pp. 321–345. and was tested at this concentration for any deleterious effects on digestion using electrophoresis. A 7 µl volume of the melted sample was typically pipetted (slowly) using a wide bore pipette tip onto an 18×18 mm cover glass and rapidly deposited onto a slide. Timing and quenching of the gel is critical for controlling elongation. The reaction chamber was then sealed with mineral oil to avoid evaporation, and the agarose was allowed to gel for at least 30 minutes at 4° C., prior to diffusion of 50 mM MgCl2 through an open space. For chromosome I(240 kb) and III (345 kb), slides were in a cold desiccator (4°) prior to casting to hasten gelling avoiding premature molecular relaxation. For the larger chromosomes, which relax more slowly, slides were kept at room temperature. The slide was placed on a temperature controlled microscope stage at 37° C. (except CspI, 30° C.). Experimentally, the kinetics of gelation are controlled by temperature, and optimization of the annealing conditions. For our analysis, DNA coils must be critically stretched: too much and molecule becomes difficult to image; too little, and there is insufficient tension to reveal cut sites. Yeast chromosomal DNA (yeast strain AB972) was resolved by pulsed electrophoresis (D. C. Schwartz and C. R. Cantor, Cell 37,67 (1984)) using 1.00% Seakem low melting agarose (FMC), ½× TBE(42.5 mM Trizma base, 44.5 mM boric acid, 1.25 mM disodium EDTA). Cut gel bands were repeatedly equilibrated in TE (10 mM Tris-Cl, 1 mM EDTA, pH 8.0). The gel embedded, purified chromosomes were then equilibrated overnight at 4° C. in magnesium-free restriction buffer containing 0.1 mg/ml acetylated bovine serum albumin, 1% β-mercaptoethanol, 0.1% Triton X-100 (Boehringer Manheim, membrane quality), and 0.2 μg/ml 4',6-diamino-2 phenylindole dihydrochloride (DAPI) with slow shaking. Equilibrated samples ranging in volume from 50 to 100 μl were melted at 72° C. for 5 minutes, and then cooled to 37° C. Approximately 0.3–0.5 μl of enzyme (2 to 14 units/μl) was spread on a slide. Enzyme reaction temperatures were as recommended by manufacturers. β-mercaptoethanol was added to discourage photolysis M. Yanagida et al. in *Applications of Fluorescence in the Biomedical Sciences*, D. L. Taylor et al., Eds. (Alan R. Liss, New York, 1986), pp. 321–345. and was tested at this concentration for any deleterious effects on digestion using electrophoresis. A 7 μl volume of the melted sample was typically pipetted (slowly) using a wide bore pipette tip onto an 18×18 mm cover glass and rapidly deposited onto a slide. Timing and quenching of the gel is critical for controlling elongation. The reaction chamber was then sealed with mineral oil to avoid evaporation, and the agarose was allowed to gel for at least 30 minutes at 4° C., prior to diffusion of 50 mM MgCl2 through an open space. For chromosome I(240 kb) and III (345 kb), slides were in a cold desiccator (4°) prior to casting to hasten gelling avoiding premature molecular relaxation. For the larger chromosomes, which relax more slowly, slides were kept at room temperature. The slide was placed on a temperature controlled microscope stage at 37° C. (except CspI, 30° C.). Excessively stretched molecules present too little fluorochrome per imaging pixel, so that measured molecular intensities approach background values. Additionally, the fixation process has to be gentle enough to permit some coil slippage to reveal cut sites. Taking these and other considerations into account, our fixation conditions were optimized to produce molecules spanning approximately 20% of their curvilinear contour lengths.

How DNA molecules are entrapped by agarose gelation is not known. Imaged, stretched molecules show bright round pools of coil at their ends, evidence of chain relaxation (FIGS. 8, 10). The pool sizes range from 1–3 μm. Segmental pools are also observed to form internally, and then disappear, as local pockets of coil tension equilibrate with each other. As a DNA molecule relaxes within the train of contiguous gel pores it spans, the segmental density increases, and segments can even be seen to spill over into neighboring pore spaces. The detailed relaxation mechanism is a complex one (de Gennes, et al., Scaling Concepts in Polymer Physics, Cornell University Press, 1979). Gaps appear because a molecule experiences an effective tension since the configurational entropy of the elongated polymer is lower than that of the relaxed state. On a simple descriptive level, the process can be compared to watching the relaxation of a stretched-out thick rubber band encased in a tight tube, with holes in the sides. Cleavage accelerates relaxation by creating new ends within a molecule, and possibly also by causing a mechanical perturbation that releases trapped fragments from local energy minima.

A high numerical aperture microscope objective can produce bright, high contrast images of stained DNA molecules, but with a very shallow depth of focus. Experimentally, for a long molecules to be in focus, it must lie within a plane approximately 0.2 μm thick. Our method of gel fixation reproducibly allows visualization of molecules that are within this 0.2 micron tolerance as measured optically. This remarkable degree of optical flatness results from a laminar, parabolic fluid flow pattern generated between the glass surfaces, prior to gelation. Furthermore, dissolved agarose and DNA molecules may potentiate this effect by facilitating laminar flow, while preventing onset of turbulence (Atkins, 1992).

Finally, gel fixation of large DNA molecules is convenient enough to be broadly applicable to other systems, especially when biochemical reactions can be coupled to visualizable events.

Restriction Digestion of Single Molecules. Optical mapping detects restriction enzyme cleavage sites as gaps that appear in a fixed molecule as fragments relax to a more random conformation (FIGS. 13,15). Since the rates of enzymatic cleavage by different restriction enzymes are variable (Wells, et al., Genetics 127,681, 1981), careful adjustment of the timing is critical. Cleavage should occur only after molecular fixation is complete because premature reactions disrupt attempts to phase fragments. This timing problem was solved by premixing the agarose-DNA solution with restriction enzyme, at 37° C., and triggering the reaction by diffusing magnesium ions into the viewing field, without disturbing the gel. Yeast chromosomal DNA (yeast strain AB972) was resolved by pulsed electrophoresis (D. C. Schwartz and C. R. Cantor, Cell 37,67 (1984)) using 1.00% Seakem low melting agarose (FMC), ½× TBE(42.5 mM Trizma base, 44.5 mM boric acid, 1.25 mM disodium EDTA). Cut gel bands were repeatedly equilibrated in TE (10 mM Tris-Cl, 1 mM EDTA, pH 8.0). The gel embedded, purified chromosomes were then equilibrated overnight at 4° C. in magnesium-free restriction buffer containing 0.1 mg/ml acetylated bovine serum albumin, 1% β-mercaptoethanol, 0.1% Triton X-100 (Boehringer Manheim, membrane quality), and 0.2 μg/ml 4', 6-diamino-2 phenylindole dihydrochloride (DAPI) with slow shaking. Equilibrated samples ranging in volume from 50 to 100 μl were melted at 72° C. for 5 minutes, and then cooled to 37° C. Approximately 0.3–0.5 ul of enzyme (2 to 14 units/μl) was spread on a slide. Enzyme reaction temperatures were as recommended by manufacturers. β-mercaptoethanol was added to discourage photolysis M. Yanagida et al. in *Applications of Fluorescence in the Biomedical Sciences*, D. L. Taylor et al., Eds. (Alan R. Liss, New York, 1986), pp. 321–345. and was tested at this concentration for any deleterious effects on digestion using electrophoresis. A 7 μl volume of the melted sample was typically pipetted (slowly) using a wide bore pipette tip onto an 18×18 mm cover glass and rapidly deposited onto a slide. Timing and quenching of the gel is critical for controlling elongation. The reaction chamber was then sealed with mineral oil to avoid evaporation, and the agarose was allowed to gel for at least 30 minutes at 4° C., prior to diffusion of 50 mM MgCl2 through an open space. For chromosome I(240 kb) and III (345 kb), slides were in a cold desiccator (4°) prior to casting to hasten gelling avoiding premature molecular relaxation. For the larger chromosomes, which relax more slowly, slides were kept at room temperature. The slide was placed on a temperature controlled microscope stage at 37° C. (except CspI, 30° C.). Aside from gaps, cleavage is also signaled by the appearance of bright condensed pools or "balls" of DNA on the fragment ends at the cut site. These balls form shortly after cleavage and result from coil relaxation which is favored at ends (FIGS. 13,15). This pooling of segments is useful in map making because it helps to differentiate out-of-focus segments, that might appear as gaps, from actual cuts. Cleavage is scored more reliably by both the appearance of growing gaps and enlarging bright pools of segments at the cut site.

Map Construction—Fragment Number Determination

Large scale restriction maps have been constructed primarily from electrophoretically derived data. A new set of approaches has been developed to size and order fragments on samples that can consist of single DNA molecules, using microscope based techniques. The first step is to determine the number of cleavage sites within a molecule. The cut sites within a molecule tend to appear at irregular times after $Mg^{2+}$ addition. All possible cleavage sites do not appear simultaneously; instead, cuts usually appear within 5 minutes of each other, under the conditions described here. The extent of digestion depends on a number of factors including both the fragment number and size. Digestion results obtained by optical mapping for a selected set of Not I digested yeast chromosomes are displayed in FIG. 7. Fortunately, published Not I restriction enzyme maps are available for all *S. cerevisiae* chromosomes (Link, 1991), enabling reliable benchmarking of the optical mapping methodology.

Figure 7D:
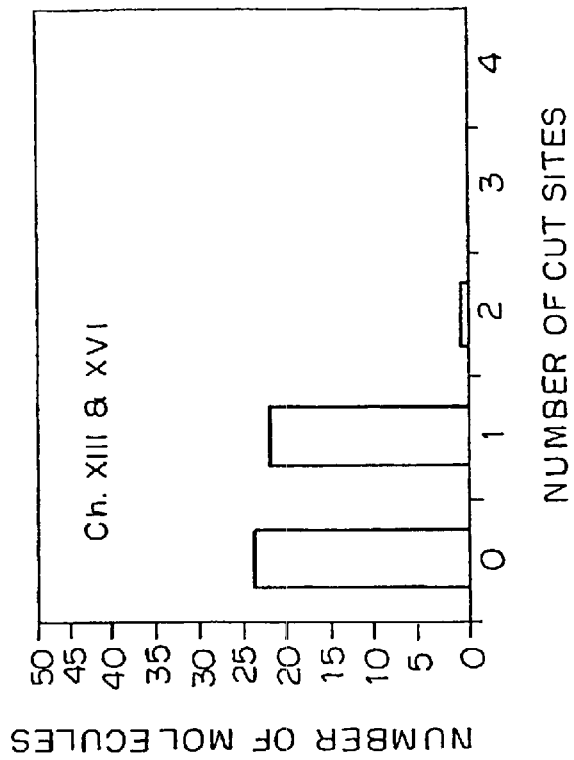
Figure 7C:
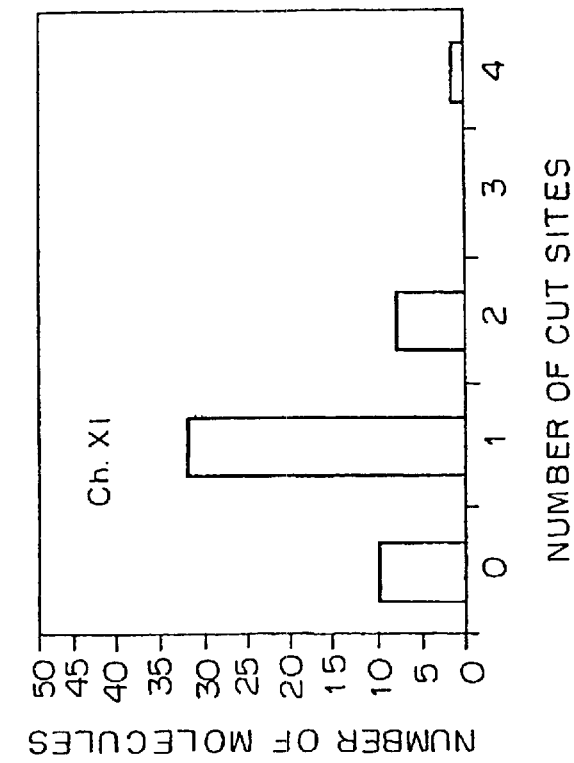

A typical mounted sample contains approximately 3–5 molecules within a single viewing field and overall, roughly 50–95% of them show evidence of one or more cuts by the criteria described here. The histograms in FIG. 7 show that the overall number of cut sites exceeding published results is quite low. The cutting frequency results (FIG. 7B) for chromosome V digested with Not I show that the number of fully cut molecules is approximately half that of all singly cut molecules: the value corresponding to complete digestion is calculated by assuming that an equal distribution of identically sized chromosome V and VIII DNA molecules are present in the mounted sample. The Not I restriction maps for these chromosomes reveal that chromosome V has 3 cut sites, while VIII has only 2. Chromosome XI cutting frequency data (FIG. 7C) is different; 25% of all cut molecules are seen to be fully digested (two cutting sites). An explanation for the apparently lower frequency is that this chromosome produces a 30 kb sized Not I fragment that is more difficult to detect optically than larger fragments. This result is not surprising considering that tension across a cut is probably fragment size dependent, so that smaller, elongated fragments apply less tension. Furthermore, since coil tension across a cut site is required for its identification, additional cuts will produce fragments that ultimately relax to reduce the overall molecular tension and impede the observation of further cuts. Finally, very large, 1 megabase sized molecules have been spread, such as chromosome XIII and XVI, and these data (FIG. 7D) show that roughly half of the molecules are digested to completion (one cut) in mounts with observable cutting activity.

The maximum number of cuts determined by histogram analysis is the bin containing the largest number of cut sites whose molecules can be properly averaged by intensity and length measurements for size.

Influence of coil relaxation on detection of cuts. Aside from cases involving small fragments, incomplete digestion is seen in all the histograms in FIG. 7. While potential cases range from photo irradiation artifacts to interactions imposed by the current design of the microscope chamber, partial digestion observed here is attributable mostly to incomplete coil relaxation at a given cut site, due to relaxation modes that fail to produce a gap or distinct ball. A variety of different relaxation modes are observed in actual practice, some of which are sketched in FIG. 8. Relaxation modes can both facilitate (8-D) and hinder cut detection (8-H). Application of electric or flow fields might be used to trigger relaxation at such sites and permit their detection. Parallel electrophoresis experiments show essentially complete digestion under similar experimental conditions (Hernandez).

Interestingly, the data for chromosome I show almost complete digestion (95%; see FIG. 7A). Images of chromosome I under digestion (FIG. 13A) reveal that after the expected single cut is observed, only the cut site ends relax and bright pools of segments accumulate at the ends (20 molecules), as interpreted in FIGS. 8B, 8C and 8D, while the remaining ends appear to be fixed in place. Bright pools of relaxed coil segments accumulate at the ends of gel-fixed DNA molecules, as noted above.

Conceivably, the ends of chromosome I embedded in agarose are behaving as a sort of molecular rivet (FIG. 9), reacting to the tension developed between it and the intervening molecular segments to provide ideal mechanical conditions for cut detection. It seems likely that short-range interactions will predominate so that the amount of relaxed coil present at the ends of elongated molecules will not vary much with molecular mass above some threshold in size. Consequently, a relatively short molecule, such as chromosome I, will contain a greater proportion of relaxed coil segments at its end than longer ones, such as chromosomes XIII and XVI.

Fragment Sizing By Relative Intensity. The second step is to size the resulting restriction fragments. For this purpose two complementary approaches can be used, one based on relative fragment fluorescence intensity and the second on apparent relative length measurements. However, neither approach provides absolute values, but each can be standardized readily. Fortunately, the gel fixation technique described above produces a natural substrate for intensity measurements since an entire molecule can be brought into focus. Gel fixation is able to flatten molecules spanning as much as 250 $\mu$m. Segments of molecules that are out of focus cannot be used for intensity measurements because their intensities are not proportional to mass in any simple way. A relevant observation here is that when an elongated molecules substantially relaxes, most of its mass moves out of focus, as expected, since the hydrodynamic diameter of a fully relaxed 700 kb DNA molecule in fluid is 8 $\mu$m while the depth of focus used for imaging molecules under the microscope is approximately 0.2 $\mu$m.

The absolute fluorescence intensity of a DNA fragment in the microscope is determined by many variables, such as the camera gain control and lamp brightness, and therefore is not a desirable quantity to measure. By calculating the relative intensity of two fragments (from the same parental molecule), one of the fragments can serve as an internal intensity reference for the other. Relative intensities are converted to kb by multiplying by the know or independently determined chromosome size. Length and relative fluorescence intensity were calculated to 16-bit precision using a modified version of NIH Image for Macintosh by Wayne Rasband, available upon request from the authors (e-mail huff@mcclb0.med.nyu.edu). Further details are available (manuscript in preparation). Briefly, the original unprocessed image was displayed in an enlarged format and an overlay image was prepared by manually tracing the DNA. The length map was made directly from this overlay. For intensity calculations, the 13-bit raw data image was smoothed and the overlay image was dilated five times to cover all foreground pixels. For each pixel marked on the overlay, a synthetic background value was calculated as the weighted average of surrounding pixels, with a weight that decreased with distance, but was zero for all marked pixels. These values are intended to approximate those which would have been measured had the DNA been absent. The intensity of a particular DNA fragment was the sum of all pixels of the fragment minus the matching background pixels. The area of the fragment was the original overlay dilated twice. This process was repeated for each frame of raw data which had an overlay image, excluding those with poor focus. Intensity results were averaged for five images following a cut, and the relative sizes of the two fragments were calculated as $x/(x+y)$ and $y/(x+y)$. If fragment y later cuts into u and v, then $(y/(x+y))(u/(u+v))$ is used for the size of u. The resulting numbers constitute a single sample for the purposes of subsequent analysis. The optical contour maximization technique can be used to size samples containing a small number of molecules (Guo, Nature 359,783, 1992). FIG. 10A shows intensity values for a series of yeast chromosome Not I restriction fragments measured optically and plotted against published values derived from electrophoresis based measurements (Link, Genetics, 127, 681, 1991). Points close to the diagonal line are in good agreement. Disregarding the chromosome V and VIII results, which were based on low precision (8-bit) intensity data, and disregarding the two short fragments less than 60 kb, the pooled standard deviation is 36 kb (FIG. 5A inset) and the average of the coefficients of variation is 16%, comparable to routine pulsed electrophoresis size determinations. The correlation with published results is excellent: the average of the relative errors is 5% whereas the published errors average 4% (Link, Genetics, 127, 681, 1991). The samples were averaged and the 90% confidence interval on the mean was calculated using the t distribution with n−1 d.f. and the sample standard deviation. This calculation is valid if the data represent random samples from a normal distribution. There is a 90% chance that the population mean falls within the confidence interval. For chromosome I, the reported confidence interval was found by taking the lower bound from the short fragments and the upper bound from the long fragments. The 90% confidence interval for the population standard deviation (FIG. 10 inset graphs) was calculated using the sample standard deviation, the number of samples, and the chi-square distribution with n−1 d.f. The midpoint of this interval was used to estimate the population standard deviation. The coefficient of variation (CV) is the estimated population standard deviation divided by the sample mean. The pooled standard deviation is the square root of the average of the variances. The relative error is the differences between our value and the reported value divided by the reported value. Due in part to the intensity normalization procedure, the precision becomes lower for very small fragments, and size agreement is poor for the 30 and 55 kb measurements. Fluorescence intensity measurements size these fragments at almost twice the established values as described below. Changes in the algorithm for correcting the backgrounds of these measurements and the data collection process should improve the precision significantly.

One test of the validity of relative fluorescence intensity measurements is to monitor the constancy of fragment intensities over a usable range of molecular relaxation conditions. This requirement is most critically tested when restriction fragments differ greatly in size. FIG. 11 shows the results of absolute intensities versus molecular length measurements for three typical sizes. These results show that intensities remain relatively constant over a wide size range despite a 3–4 fold change in measured molecular length. This beneficial effect is attributed in part to the mild fixation conditions, so that Brownian motion can dither the elongated coil along the z-axis; this motion is clearly observed on the live video monitor as digestion proceeds. By averaging frames over a 1 second interval most of the DNA is observed as it moves through the focal plane and within the gel pores.

Fragment Sizing by Relative Apparent Lengths. The physical basis of apparent length measurement is simple: each gel-embedded restriction fragment is assumed to have equal coil density, on the average. That is, each fragment has the same change to be stretched more or less, so a length average created over a number of mounts provides a good measure of relative size. Again, relative apparent lengths are converted to kb by multiplying by the chromosome size. Length and relative fluorescence intensity were calculated to 16-bit precision using a modified version of NIH Image for Macintosh by Wayne Rasband, available upon request from the authors (e-mail huff@mcclb0.med.nyu.edu). Further details are available (manuscript in preparation). Briefly, the original unprocessed image was displayed in an enlarged format and an overlay image was prepared by manually tracing the DNA. The length map was made directly from this overlay. For intensity calculations, the 13-bit raw data image was smoothed and the overlay image was dilated five times to cover all foreground pixels. For each pixel marked on the overlay, a synthetic background value was calculated as the weighted average of surrounding pixels, with a weight that decreased with distance, but was zero for all marked pixels. These values are intended to approximate those which would have been measured had the DNA been absent. The intensity of a particular DNA fragment was the sum of all pixels of the fragment minus the matching background pixels. The area of the fragment was the original overlay dilated twice. This process was repeated for each frame of raw data which had an overlay image, excluding those with poor focus. Intensity results were averaged for five images following a cut, and the relative sizes of the two fragments were calculated as $x/(x+y)$ and $y/(x+y)$. If fragment y later cuts into u and v, then $(y/(x+y))(u/(u+v))$ is used for the size of u. The resulting numbers constitute a single sample for the purposes of subsequent analysis. Then, the apparent lengths of restriction fragments are converted, obtaining good accuracy from as few as 4 molecules. The samples were averaged and the 90% confidence interval on the mean was calculated using the t distribution with n−1 d.f. and the sample standard deviation. This calculation is valid if the data represent random samples from a normal distribution. There is a 90% chance that the population mean falls within the confidence interval. For chromosome I, the reported confidence interval was found by taking the lower bound from the short fragments and the upper bound from the long fragments. The 90% confidence interval for the population standard deviation (FIG. 10 inset graphs) was calculated using the sample standard deviation, the number of samples, and the chi-square distribution with n−1 d.f. The midpoint of this interval was used to estimate the population standard deviation. The coefficient of variation (CV) is the estimated population standard deviation divided by the sample mean. The pooled standard deviation is the square root of the average of the variances. The relative error is the differences between our value and the reported value divided by the reported value. Relative determinations of apparent length were verified against the same set of restriction fragments as in the fluorescence intensity measurements, and these results (FIG. 10B) show a similar average relative error of 16% (excluding the 30 and 90 kb fragments). The pooled standard deviation was 47 kb (FIG. 10B inset), the average of the coefficients of variation was 29%.

Apparent molecular length measurements are more robust than intensity measurements, but are less precise, and consequently require additional measurements to achieve an equivalent degree of accuracy. But good length measurements can be obtained from slightly out-of-focus fragments, whereas blurry, out of focus images will confound intensity based measurements. Size determination of small fragments by length were better than intensity. The 30 kb fragment was sized at 44 kb by length vs. 70 kb by intensity, and the 55 kb fragment was sized at 49 kb vs. 88 kb. Given the limited sample number inherent to optical mapping, having two sizing methods for cross-checking results is extremely important for successful map making.

Map Construction Based on Length and Intensity Measurements. FIG. 12 illustrates three types of ordered restriction maps produced by optical mapping compared with (Link, Genetics 127, 681, 1991). The bars shown correspond to sizing analysis results of the Not I restriction fragment as plotted in FIG. 10. FIG. 13 shows selected processed fluorescence micrographs of different yeast chromosomal DNA molecules digested with Not I. Yeast chromosomal DNA (yeast strain AB972) was resolved by pulsed electrophoresis (D. C. Schwartz and C. R. Cantor, *Cell* 37:67 (1984)) using 1.00% Seakem low melting agarose (FMC), ½× TBE(42.5 mM Trizma base, 44.5 mM boric acid, 1.25 mM disodium EDTA). Cut gel bands were repeatedly equilibrated in TE (10 mM Tris-Cl, 1 mM EDTA, pH 8.0). The gel embedded, purified chromosomes were then equilibrated overnight at 4° C. in magnesium-free restriction buffer containing 0.1 mg/ml acetylated bovine serum albumin, 1% β-mercaptoethanol, 0.1% Triton X-100 (Boehringer Manheim, membrane quality), and 0.2 μg/ml 4', 6-diamino-2 phenylindole dihydrochloride (DAPI) with slow shaking. Equilibrated samples ranging in volume from 50 to 100 μl were melted at 72° C. for 5 minutes, and then cooled to 37° C. Approximately 0.3–0.5 ul of enzyme (2 to 14 units/μl) was spread on a slide. Enzyme reaction temperatures were as recommended by manufacturers. β-mercaptoethanol was added to discourage photolysis (M. Yanagida et al. in *Applications of Fluorescence in the Biomedical Sciences*, D. L. Taylor et al., Eds. (Alan R. Liss, New York, 1986), pp. 321–345.) and was tested at this concentration for any deleterious effects on digestion using electrophoresis. A 7 μl volume of the melted sample was typically pipetted (slowly) using a wide bore pipette tip onto an 18×18 mm cover glass and rapidly deposited onto a slide. Timing and quenching of the gel is critical for controlling elongation. The reaction chamber was then sealed with mineral oil to avoid evaporation, and the agarose was allowed to gel for at least 30 minutes at 4° C., prior to diffusion of 50 mM MgCl2 through an open space. For chromosome I(240 kb) and III (345 kb), slides were in a cold desiccator (4°) prior to casting to hasten gelling avoiding premature molecular relaxation. For the larger chromosomes, which relax more slowly, slides were kept at room temperature. The slide was placed on a temperature controlled microscope stage at 37° C. (except CspI, 30° C.). These images clearly show progressive digestion by the appearance of growing gaps in the fixed molecules. From such data fragment, order was determined from inspection of time-lapse images obtained every 20 seconds. DNA molecules were imaged using a Zeiss Axioplan or Axiovert 135 microscope equipped for epi-fluorescence (487901 filter pack for UV excitation and Blue emission) and a 100× or 63× Plan-Neofluar objective (Zeiss) coupled to Hammamatsu C2400 SIT cameras. Care was taken to adjust the camera controls to avoid saturating the digitizer at either end of the intensity range. Every 20 seconds, 32 video frames were digitized to 8 bits and integrated to give 13 bit precision by a Macintosh based Biovision image processor or a Pixel pipeline digitizer (Perceptics Corp.). A computer controlled shutter was used to limit illumination to 1.5 seconds per image giving a total of about 135 to 255 seconds for typical experiments. Neutral density filters were used to keep the illumination intensity below 100 μW measured at the objective. Control experiments showed no damage to DNA molecules under these conditions. Digitized images were recorded directly to disk and archived on tape. Since observed molecules tend to move and can sometimes be confused with other molecules, inspection of a "cutting sequence" or "cutting movie" simplifies deconvolution of molecule-molecule interactions. Agreement is excellent between the optical (length or intensity) and the electrophoresis based maps. The third type of restriction maps ("Com", FIG. 7) results from combining length and intensity derived data: data from small restriction fragments (<60 kb) were sized by length, while intensity measurements provide the balance of fragment sizes needed to complete the maps.

FIG. 14 shows the ordered restriction maps created from Rsr II digestion of chromosome III and XI and Asc I digestion of chromosome XI by optical mapping, while FIG. 15 shows the corresponding fluorescence micrographs of typical digests. Relative apparent length results, using the pooled population standard deviation of 47 kb to calculate confidence intervals. Chromosome, enzyme, mean+/−90% confidence kb (number of samples). Ch. III Rsr II 264+/− 27(8), 86+/−27(8). Ch. XI Asc 142+/−55(2), 195+/−55(2), 242+/−55(2). Ch. XI Rsr II 67+/−45(3), 127+/−45(3), 221+/−45(3), 260+/−45(3). Relative fluorescence intensity results, using the pooled population standard deviation of 36 kb to calculate confidence intervals. Ch. III Rsr II 256+/− 21(8). Ch. XI Asc I 80+/−42(2), 177+/−42(2), 181+/−42(2), 237+/−42(2). Ch. XI Rsr II 84+/−34(3), 125+−34(3), 226+/− 34(3), 240+/−34(3). There are no published maps available for independent verification of these results. These maps are constructed by first determining the maximum number of cleavage sites from cutting frequency data (similar to FIG. 7). Fragments from fully cut molecules are then sized by length and intensity and sorted into bins for averaging. Relative fluorescence intensity measurements are used to sort length measured fragments. Obviously, adjacent fragments must go into adjacent bins for averaging. Distinctive patterns in a digest, such as a very large fragment lying next to a very small one, facilitate accurate sorting. Data from partial digests was also used to confirm the maps. Data from partial digests was used to confirm the map constructed from fully cut molecules by calculating the expected partial fragment lengths and comparing these to the observed data.

A new set of analytical approaches to physical mapping of very long molecules, such as DNA molecules, is thus provided according to the present invention, that is simple and intrinsically very rapid. A nearly real time mapping procedure for chromosomes of yeast has been implemented, but this is far from the ultimate capability of the methodology. Since most traditional tools of genomic analysis are bypassed, including cloning, electrophoresis, Southern analysis and PCR, additional speed increases in optical mapping are not predicated on advances in robotics or automation (Chumakov, *Nature* 359:380, 1992). Simple engineering advances in chamber design, sample handling, image analysis and informatics should make available a high throughput methodology capable of rapidly mapping entire genomes and, more importantly, extending knowledge of sequence information to populations of individuals rather than prototypes of each organism (Cavalli-Sforza, *Am. J. Hum. Genet* 46:649, 1990).

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

References

1. Mullis, K. B. and Faloona, F. A. (1987), Specific synthesis of DNS in vitro via a polymerase-catalyzed chain reaction. Methods in Enzymol 155:335–350.
1. Schwartz, D. C., Saffran, W., Welsh, J., Hass, R., Goldenberg, M. and Cantor, C. R. (1983). New technique for purifying large DNAs and studying their properties and packaging. Cold Spring Harbor Symp. Quant. Biol. 47:189–195.
2. Schwartz, D. C. and Cantor, C. R. (1984), Separation of yeast chromosome-sized DNAs by pulsed-field grandient electrophoresis. Cell 37:67–75.
3. Carle, G. F. and Olson, M. V. (1984). Separation of chromosomal DNA molecules from yeast by orthogonal-field. Nucleic Acids Res. 12:5647–5664.
4. Chu, G., Vollrath, D., and Davis, R. W. (1986), Separation of large DNA molecules by contour clampled homogeneous electric fields. Science 234:1582–1585.
5. Clark, S. M., Lai, E., Birren, B. W. and Hood, L. (1988). A novel instrument for separating large DNA molecules with pulsed homogeneous electric fields. Science 241:1203–1205.
6. Barlow, D. P. and Lehrach, H. (1987). genetics by gel electrophoresis: the impact of pulsed field gel electrophoresis on mammalian genetics. Trends in Genetics 3:167–177.
7. Chandrasekharappa, S. C., Marchuk, D. A. and Collins, F. S. (1992). Analysis of yeast artificial chromosome clones. In Methods in Molecular Biology: Pulsed-field gel Electrophoresis, vol. 12 (Eds, M. Burmeister and L. Ulanovsky), The Humana Press, pp. 235–257.
8. Burke, D. T., Carle, G. F., and Olson, M. B. (1987). Cloning of large segments of exogenous DNA into yeast by means of artificial chromosome vectors. Science 236:806–812.
9. Murray, A. W. and Szostak, J. W. (1983). Construction of artificial chromosomes in yeast Nature 305:189–193.
10. Bellanne-Chantelot, C. Lacroix, B., Ougen, P., Billault, A., Beaufils, S., Bertrand, S., Georges, I., Glibbert, F., Gros, T., Lucotte, G., Susini L., Copdani, J., Gesnouin, P., Pookk, S., Vaysseix, G., LuKuo, J., Ried, T., Ward, D., Chumakov, I., LePaslier, D., Barillot, C C. and Cohen, D. (1992). mapping the whole human genome by fingerprinting yeast artificial chromosomes. Cell 70:L 1059–1068.
11. Brownstein, M., Silverman, G. A., Little, R. D., Burke, D. T., Korsmeyer, S. J., Schlessinger, D., and Olson, M. V. (1989). Isolation of single-copy human genes from a library of yeast artificial chromosome clones. Science 244:1348–1351.
12. Schlessinger, D. and Kere, J. (1992), YAC-based mapping of Genome Structure, Function and Evolution. In Genome Analysis, Vol. 4, Strategies for Physical mapping (Eds. K. E. Davies and S. M. Tilghman), Cold Spring Harbor Laboratory Press, pp. 131–159.
13. Campbell, C., Gulati, R., Nandi, A. <., Floy, K. and Hieter, P. (1991). Generation of a nested series of interstitial deletions in yeast artificial chromosomes carrying human DNA. Proc. Natl. Acad. Sci. USA 88 5744–5748.
14. Zimm, G. H. and Levene, S. D. (1992), Problems and propsects in the theory of gel electrophoresis of DNA Quarterly Reviews of Biophysice. 25:171–204.
15. Calladine, C. R., Collis, C. M., Drew, H. R., and Mott M. R. (1991). A study of electrophoretic mobility of DNA in agarose and polyacrylamide. journal of Molecular Biology. 221:981–1005.
16. Louise D. and Serwer, P. (1989). A hybrid mode of rotating gel electrophoresis for separating Linear and circular duplex DNA. Applied and Theoretical Electrophoresis I:169–173.
17. Noolandi, J., Slater, G. W., Lim, H. A., and Viovy J. L. (1989). Generalized tube model of biased reptation for gel electrophoresis of DNA. Science 243:1456–1458.
18. Deutsch, J. M. (1988). Theoretical studies of DNA during gel elecctrophoresis Science 240:992–924
19. Glazer, A. N. and Rye, H. S. (1992). Stable dye-DNA intercalation complexes as reagents for high sensitivity fluorescence detection. Nature 359:859–861.
20. Quesada, M., Rye, H. S. Gingrich, J. C., Glazer, A. N. and Mathies, R. A. (1991). High-sensitivity DNA detection with a laser-excited confocal fluorescence gel scanner. BioTechniques 10:616–625.
21. Mathies, R. A. and Hung, X. C. (1992), Capillary array electrophoresis: an approach to high-speed, high-throughput DNA sequencing. Nature 359:167–169.
22. Glazer, A. N., Peck, K. and Mathies, R. A. (1990). A stable double-stranded DNA-ethidiuum homodimer complex: Application to picogran fluorescence detection of DNA in agarose gels. Proc. Natl. Acad. Sci. USA 87:3851–3855.
23. Mathies, R. A., Peck, K. and Stryer, L. (1990). Optimization of high-sensitivity fluorescence detection. Anal. Chem 62:1786–1791.
24. Ried, T., Baldini, A., Timothy, C. R., Ward, D. C. (1992). Simultaneous visualization of seven different DNA probes by in situ hybridization using combinatorial fluorescence and digital imaging microscopy. Proc. Natl. Acad. Sci. USA 89: 1388–1392.
25. Murakami, A., Tada, J., Yamagata, K. and takano, J. (1989). Highly sensitive detection of DNA using enzyme-linked DNA-probe. 1. Colorimetric and fluorometric detection. Nucleic Acids Res. 17:5587–5595.
26. Beck, S., O'Keeffe, T., M. Coull, J. and Koster, H. (1989). Chemiluminescent detection of DNA: application for DNA sequencing and hybridization. Nucleic Acids Res. 17:5115–5123.
27. Lehrach, H., Drmanac, R., Hoheisel, J., Larin, Z 1, Lennon, G., Monaco, A. P., Nizetic, D., Zehetner, G., Poustka, A. (1989). Hybridization fingerprinting in genome mapping and sequencing in Genetic and Physical mapping. (Eds., Davies, K. E., and Tilghman, S. M.) Cold Spring Harbor Laboratory Press, cold Spring Harbor, N.Y., pp 39–81.
28. Larin, Z., Monaco, A/P/and Lehrach, H. (1991). Yeast artificial chromosome libraries containing large inserts from mouse and human DNA, Proc. Natl. Acad. Sci., 88:4123–4127.
29. Anderson, C. (1993). Genome shortcut leads to problems. Science 259:1684–1687.
30. Chumakov, I. et al. (1992). Continuum of overlapping clones spanning the entire human chromosome 21q. Nature 359:380–387.
31. Vollrath, D., Foote, S. Hilton, A., Brown, L. G., Beer-Romero, P., bogan, J., and Page, D. C. (1992). The Human Y chromosome: A 43-Interval map Based on Naturally Occurring Deletions. Science 258:52–59.
32. Foote, S., Vollrath, D., Hilton, A. and Page, D. C. (1992) The Human Y Chromosome: Overlapping DNA Clones Spanning the Euchromatic Regioin. Science 258:60–66.
33. Donis-Keller, H., green, P., Helms, C., Cartinhour, S., Weiffenbach, B., Stephens, K., Keith, T. P., Bowden, D. W., Smith, D. R., Lander, E. S., Botstein, D., et al. (1987). A genetic linkage map of the human genome. Cell 51:319–337.
34. Olson, M. V., Dutchik, J. E., Graham, M. Y., Brodeur, G. M., Helms, C., Frank, M., MacCollin, M., Scheinman, R. and Frank, T. (1986). Random-clone strategy for genomic restriction mapping in yeast. Proc. Natl. Acad. Sci. USA 83:7826–7830.
35. NIH-CEPH Collaborative mapping Group, (1992). A Comprehensive Genetic Linkage Map of the Human Genome. Science 258:67–86.
36. Mandel, J-L., Monaco, A. P., Nelson, D. L., Schlessinger, D. 1, Willard, Huntington (1992). Genome Analysis and the Human X Chromosome. Science 258:103–109.
37. Stallings, R. L., Torney, D. C., Hildebrand, C. E., Longmire, J. L., Deaven, L. L., Jett, J. H., Doggett, N. A. and Moysis, R. K. (1990). Physical mapping of human chromosomes by repetitive sequence fingerpringing proc. Natl. Acad. Sci. USA 87:6218–6222.
38. Craig, G., Nizetic, D., Hoheisel, J. D., Zehetner, G. and lehrach, H. (1990). Ordering of cosmid clones covering the Herpes simplex virus type I (HSV I) genome: a test case for fingerprinting by hybridization. Nucl. Acids.Res. 18:2653–2660.
39. Coulson, A., Sulston, J., Brenner, S., and Kam, J. (1986). Towards a physical map of the nematode C. elegans. proc. Natl. Acad. Sci. USA 83:7821–7825.
40. Ross, M. T., Hoheisel, J. D., Monaco, A. P., Larin, Z., Zehetner, G. and Lehrach, H, (1992). High-density gridded YAC filters: their potential as genome mapping tools In Techniques for the analysis of complex genomes (Anand, R.). Academic Press Inc., San Diego, Calif.
41. Church, C. and Kiefer-higgins, S. (1988). Multiplex DNA sequencing. Science 240:185–188.
42. Smith, H. O and Bernstiel, M. L. (1976). A simple method for DNA restriction site mapping. Nucleic Acids Res. 3:2387.
43. Yanagida, M., Hiraoka, Y., and Katsura, I. (1983) Cold Spr. Harb. Symp. on Quant. Biol. XLVII: 177–187.
44. Schwartz, D. C., Hernandez, L.I., Wang, Yu-Ker Wang, Ramnarain, S. P., Huff, E., and Li, X. (1993). Ordered Restriction Maps of *Saccharomyces cerevisiae* Chromosomes Constructed by optical mapping, Submitted to Science.
45. Guo, X. H., Huff, E. J. and Schwartz, D. C. (1992). Sizing single DNA molecules. Nature 359:783.
46. Guo, X. and Schwartz, D. C. Molecular Sizes As Determined by Imaging Coil Dynamics in Agarose Gel. Manuscript to be submitted.
47. Mickel, S., Arena, V., and Bauer, W. (1977). Physical properties and gel electrophoresis behavior of R12-derived plasmid DNAs. Nucleic Acids Res. 4:1465–1482.
48. Ashburner, M. (1989). Drosophila, A Laboratory Handbook. Cold Spring Harbor Laboratory Press, Cold Spring Harbor, N.Y.
49. Osheroff, N., Shelton E. R., Brutlag, D. L. (1983). DNA topoisomerase II from *Drosophila melanogaster*. Relaxation of supercoiled DNA. J. Biol. Chem 258:9536–9543.
50. Fan, J. B., Chikashige, Y., Smith, C. L., Niwa, O., yanagida, M. and cantor, C. R. (1989). Construction of a Not I restriction map of the fission yeast *Schizosaccharomyces pombe* genome. Nucleic Acids Res. 17:2801–2818.
51. Ruvolo, P., Hsu, M., and Schwartz, D. Separating the Smallest Drosophila Chromosome by Pulsed Oriented Electrophoresis. Manuscript in preparation.
52. Schwartxz, D. C., Koval, M. (1989). Conformational dynamics of individual DNA molecules during gel electrophoresis. nature 338:520–522.
53. Holm, C., Goto, T., Wang, J. C., Botstein, D. (1985). DNA topoisomerase II is required at the time of mitosis in yeast. cell 41:553–563.
54. Schwartz, D. C. (1985)> Giga-dalton DNA molecules, Ph.D. Thesis, Columbia Universiity, New York, N.Y.
55. Turmel, C., Brassard, e., Forsyth, R., Hook, K., Slater, G. W. and Noolandi, J. (1990). High resolution zero integrated field electrophoresis (ZIFE) of DNA. In Current communications in cell and molecular biology: Electrophoresis of large DNA molecules: Theory and applications, Cold Spring Harbor Laboratory, Cold Spring Harbor, N.Y., pp 101–131.

56. Viovy, J-L, Miomandre, F., Miquel, M-C., Caron, F., and Sor. F. (1992). Irreversible trapping of DNA during crossed-field gel electrophoresis. Electrophoresis 13:1–6.
57. Gemmill, R. M. (1991). Pulsed-field gel electrophoresis. In Adv. Electrophoresis 4":1–48.
58. Smith, S. B. and Bendich, A. J. (1990). Electrophoretice charge density persistence length of DNA as measured by fluorescence microscopy. Biopolymer 29:1167–1173.
59. Cai, W. and Schwartz, D. C. Why Large DNA Molecules Don't Enter Gels: The Mechanism of Trapping. To Be Submitted.
60. Roberts, T. M., Lauer, G. D., Klotz, L. C. (1975). Physical techniques for genome analysis. CRC Crit. Rev. Biochem. 3:349.
61. Smith, S. B., Aldridge, P. K., and Callis, J. B. (1989). Observation of individual DNA molecules undergoing gel electrophoresis. Science 243:203–206.
62. Zimm, B. H. (1991). "Lakes-straits" model of field-inversioin electrophoresis of DNA. J. Chem Phys. 94:2187–2206.
63. Wells, R. D., Klein R. D. and Singleton, C. K. (1981). Type II restriction enzyme. In the Enzymes (P. D. Boyer, Ed.), Academic Press, New York, N.Y., Ed. 3, vol. 14, part A, pp. 167–169.
64. Link, A. J. and Olson, M. V. (1991). Physical map of the *Saccharomyces cerevisiae* genome at 110-kilobase resolution. Genetics 127:681–698.
65. Koob, M. and Szybalski, W. (1990). Cleaving yeast and *Escherichia coli* genomes at single site. Science 250:271–273.
66. Koob, M., Burkiewicz, A., Kur, J. and Szybalski, W. (1992). RecA-AC: single-site cleavage of plasmids and chromosomes at any predetermined restriction site. Nucleic Acids Res. 20:5831–5836.
67. Ferrin, L. J. & Camerini-Otero, R. D. (1991). Selective cleavage of human DNA: RecA-assisted restriction endonuclease (RARE) cleavage. Science 254:L 1494–1497.
68. Lai, M. H., Kirsch, D. R. (1989). Nucleotide sequence of cytochrome P450 L1A1 from *Candida albicans*. Nucleic Acids Res. 17:804.
69. Ranmpino, N. J. and Chrambach, A. (1991). Conformational correlatives of DNA band compression and bidirectional migration during field inversion gel electrophoresis, detected by quantitative video epifluorescence micreoscopy. Biopolymers 31:1297–1307
70. Noolandi, J., Slater, G. W., Lim, H. A., and Viovy, J. L. (1989). Generalized tube model of biased reptation for gel electrophoresis of DNA. Science 243:1456–1458.
71. Zimm, B. H. (1956). Dynamics of polymer molecules in dilute solution: viscoelasticity, flow birefringence and dielectic loss. J. Chem. Phys. 24:269–278.
72. Rouse, P. E. (1953). A theory of the linear viscoelastic properties of dilute solutions of coiling polymers. J. Chem. Phys 21:1272–1280.
73. De Gennes, P-G. (1979). Scaling concepts in polymer physics. Cornell University Press, Ithaca, N.Y.
74. Doi, M. and Edwards, S. F. (1986). The Theory of Polymer Dynamics, Oxford University Press.
75. Smith, S. B. and Bendich, A. j> (1990). Electrophoretic charge density and persistence length of DNA as measured by fluorescence microscopy. Biopolymer 29:1167–1173.
76. Smith, S. B., Finzi, I. and Bustamante, C. (1992). Direct mechanical measurements of the elasticity of single DNA molecules by using magnetic beads Science 258:1122–1126.
77. Holzwarth, G., Platt, K. f., mckee, C. B., Whitcomb, R. W. and crater, G. D. (1989). the acceleration of linear DNA during pulsed-field gel electrophoresis. Biopolymers 28:1043–1058.
78. Borejdo, J. and Defea, K. (1988). The orientation of DNA fragments in the agarose gel. Anal. Biochem. 174:393-398.
79. Borejdo, J. (1989). Orientation of DNA in agarose gels. Biophys. J. 55:1183–1190.
80. Matsumoto S. Morikawa K. Yanagida M. (1981). Light microscopic structure of DNA in solution studied by the 4'6-diamidino-2-phenylinddole staining method. Journal of Mol. Biol. 132:501–516.
81. Olivera, B. M., Baine, P. and Davidson, D. (1964). Electrophoresis of the nucleic acids. Biopolymers 2:245–257.
82. Klotz, L. C. and Zimm, B. H. (1972). Retardation times of deoxyribonucleic acid solution, II: Improvements in appratus and theory. Macromolecules 5:471–481.
83. Rau, D. c. and Bloomfield, V. A. (1979). Transient electric birefringencce of T7 viral DNA. Biopolymers 18:L2783–2805.
84. Callis, P. R. and Davidson, N. (1969). Hydrodynamic relaxation times of DNA for decay of flow dichroism measurements. Biopolymers 8:379–390.
85. Taylor, D. L., Wang, Y-L, eds. (1989). Fluorescence Microscopy of Living Cells in Culture. Part B Academic press, Inc., New York, N.Y.
86. Arndt-Jovin, D. J., latt, S. A., Striker, G. and Jovin, T. M. (1979). Fluorescnece decay analysis in solution and in a microscope of DNA and chromosomes stained with quinacrine. J. Histochem. Cytochem. 27:87–95.
87. Cherry, R. J., ed. (1991). New Techniques of Optical microscopy and Microspectroscopy, CRC Press, Inc., Boca Raton, Fla.
88. Herman B. Jacobson, K. (1990). Optical Microscopy for Biology. A John Wiley & Sons, Inc. New York, N.Y.
89. Arndt-Jovin, D. J., Robert-Nicoud, M., Kaufman, S. J. and Jovin, T. M. (1985). Fluorescence digital imaging microscopy in cell biology. Science 230:247–256.
90. Hiraoka, Y., Sedat, J. W. and Agard, D. A. (1987). The use of a charge-coupled device for Quantitative optical microscopy of biological structures. Science 238:36–41.
91. Aikens, R. S., Agard, D. A. and Sedat, J. W. (1989). Solid-state imagers for microscopy. In Fluorescence microscopy of living cells in culture, Vol 29 (Eds. Wang, Y-L, Taylor, D. L.) Academic Press, Inc. pp. 291–313.
92. Brun, A. M., Harriman, A. (1992). Dynamics of electron transfer between intercalated polycyclic milesules: effect of interspersed bases. J. Am. chem. Soc. 114:3656–3660.
93. Volkmuth, W. D., Austin, R. H. (1992). DNA electrophoresis in microlithographic arrays.; nature 358:L600–602.
94. Cantor, R. C. and Schimmel, P. R. (1980). Biophysical chemistry, Part II: The conformation of biological 95. Manuelidis, L., Langer-Safer, P. R. and Ward, D. C. (1982). High-resolution mapping of satellite DNA using biotin-labeled DNA probers. J. cell Biol. 95:L619–625.
96. Lawrence, J. B., Villnave, C. A. and Singer, R. H. (1988). Sensitive, high-resolution chromatin and chromosome mapping in situ: Presence and orientation of two closely integrated copies of EBV in a lymphoma cell line. Cell 52:51–61.
97. Heng, H. H. Q., Squire, J. and Tsui, L-C. (1992). High-resolution mapping of mammalian genes by in situ hybridization to free chromatin. Proc. Natl. Acad. Sci., USA 89:9509–9513.
98. van den Engh, G., Sachs, R., Trask, B. J. (1992). Estimating genomic distance from DNA sequence location in cell nuclei by a random walk model. Science 257:1410–1412.
99. Wang, Y-K and Schwartz, D. C. (1993). Chopped inserts are a convenient alternative to beads. Submitted to Nucleic Acids Res.
100. Serwer, P. and Griess, G. A. (1990). Gel electrophoresis of micron-sized molecules: A problem and a solution. Biopolymers 29:1863–1866.
101. Rigas, B., Welcher, A. A., Ward, D. C. and Weissman, S. M. (1986). Rapid plasmid library screening using RecA-coated biotinylated probes. Proc. Natl. Acad. Sci., USA 83:9591–9595.
102. Landschulz, W-H, Johnson, P. F. and Mcknight, S. C. (1988). The Leucine zipper: A hypothetical structure common to a new class of DNA binding proteins. Science 240:1759–1764.
103. Hsieh, P., Camerini-Otero, C. S. and Camerini-Otero, R. D. (1992). The synapsis event in the homologous pairing of DNAs: RecA recognizes and pairs less than onehelical repeat of DNA. Proc. Natl. Acad. Sci. USA 89:6492–6496.
104. Beck, S. (1992), Nonradioactive detection of DNA Using Dioxetane Chemiluminescence. Methods in Enzymol. 216:143–153.
105. Murakami, A., Tada, J., Yamagata, K. and Takano, J. (1989). Highly sensitive detection of DNA using enzyme-linked DNA-probe. 1. Colorimetric and fluorometric detection. Nucleic Acids Res. 17:5587–5595.
106. Hyman, A. A., Middleton, K., Centola, M., Mitchison, T. J. and Carbon, J. (1992). Microtubule-motor activity of a yeast centromer-binding protein complex. Nature 359:L533–536.
107. Herman, B. (1989). Resonance energy transfer microscopy. Methods in Cell Biol. 30:219–243.
108. Uster, P. S. and Pagano, R. E. (1986) J. Cell Biol. 103:1221–1234.
109. Yanagida, M., Morikawa, K., Hiraoka, Y 1, matsumoto, S., Uemura, T., and Okada, S. (1986). In Applications of Fluorescence in the Biomedical Sciences (eds D. L. Taylor, A. S. Waggoner, R. F. Murphy, F. Lanni, and R. R. Birge), Alan R. Liss, Inc., New York, N.Y., pp. 321–345.
110. Kohara, Y., Akiyama, K. and Isono, K. (1987). The physical map of the whole E. coli chromosome: application of a new strategy for rapid analysis and sorting of a large genomic library. Cell 50:495–508.
111. Evans, G. A. and Lewis, K. A. (1989). Physical mapping of complex genomes by cosmid multiplex analysis. Proc., Natl. Acad. Sci. USA 86:5030–5034.
112. Smith, A. M., Birnstiel, M. L. (1976). A simple method for DNA restriction site mapping. Nucleic Acids Res. 3:2387–2399.
113. Barlow, D., Lehrach, H., Poustka, A., and Bates, G. (1989). Long range mapping and cloning of mammalian chromosomes. EMBO practical course. Heidelberg, FRG.
114. Rommens, J. M., Iannuzzi, M. C., Kerem, B-S, Drumm, M. L., Melmer, G., Dean, M., Rozmahel, R., Cole, J. L., Kennedy, D., Hidaka, N., Zsiga, M., Buchwald, M., Riordan, J. R., Tsui, L-C and Collins, F. S. (1989). Identificaiton of the cystic fibrosis gene: Chromosome walking and jumping. Science 245:1059–1065.
115. Riordan, J. R., Rommens, J. M., Kerem, B-S, Alon, N., Rozmahel, R., Grzelczak, Z., Zielenski, J., Lok, S., Plavsic, N., Chou, J-L., Drumm, M. L. Iannuzzi, M. C., Collins, F. S., Tsui, L-C (1989), Identification of the cystic fibrosis gene: cloning and characterization of complementary DNA. Science 245:1066–1072.
116. Zielenski, J. Rozmahel, R., Bozon, D., Kerem, B., Grzelczak, Z., Riordan, j. R. Rommens, J. M. and Tsui, L-C (1991). Genomic DNA sequence of the cystic fibrosis transmembrande conductance regulator (CFTR) gene. Genomics 10:214–220.
117. Olson, M., Hood, L., Cantor, C. and Botstein, D. (1989). A common language for physical mapping of the human geome. Science 245:1434–1435.
118. Pinkel, D., Lake, S., Gledhill, B. L., Van Dilla, M. A., Stephenson, D. and Watchmaker, G.(1982). High resolution DNA contene measurements of mammalian sperm. Cytometry 3:1–9.
119. Steen, H. B. and Lindmo, T. (1979). Flow cytometry: A high-resolution instrument for everyone. Science 204:403–404.
120. Dill, K. and Zimm, B. H. (1980). Dynamics of polymer solutions. 2. The determination of molecular weight distribution by viscoelasticity. Macromolecules 13:432–436.
121. Kavenoff, Rlk and Zimm, B. H. (1973). Chromosoma 41:1–27.
122. Sulston, J., Du, Z., Thomas, K., Wilson, R., Hillier, L., Staden, R., Halloran, N., Green, P., thierry-Mieg, J., Qiu, L, Dear, S., Couison, A., Craxton, M., Durgbin, R., Berks, M., Metzstein, M., Hawkins, T., Ainscough, R. and Waterston, R. (1992). The *C elegans* genome sequencing project: a beginning. Nature 356:37–41.
123. Balding, D. J., Torney, D. C.(1991). Statistical analysis of DNA fingerprint data for ordered clone physical mapping of human chromosomes. Bulleting of Mathematical Biology 53:853–879.
124. Kuspa, A., Vollrath, D., Cheng, Y and Kaiser K. (1989). Physical mapping of the Myxococcus xanthus genome by random cloning in yeast artifical chromosomes. Proc. Natl. Acad. Sci. USA 86:8917–8920.
125. Shafit-Zagardo, B., Maio, J. J. and Brown, F. L. (1982). L1 families of long, interspersed repetitive sequences in human and other primate genomes. Nucleic Acids Res. 10:3175–3193.
126. Botstein, D., White, R. L., Skolnick, M. and Davis, R. W. (1980). Construction of a genetic linkage map in man using restriction fragment length polymorphisms. Am. J. Hum. Genet. 32:314–331.

What is claimed is:

1. A method for determining a property of a DNA molecule, comprising the steps of labeling the DNA molecule with a fluorescent agent;

applying an electrical force to elongate a single DNA molecule;

applying exciting light to the DNA molecule to excite fluorescence in the fluorescent agent; and observing the fluorescence from the DNA molecule to determine a property of the molecule.

2. A method as claimed in claim 1 wherein the property determined is sequence of the DNA molecule.

3. A method as claimed in claim 1 wherein the step of optically isolating the DNA molecule includes elongating or stretching out the DNA molecule.

4. A method as claimed in claim 1 wherein the observing is performed by a microscope.

5. A method as claimed in claim 1 wherein the observing is performed by a spectrographic apparatus.

6. A method for determining one or more properties of a DNA molecule comprising the steps of attaching a light responsive agent to the DNA molecule;

applying an electrical force to elongate the DNA molecule such that the DNA molecule can be analyzed separately from other DNA molecules;

exciting the DNA molecule with light to excite the light responsive element; and observing the light from the DNA molecule to determine one or more properties of the DNA molecule.

7. A method as claimed in claim 6 wherein the property determined is sequence of the DNA molecule.

8. A method as claimed in claim 6 wherein the step of manipulating the DNA molecule includes elongating or stretching out the DNA molecule.

9. A method as claimed in claim 6 wherein the observing is performed by a microscope.

10. A method as claimed in claim 6 wherein the observing is performed by a spectrographic apparatus.

* * * * *